(12) United States Patent
Chandrasoma

(10) Patent No.: US 10,898,127 B2
(45) Date of Patent: Jan. 26, 2021

(54) PATHOLOGIC ASSESSMENT OF LOWER ESOPHAGEAL SPHINCTER DAMAGE

(71) Applicant: Parakrama Chandrasoma, Pasadena, CA (US)

(72) Inventor: Parakrama Chandrasoma, Pasadena, CA (US)

(*) Notice: Subject to any disclaimer, the term of this patent is extended or adjusted under 35 U.S.C. 154(b) by 966 days.

(21) Appl. No.: 15/481,225

(22) Filed: Apr. 6, 2017

(65) Prior Publication Data

US 2017/0290542 A1 Oct. 12, 2017

Related U.S. Application Data

(60) Provisional application No. 62/380,310, filed on Aug. 26, 2016, provisional application No. 62/320,189, filed on Apr. 8, 2016.

(51) Int. Cl.
*A61B 5/00* (2006.01)
*A61B 10/02* (2006.01)
(Continued)

(52) U.S. Cl.
CPC ............ *A61B 5/4233* (2013.01); *A61B 1/233* (2013.01); *A61B 5/0066* (2013.01);
(Continued)

(58) Field of Classification Search
CPC ..... A61B 5/066; A61B 5/0084; A61B 5/4233; A61B 5/4836; A61B 5/6852; A61B 1/233; A61B 10/0283; A61B 10/04
See application file for complete search history.

(56) References Cited

U.S. PATENT DOCUMENTS

| 6,077,230 A | 6/2000 | Gregoire et al. |
| 8,002,713 B2 | 8/2011 | Heske et al. |
| 2007/0027407 A1 | 2/2007 | Miller |

FOREIGN PATENT DOCUMENTS

| CN | 103860207 | 6/2014 |
| RU | 2290864 C1 * | 1/2007 |

OTHER PUBLICATIONS

Bonavina, L et al., Role of the Overall Length of the Distal Esophageal Sphincter in the Antireflux Mechanism, Diseases of the Esophagus, 1988.

(Continued)

*Primary Examiner* — Boniface N Nganga
(74) *Attorney, Agent, or Firm* — Knobbe, Martens, Olson & Bear, LLP

(57) ABSTRACT

Determining the progression of reflux disease in the esophagus of a patient includes identifying the location of an endoscopic gastroesophageal junction in the esophagus, removing a length of tissue of the esophagus that includes a portion of the endoscopic gastroesophageal junction, and identifying the proximal limit of tissue containing cardiac epithelium. Determining the length of the squamo-oxyntic gap of the biopsied tissue can involve measuring the length of tissue extending between the proximal limit of tissue containing gastric oxyntic epithelium to the proximal limit of tissue containing cardiac epithelium. A linear relationship can be determined from a slope of a line extending between a first data point and a second data point that can determine a target age of the patient when the lower esophageal sphincter will have a certain length.

20 Claims, 24 Drawing Sheets

(51) Int. Cl.
A61B 10/04 (2006.01)
A61B 1/233 (2006.01)
(52) U.S. Cl.
CPC .......... *A61B 5/0084* (2013.01); *A61B 5/6852* (2013.01); *A61B 10/0283* (2013.01); *A61B 10/04* (2013.01)

(56) References Cited

OTHER PUBLICATIONS

Chandrasoma P, Wijetunge S, Ma, Y, DeMeester S, Hagen J, DeMeester T. The dilated distal esophagus: a new entity that is the pathologic basis of early gastroesophageal reflux disease. Am J Surg Pathol 2011;35:1873-1881.
Chandrasoma P. A proposal for a new validated histologic definition of the gastroesophageal junction. Hum Pathol 2006;37:40-47.
Chandrasoma PT, Der R, Ma Y, Dalton P, Taira M. Histology of the gastroesophageal junction. An autopsy study. Am J Surg Pathol 2000;24:402.
Chandrasoma PT. Histologic definition of gastro-esophageal reflux disease. Curr Opin Gastroenterol. Jul. 2013;29(4):460-7.
Chandrasoma PT et al., A New Pathologic Assessment of Gastroesophageal Reflux Disease: The Squamo-Oxyntic Gap in Stem Cells, Pre-neoplasia, and Early Cancer of the Upper Gastrointestinal Track, Aug. 30, 2017, vol. 30 of the series Advances in Experimental Medicine and Biology, pp. 41-78; first paragraph of abstract.
Chandrasoma PT et al., The Histologic Squarmo-oxyntic Gap: An Accurate and Reporducible Diagnostic Marker of the Gastroesophageal Reflux Disease, The American Journal of the Surgical Pathology, Nov. 2010, vol. 34, No. 11, Abstract.
Chandrasoma, PT, et al., Definition of Histopathologic Changes in Gastroesophageal Reflux Disease, The American Jounal of Surgical Pathology, Mar. 2000, vol. 24, No. 3, pp. 344-351.
Kahrilas PJ, Shi G, Manka M, Joehl RJ. Increased frequency of transient lower esophageal sphincter relaxation induced by gastric distension in reflux patients with hiatal hernia. Gastroenterology 2000; 118:688-695.
Korn O, Csendes A, Burdiles P, Braghetto I, Stein HJ. Anatomic dilatation of the cardia and competence of the lower esophageal sphincter: A clinical and experimental study. J Gastrointest Surgery 2000; 4:398-406.
Pohl H, Sirovich B, Welch G. Esophageal adenocarcinoma incidence: are we reaching the peak? Cancer Epidemiol Biomarkers Prev 2010;19:1468-1470.
Robertson EV. Central Obesity in Asymptomatic Volunteers is associated with increased intrasphincteric acid reflux and lengthening of cardiac mucosa. Gastroenterology 2013; 145:730-739.
Sarbia M. Histopathology of the gastroesophageal junction. A study on 36 operation specimens. Am J Surg Pathol 26:2002; 1207-1212.
Tobey NA, et al. Dilated intercellular spaces and shunt permeability in non-erosive acid-damaged esophageal epithelium. Am J Gastroenterol 2004; 99:13-22.
Zaninotto G, DeMeester TR, Schwizer W, Johansson K-E, Cheng S-C. The lower esophageal sphincter in health and disease. Am J Surg 1988;155;104-111.
PCT Search Report and Written Opinion for PCT Application No. PCT/US17/26342 dated Jul. 7, 2017 in 24 pages.

* cited by examiner

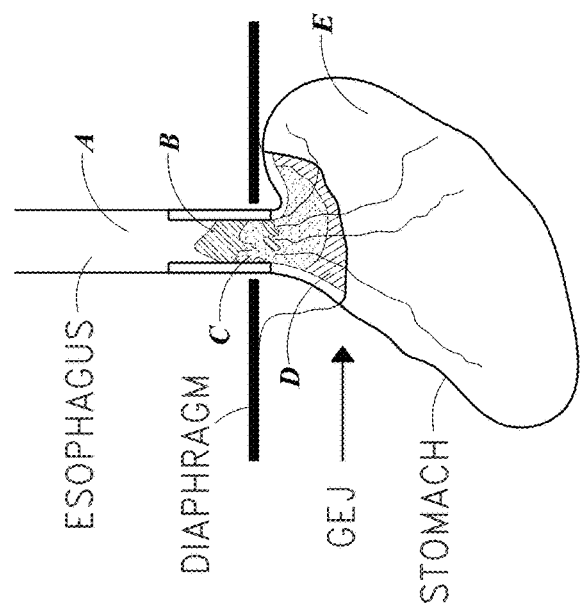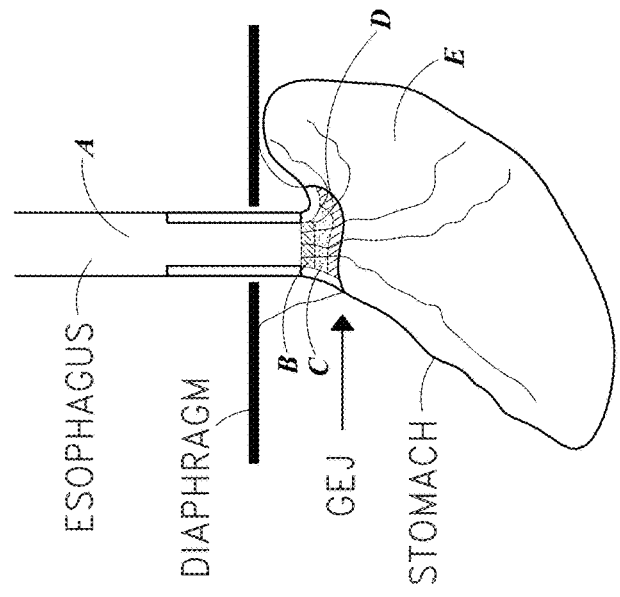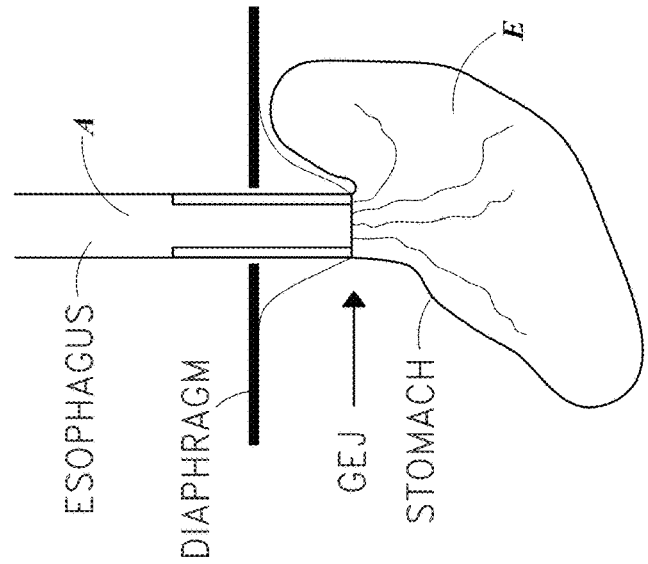

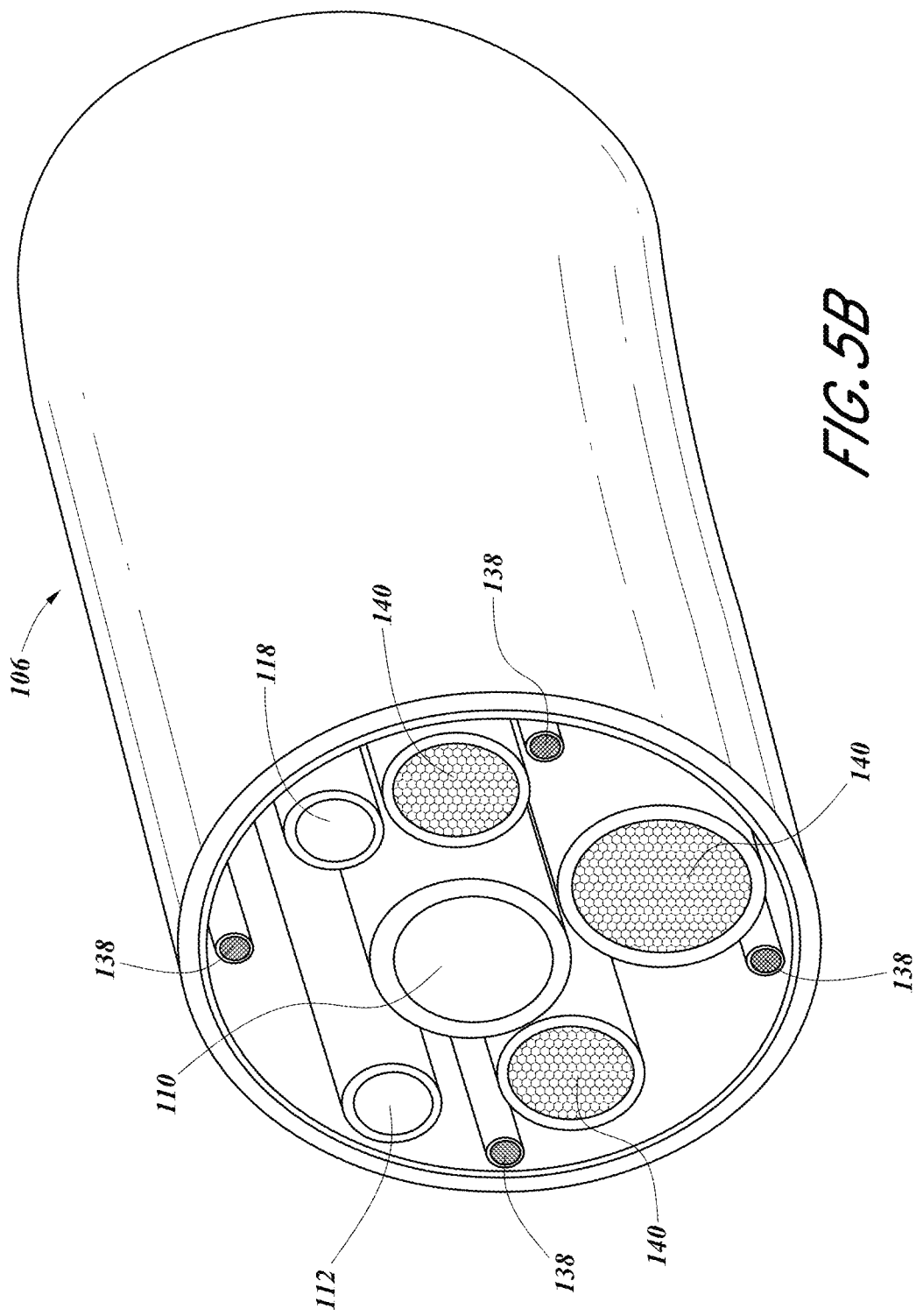

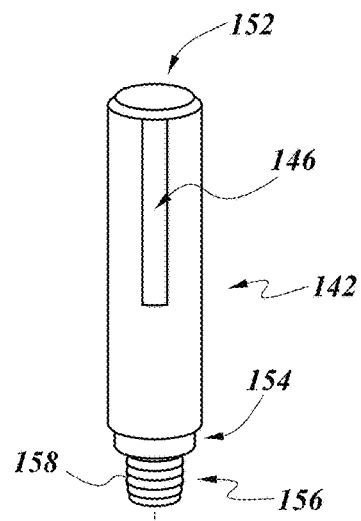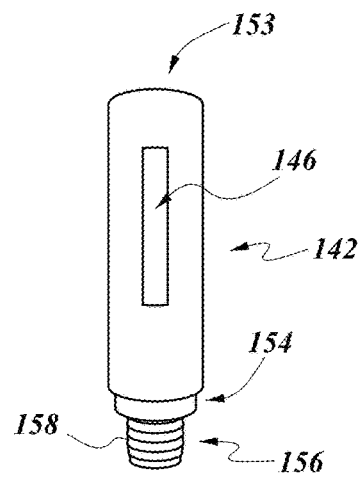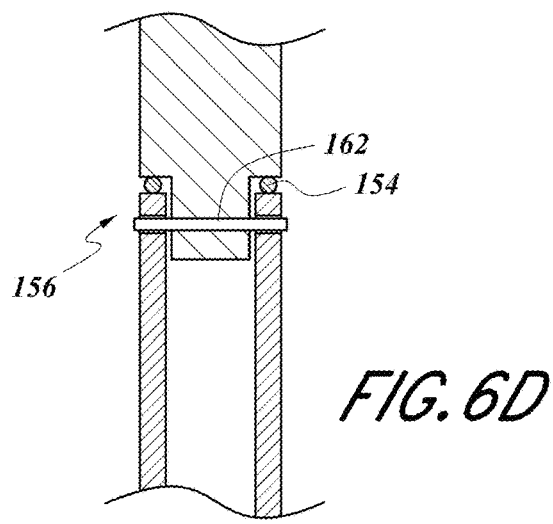
FIG. 6B
FIG. 6C
FIG. 6D

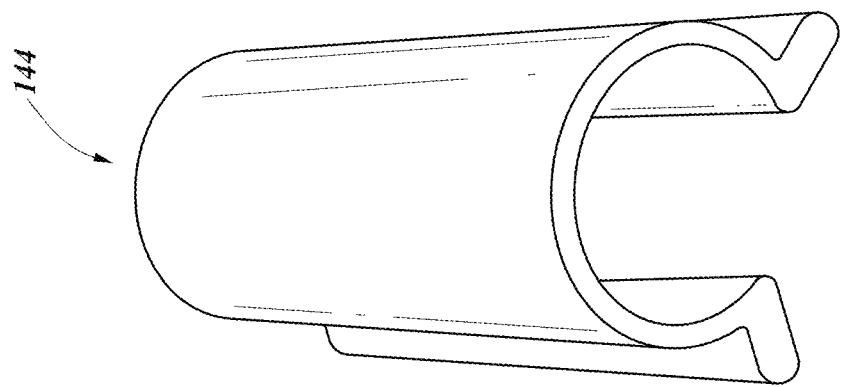
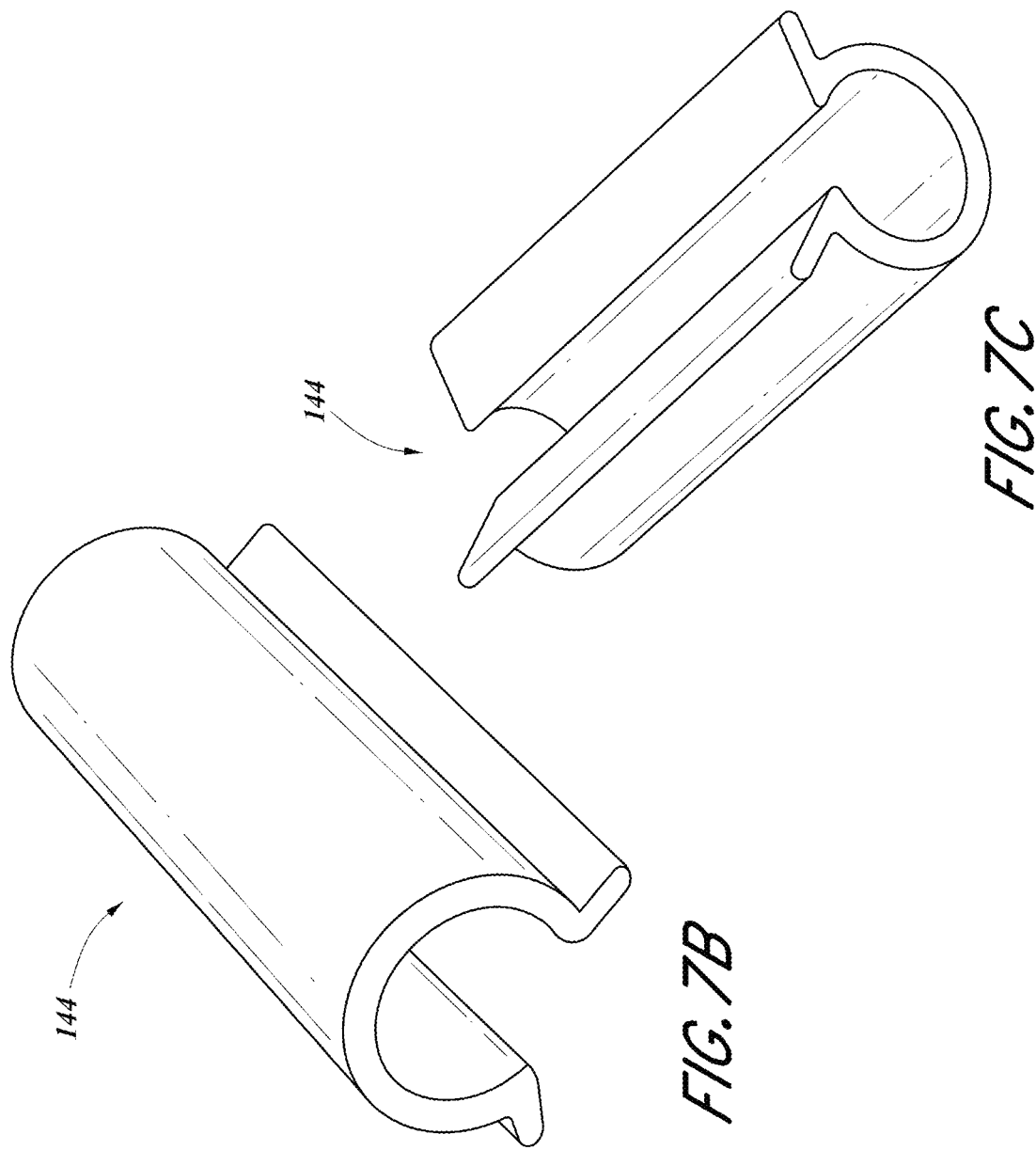

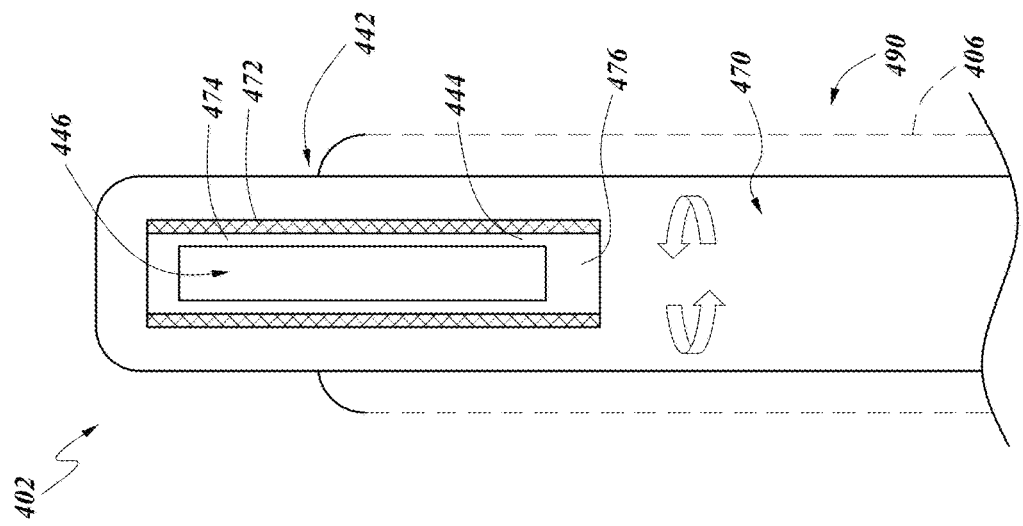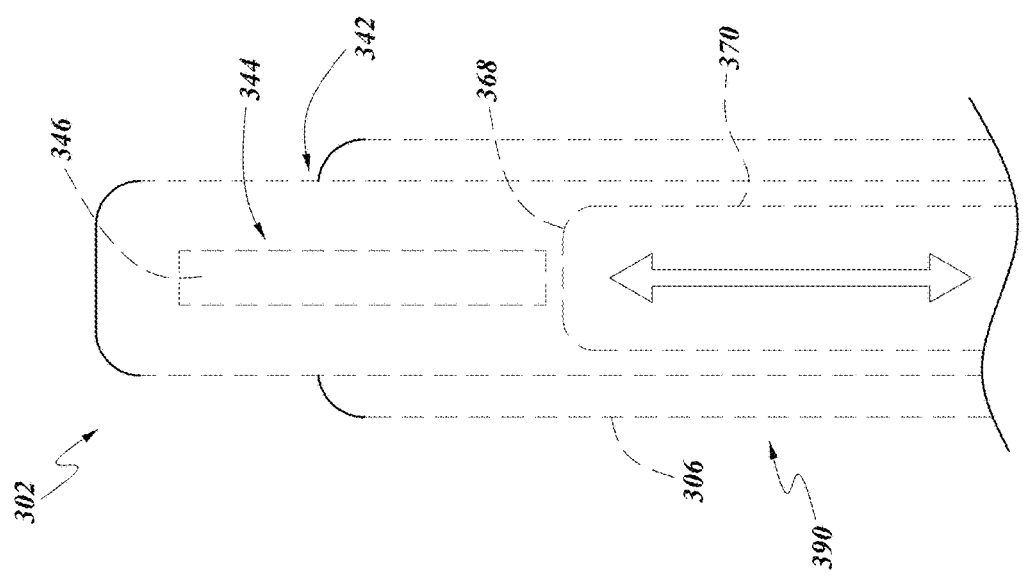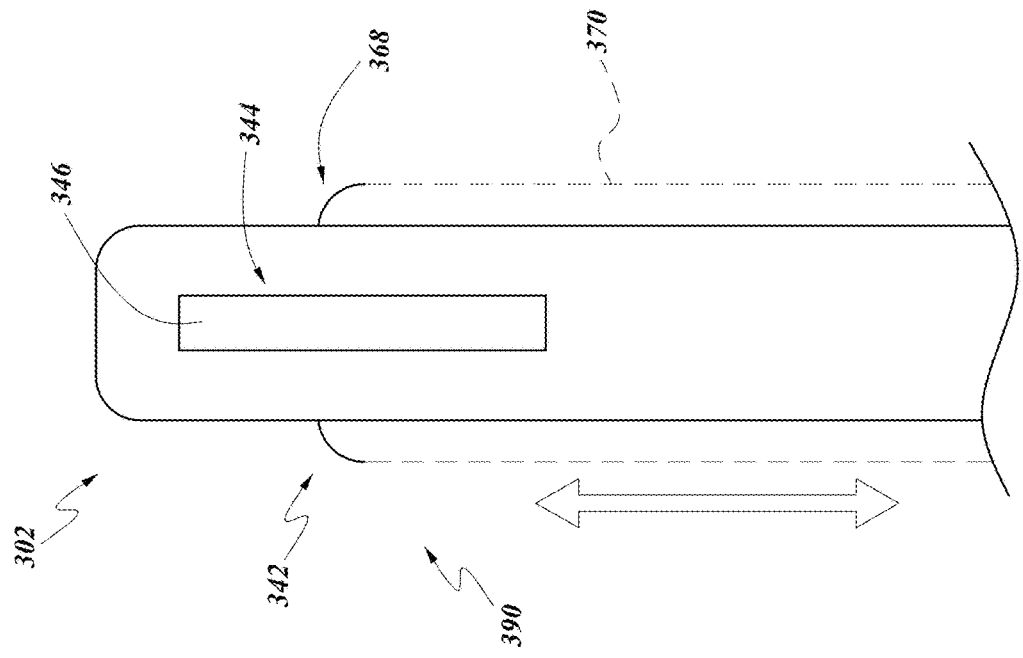

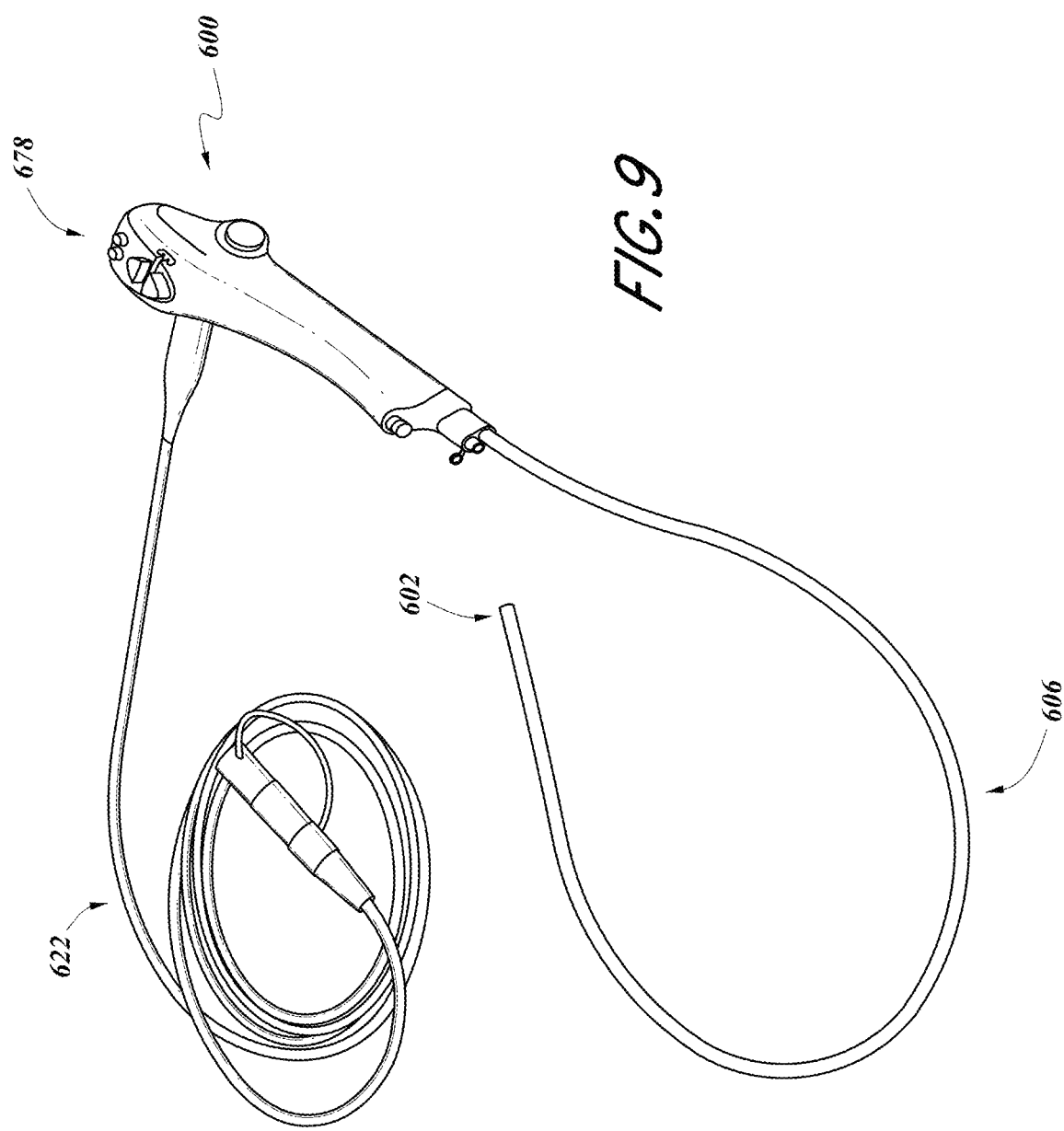

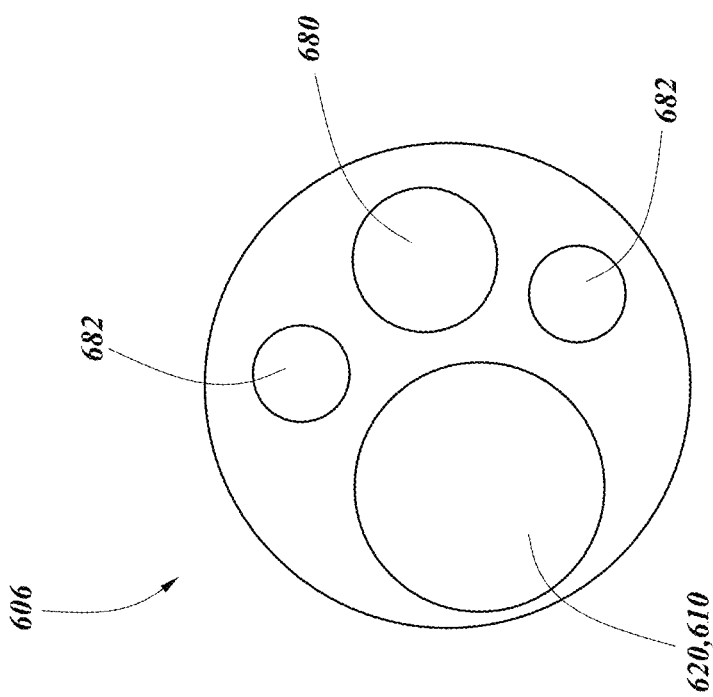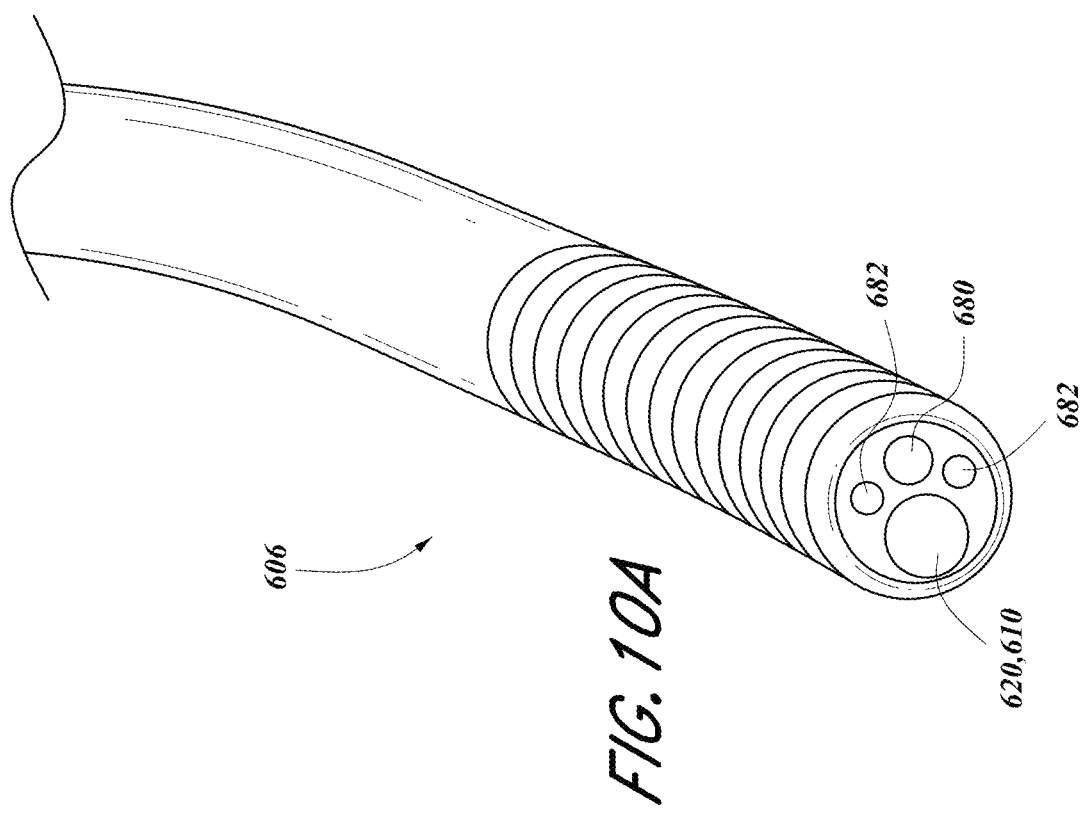

| Abdominal LES length in volunteers (functional length) | Number of volunteers | Decrease from assumed initial length of 3.5 cm (LES damage) |
|---|---|---|
| 1.0 – 1.5 cm | 6 | 2.0 – 2.5 cm |
| 1.5 – 2.0 cm | 10 | 1.5 – 2.0 cm |
| 2.0 – 2.5 cm | 17 | 1.0 – 1.5 cm |
| 2.5 – 3.0 cm | 11 | 0.5 – 1.0 cm |
| 3.0 – 3.5 cm | 5 | Zero – 0.5 cm |

FIG. 11A

| Rate of LES damage | At 25 years | At 35 years | At 45 years | At 55 years | At 65 years |
|---|---|---|---|---|---|
| 1 mm/decade | 34 mm | 33 mm | 32 mm | 31 mm | 30 mm |
| 2 mm/decade | 33 mm | 31 mm | 29 mm | 27 mm | 25 mm |
| 3 mm/decade | 32 mm | 29 mm | 26 mm | 23 mm | 20 mm |
| 4 mm/decade | 31 mm | 27 mm | 23 mm | 19 mm | 15 mm |
| 5 mm/decade | 30 mm | 25 mm | 20 mm | 15 mm | 10 mm |
| 6 mm/decade | 29 mm | 23 mm | 17 mm | 11 mm | 5 mm |
| 7 mm/decade | 28 mm | 21 mm | 14 mm | 7 mm | 0 mm |
| 8 mm/decade | 27 mm | 19 mm | 11 mm | 3 mm | 0 mm |
| 9 mm/decade | 26 mm | 17 mm | 8 mm | 0 mm | 0 mm |
| 10 mm/decade | 25 mm | 15 mm | 5 mm | 0 mm | 0 mm |

FIG. 12

| LES Shortening per Decade | Abdominal LES at age 15 | Abdominal LES at age 65 | Dilated Distal Esophagus | LES Incompetence | Symptoms | CLE | % in population |
|---|---|---|---|---|---|---|---|
| Zero | 35 mm | 35 mm | Zero | 0% | zero | No | < 0.01% |
| 1 mm | 35 mm | 30 mm | 5 mm | 0% | zero | No | 20% |
| 2 mm | 35 mm | 25 mm | 10 mm | 0% | zero | No | 30% |
| 3 mm | 35 mm | 20 mm | 15 mm | Post-prandial | Post-prandial | No | 20% |
| 4 mm | 35 mm | 15 mm | 20 mm | Post-prandial | GERD | No | 20% |
| 5 mm | 35 mm | 10 mm | 25 mm | At rest | Severe | +/− | 7% |
| 6 mm | 35 mm | 5 mm | 30 mm | Incessant | Severe | + | 3% |

FIG. 13

PATHOLOGIC ASSESSMENT OF LOWER ESOPHAGEAL SPHINCTER DAMAGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This Application claims priority benefit of U.S. Provisional Application No. 62/380,310, filed Aug. 26, 2016 and U.S. Provisional Application No. 62/320,189, filed Apr. 8, 2016, and the entirety of each is incorporated by reference.

FIELD

In general, the invention relates to methods and apparatuses for detecting and treating gastroesophageal reflux disease. In particular, the invention relates to methods and apparatuses including a method for determining and managing the progression of reflux disease and a biopsy device for the removal of mucosal tissue.

BACKGROUND

Gastroesophageal reflux disease ("GERD") is a common human disease that affects 30% of the adult population in the United States. It results from damage to the lower esophageal sphincter ("LES") which is a high pressure zone in the distal part of the esophagus that normally prevents reflux of gastric contents into the esophagus. Such a mechanism is necessary because there exists a pressure gradient from the stomach (which is at a baseline positive pressure of +5 mmHg, increasing with meals) to the esophagus (the thoracic part of which is at a baseline negative pressure of −5 mmHg). The high pressure of the LES is maintained by tonic contraction of the smooth muscle of the esophageal wall.

SUMMARY

The invention, in various aspects and embodiments, includes apparatuses, methods, and kits that can be used for analyzing mucosal tissue and determining and managing the progress of reflux disease in subject, including an asymptomatic person or patient with GERD. In some embodiments, the invention relates to all methods, whether histologic or non-histologic, and whether based on endoscopy or not, whereby the length of cardiac epithelium (with and without goblet and/or parietal cells) between the endoscopic gastroesophageal junction (the proximal limit of rugal folds) and the proximal limit of histologically defined gastric oxyntic epithelium can be measured.

In some embodiments, disclosed is a method of determining the progression of reflux disease in an esophagus of a patient. In some embodiments, the method can include identifying the location of an endoscopic gastroesophageal junction in the esophagus. In some embodiments, the method can include removing a length of tissue of the esophagus, wherein the length of tissue can include a portion of the endoscopic gastroesophageal junction. In some embodiments, the method can include identifying, using the length of tissue, the proximal limit of tissue containing cardiac epithelium. In some embodiments, the method can include determining the length of the squamo-oxyntic gap of the biopsied tissue by measuring the length of tissue extending between the proximal limit of tissue containing gastric oxyntic epithelium to the proximal limit of tissue containing cardiac epithelium. In some embodiments, the method can include determining a linear relationship comprising a slope of a line extending between a first data point and a second data point. In some embodiments, the first data point corresponds to a lower esophageal sphincter length of 35 mm and a first age. In some embodiments, the second data point corresponds to the difference of 35 mm and the length of the squamo-oxyntic gap and an age of the patient. In some embodiments, the method can include determining a target age of the patient when the lower esophageal sphincter will have a length less than or equal to 10 mm using the linear relationship.

In other embodiments, the length of the length of tissue can be in the range of 5 mm to 30 mm. In other embodiments, the length of cardiac epithelium proximal to gastric oxyntic epithelium (the squamo-oxyntic gap) can be measured using enhancements of optical imaging, including but not limited to one or more of magnification, high resolution focusing, narrow band imaging, or confocal endomicroscopy. In other embodiments, the width of the length of tissue can be in the range of 2 mm to 3 mm. In other embodiments, the thickness of the length of tissue can be in the range of 1 mm to 2 mm.

In other embodiments, the linear relationship can be further determined based upon the patient's health history. In other embodiments, the first data point corresponds to a lower esophageal sphincter length of 35 mm at the age of 10 if the patient has a history of childhood obesity, or a lower esophageal sphincter length of 35 mm at the age of 15 if the patient does not have a history of childhood obesity.

In other embodiments, identifying the endoscopic gastroesophageal junction can be accomplished using an endoscope. In other embodiments, identifying the endoscopic gastroesophageal junction can be accomplished using a trans-nasal endoscope.

In other embodiments, determining the length of the squamo-oxyntic gap can be accomplished using optical coherence tomography.

In other embodiments, determining the length of the squamo-oxyntic gap can be accomplished using chromoendoscopy. In other embodiments, the method can further include staining the epithelium of the esophagus with a dye.

In some embodiments, disclosed is a device configured to remove tissue from a patient. In some embodiments, the device can include a cannula having a proximal end, a distal end, and a wall extending between the proximal and distal ends, and a lumen extending from a proximal region near the proximal end towards a distal region near the distal end. In some embodiments, the device can include an opening in the wall in the distal region, wherein the opening can be in fluid communication with the lumen. In some embodiments, the device can include a connector in fluid communication with the lumen at the proximal region, wherein the connector can be adapted to be connected to a vacuum source. In some embodiments, the device can include a cutting member positioned near the opening and movable with respect to the opening.

In other embodiments, the device can include a biopsy portion removably attached to the cannula, wherein the biopsy portion can include the distal region. In other embodiments, the biopsy portion can include a proximal attachment portion and wherein the cannula can be configured to receive the proximal attachment portion of the biopsy portion. In other embodiments, the proximal attachment portion of the biopsy portion can include an external thread. In other embodiments, the device can include a removable pin configured to secure the biopsy portion to the cannula. In other embodiments, the device can include an o-ring configured to form a seal between the biopsy portion and the distal end of the cannula.

In other embodiments, the distal end of the biopsy portion can be sealed. In other embodiments, the distal region has a c-shaped cross-section. In other embodiments, the distal region can have an omega-shaped cross-section. In other embodiments, the device can include a vacuum. In other embodiments, the cutting member can be located external to the distal region. In other embodiments, the cutting member can be located within the cannula.

In other embodiments, the cutting member can include a blade. In other embodiments, the blade can be rectangular. In other embodiments, the blade can be cylindrical. In other embodiments, the blade can be semi-cylindrical.

In other embodiments, the device can include an actuator or a wire coupled to the cutting member, wherein the actuator or wire can be configured to move axially within the distal region. In other embodiments, the device can include an actuator or a wire coupled to the cutting member, wherein the actuator or wire can be configured to move axially adjacent to an outer surface of the distal region.

In other embodiments, the cutting member can be tubular with a circular cutting edge, the circular cutting edge configured to cut tissue extending within the opening. In other embodiments, the tubular cutting member can be disposed about the distal region. In other embodiments, the tubular cutting member can be disposed within the distal region.

In other embodiments, the cutting member can be tubular with an opening that can be aligned about the opening of the extraction structure, the cutting member configured to cut tissue extending within the opening. In other embodiments, the opening has a length along an axial length of the cannula of between 10 mm to 35 mm. In other embodiments, the opening has a width along a circumferential direction of the cannula of between and including 1 mm-2 mm, 2 mm-3 mm, 3 mm-4 mm, 4 mm-5 mm, 5 mm-6 mm, 6 mm-7 mm, 7 mm-8 mm, 8 mm-9 mm, and 9 mm-10 mm.

In other embodiments, the cutting member can include a plurality of blades. In other embodiments, the plurality of blades can be located along opposite sides of the opening. In other embodiments, the cutting member can be configured rotate circumferentially with respect to the opening. In other embodiments, the cutting member can be configured to cut the target tissue by extending the cutting member axially relative to the biopsy portion.

In other embodiments, the cutting member can include a cutting wire. In other embodiments, the device can be configured to be inserted through the working channel of an endoscope. In other embodiments, the device can include a device for visualizing the target tissue.

In some embodiments, disclosed is a method of determining the progression of reflux disease in an esophagus of a patient. In some embodiments, the method can include removing a length of tissue of the esophagus, wherein the length of tissue includes a portion of the endoscopic gastroesophageal junction. In some embodiments, the method can include determining an indication of damage to a lower esophageal sphincter. In some embodiments, the method can include determining when the lower esophageal sphincter will fail.

In some embodiments, disclosed is a method of determining the progression of reflux disease in an esophagus of a patient. In some embodiments, the method can include identifying the location of an endoscopic gastroesophageal junction in the esophagus. In some embodiments, the method can include removing a length of tissue of the esophagus, wherein the length of tissue includes a portion of the endoscopic gastroesophageal junction. In some embodiments, removing a length of tissue can be done using a device that includes a cannula having a proximal end, a distal end, and a wall extending between the proximal and distal ends, and a lumen extending from a proximal region near the proximal end towards a distal region near the distal end. In some embodiments, the device includes an opening in the wall in the distal region, wherein the opening is in fluid communication with the lumen. In some embodiments, the device includes a connector in fluid communication with the lumen at the proximal region, wherein the connector is adapted to be connected to a vacuum source. In some embodiments, the device includes a cutting member positioned near the opening and movable with respect to the opening. In some embodiments the method can include identifying, using the length of tissue, the proximal limit of tissue containing cardiac epithelium. In some embodiments, the method can include determining the length of the squamo-oxyntic gap of the biopsied tissue by measuring the length of tissue extending between the proximal limit of tissue containing gastric oxyntic epithelium to the proximal limit of tissue containing cardiac epithelium. In some embodiments, the method can include determining a linear relationship comprising a slope of a line extending between a first data point and a second data point. In some embodiments, the first data point corresponds to a first lower esophageal sphincter length and a first age. In some embodiments, the second data point corresponds to a second lower esophageal sphincter length and an age of the patient. In some embodiments, the method can include determining a target age of the patient when the lower esophageal sphincter will have a length less than or equal to 10 mm using the linear relationship.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIGS. 1A-1C illustrate the anatomy and histology of the esophagus and stomach in normal individuals and individuals with increasing severity of chronic reflux disease.

FIG. 5B illustrates a cross-sectional view of a distal end of an endoscope configured to receive an embodiment of a biopsy device.

FIGS. 6A-6D illustrate a distal end of an embodiment of a biopsy device.

FIGS. 7A-7D illustrate various views of an embodiment of an extraction structure located at a distal end of a biopsy tool that is configured to biopsy the mucosa tissue.

FIGS. 8C-8E illustrate various embodiments of a distal end of a biopsy tool with another embodiment of a cutting member.

FIG. 9 illustrates a top view of a trans-nasal endoscope that is configured to receive an embodiment of the biopsy device.

FIGS. 10A-10B illustrate various cross-sectional views of a distal end of a trans-nasal endoscope that is configured to receive an embodiment of the biopsy device.

FIGS. 11A-11C illustrate the results of a study of 50 volunteers measuring the distribution of abdominal LES length as measured by manometry (i.e., functional length).

FIG. 12 illustrates the impact of different rates of the progression of abdominal LES damaged on the residual length of the functional abdominal LES.

FIG. 13 illustrates the progression of the likely clinical features of GERD as predicted by the rate of progression of damage to the abdominal LES.

DETAILED DESCRIPTION

Background

Figures 2A, 2B:
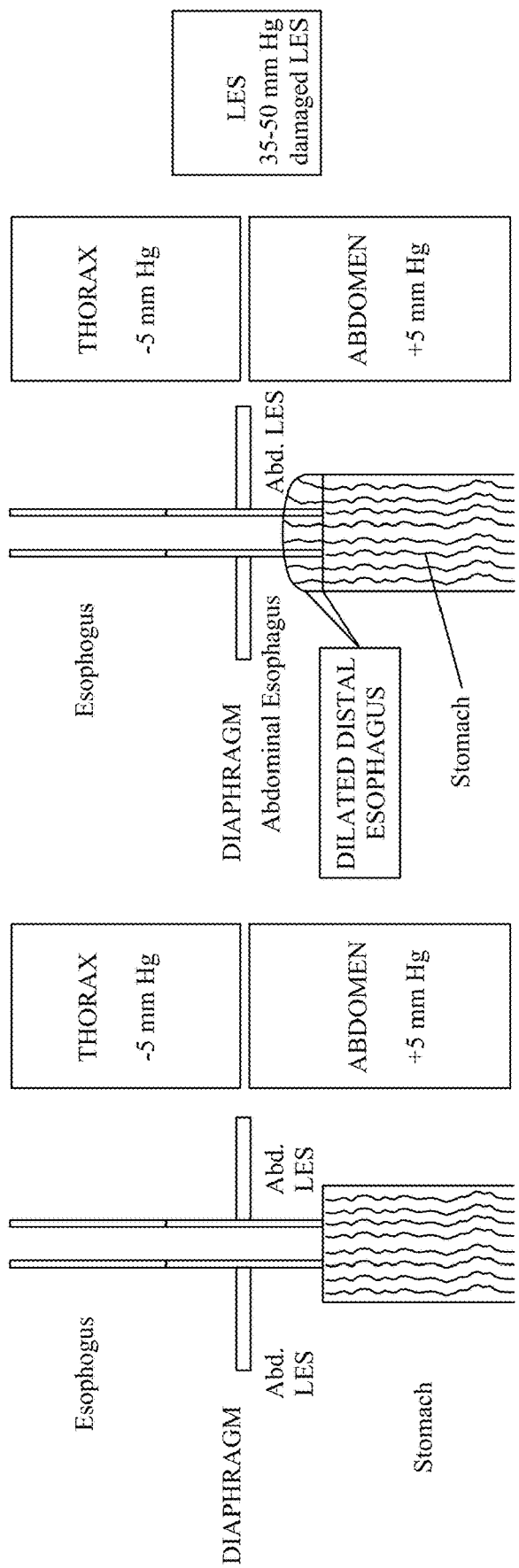
FIGS. 2A-2B illustrate the normal physiology of the lower esophageal sphincter and pathogenesis of the dilated distal esophagus.

The entire esophagus is lined by stratified squamous epithelium from its proximal cricopharyngeal end to its distal limit at the gastroesophageal junction. In the average person, the squamous epithelium is protected from exposure to gastric contents by the lower esophageal sphincter ("LES" or "sphincter").

The LES normally consists of a thoracic component above the diaphragm and an abdominal component below the diaphragm. The entire abdominal esophagus is the abdominal segment of the LES. The abdominal segment of the LES is critical to the function of the LES.

The cellular changes associated with GERD occur when the LES fails and allows reflux of gastric contents into the body of the esophagus. This causes the esophageal squamous epithelium in the thoracic esophagus to become exposed to gastric contents. Damage of esophageal squamous epithelium occurs when gastric contents come in contact with the esophagus as a result of transient sphincter relaxation or permanent sphincter destruction. Progressive permanent destruction of the sphincter is the primary cause and precondition of chronic gastroesophageal reflux disease. When the barrier of adequately high sphincter pressure is removed, reflux tends to occur because there is a pressure gradient from a positive pressure in the gastric lumen to a negative pressure in the intra-thoracic esophagus.

The basic cause of progressive permanent sphincter damage is gastric over-distension and increased intra-gastric pressure associated with heavy meals. Gastric over-distension puts pressure on the normal sphincter, causing it to shorten during heavy meals. As the sphincter is effaced, there is an effective downward movement of the squamo-columnar junction, causing the squamous epithelium to be progressively exposed to the environment of the stomach and thus the gastric juice.

One of the consequences of exposure of esophageal squamous epithelium to gastric juice is columnar metaplasia. This occurs early in the course of reflux disease, long before symptoms of GERD occur. This has been shown in experimental studies in asymptomatic volunteers. At the present level of understanding of GERD, however, these changes associated with permanent damage to the abdominal segment of the sphincter are not recognized as abnormal. Instead, they are misinterpreted as being normal proximal stomach.

Existing definitions of GERD and treatments of reflux disease are directed towards the control of symptoms and of erosive esophagitis. These can be the consequences of permanent damage of the sphincter to the point where it has failed. Symptoms and erosive esophagitis are largely the result of acute damage to the squamous epithelium caused by acid exposure. These acute squamous epithelial changes are reversible and largely curable with acid suppressive drug therapy. Exposure of the esophageal squamous epithelium in the body of the esophagus also can result in columnar metaplasia. This is called Barrett's esophagus. Acid suppressive drug therapy is not aimed at addressing the pathologic changes in metaplastic columnar epithelium. As a result, the pathologic changes in metaplastic columnar epithelium in the esophagus progresses despite present treatment, ultimately resulting in esophageal adenocarcinoma.

Management guidelines that single-mindedly emphasize acid neutralization and acid suppressive drug therapy to treat patients with reflux disease have been in place for five decades. The increasing effectiveness of acid suppression in this time frame has resulted in better control of symptoms, improved healing of erosive esophagitis, and prevention of chronic squamous epithelial complications such as deep intractable ulcers and strictures. Alkalinization of gastric contents is powerful in protecting and healing the esophageal squamous epithelium in a patient with reflux.

During the past five decades, however, there has been an explosion in the incidence of Barrett's esophagus and esophageal adenocarcinoma which are columnar epithelial complications of reflux disease. Recent studies have reported the dramatic overall increase in incidence of esophageal adenocarcinoma between 1973 (3.6 cases per million) and 2006 (25.6 cases per million), a seven-fold increase. Present management of GERD does nothing to address the incidence of esophageal adenocarcinoma.

The Lower Esophageal Sphincter

The lower esophageal sphincter ("LES") is a high-pressure zone that occupies the distal 5 cm of the esophagus, including the entire extent of the abdominal part of the esophagus. Competence of the sphincter depends on its resting pressure, total length, and abdominal length. In the normal person, the sphincter relaxes to permit normal swallowing and venting of intra-gastric gas, resulting in belching. Whenever the lower esophageal sphincter fails to function normally, either because of permanent damage or transient relaxation, the free reflux of gastric contents into the esophagus occurs as a result of intragastric pressure overcoming any residual sphincter function. Transient relaxation of the LES occurs increasingly with increasing permanent damage of the LES. The ultimate determinant of LES failure therefore is permanent LES damage.

The LES can be assessed by manometry. This can use one of several devices that have pressure sensors placed at intervals in the stomach, across the LES, and in the esophagus that continuously measures the pressures at 10 mm intervals. This produces a pressure diagram of the entire region. The proximal end of the LES is defined by the point where the pressure increases from baseline esophageal pressure by 2 mmHg. Similarly, the distal end of the LES is defined as the point where the LES pressure decreases by 2 mmHg to gastric baseline pressure. Manometry can provide data on the mean pressure in the LES, the overall length of the entire LES, and the length of the abdominal segment of the LES. The abdominal segment is that part of the LES from the diaphragm (defined manometrically as the respiratory inversion point where the pressure changes caused by breathing changes from thoracic to abdominal) to the distal end of the LES.

Length of Abdominal LES Associated with LES Failure

LES failure occurs when the abdominal LES length decreases to approximately less than 1 cm. This abdominal LES length can be used to define a defective LES. Manometry has no ability to measure LES damage. At this time, no criteria of manometric length of the abdominal LES greater than 1 cm can provide any diagnostic or prognostic relevance. There is no present method that can recognize LES damage. The disclosed pathologic method of assessing LES damage can be the first proposed test of LES damage.

Initial Length of the Abdominal LES

The initial length of the abdominal LES in any person is unknown. It is also unknown whether there is an individual variation in the length of the abdominal LES. Theoretically, people with a longer initial abdominal LES will be more resistant to develop LES failure because they have a greater reserve capacity.

Figure 11B:
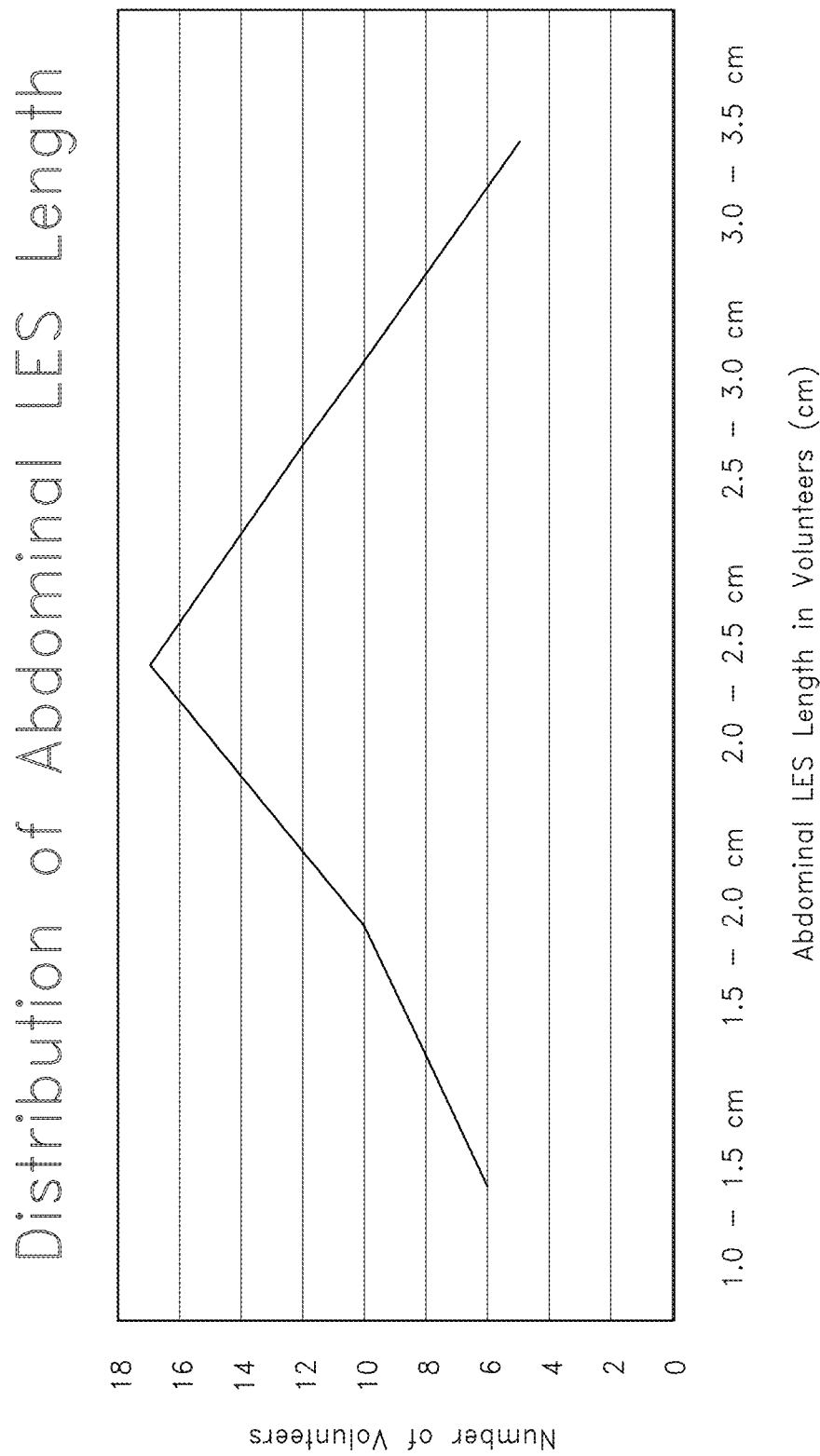
Figure 11C:
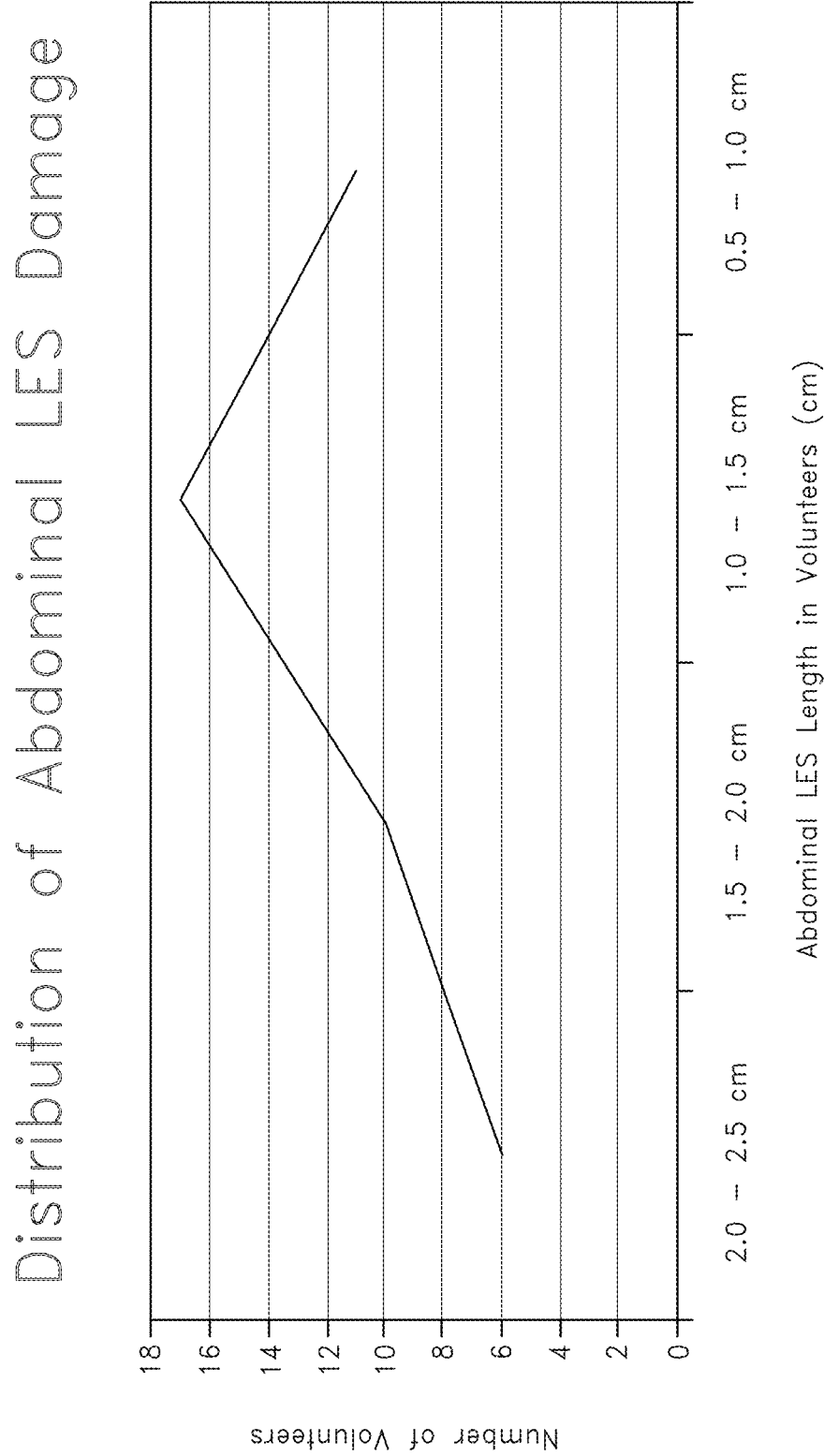

The variation in the initial length of the abdominal LES can be deduced by measuring its length in a large number of people asymptomatic for Gastroesophageal Reflux Disease ("GERD"). In a study of 50 volunteers, the distribution of abdominal LES length measured by manometry (i.e., functional length) is shown in FIG. 11A. As shown in FIG. 11A, the length of the abdominal LES in 48 volunteers (excluding one patient with greater than or equal to 5 cm and one with less than or equal to 1 cm) is divided into quintiles. When graphed, this curve has a substantially Gaussian distribution as illustrated in FIG. 11B-11C.

As shown above in FIG. 11B, there is a sharp upper limit at 3.5 cm with regard to the abdominal LES length in an individual asymptomatic for GERD with decreasing lengths to 1 cm. Because early LES damage can exist in this population without symptoms of GERD, the length of the abdominal LES between the initial length of the abdominal LES (3.5 cm) and the point at which it fails (less than or equal to 1 cm) represents the reserve capacity of the abdominal LES where it has undergone damage but has not become incompetent to a degree sufficient to cause reflux and therefore GERD symptoms.

If one assumes that the initial length of the abdominal LES is 3.5 cm in all people, the variation of abdominal LES represents a shortening of the LES length from its initial 3.5 cm. Given the aforementioned, the formula to determine the functional abdominal LES length of an individual can, in one embodiment, simplify to the following:

Functional abdominal LES length=3.5 cm−LES damage

Theoretically, by using this formula, and based on the measurement of the functional length, one may determine the severity of damage (e.g., the shortening) of the abdominal LES as illustrated in FIG. 11A and FIG. 11C.

However, the present manometric measurement of the abdominal LES is generally inaccurate, and in the absence of accurate data regarding the initial abdominal LES length, it is very difficult to assess LES damage exactly by manometry. Furthermore, it is unknown whether there is significant individual variation in the initial length of the abdominal LES. As a result, manometric assessment of the LES can provide no diagnostic criteria and is not used in the diagnosis of GERD.

Many physicians simply accept that the shortened (damaged) LES has disappeared into thin air. Furthermore, no one contemplates the consequences of LES damage. In fact, it is widely believed that the pathologic changes consequent to abdominal LES that is described herein (e.g., the dilated distal esophagus) represents the normal proximal stomach (gastric cardia).

The disclosed method of measuring the damaged abdominal LES by exact measurement using pathology can provide a new dimension of accuracy that will provide a diagnostic test and management tool for GERD not presently available.

Reflux Resulting from Intermittent Failure of the LES

Reflux from the stomach into the esophagus is a dynamic event. It can be likened to a jet of water issuing from a vertically held hose when the tap is opened. In a patient with a mildly incompetent sphincter and high-pressure gradient, reflux will have a jet-like form with a low volume and higher progression into the esophagus. With a severely incompetent sphincter and a low pressure gradient, the flow will be higher in volume with a lower retrograde propulsive force. The entry of gastric contents into the esophagus results in a response from the esophagus designed to clear the refluxed contents back into the stomach, e.g., by a stimulation of secondary peristalsis. The effectiveness of this clearing also varies, depending on the structural integrity of the esophageal muscle wall. Variations in the time of contact the refluxed molecules have with the esophageal epithelium.

Whatever the form of an episode of reflux, it creates a change in the volume, pH and/or pressure gradient in the esophagus. In the normal state, the esophagus is empty with an approximately neutral pH 7 to its end. The portion immediately beyond the distal end of the sphincter is highly acidic. In both the resting stomach and in the full stomach with its acid pocket, the pH immediately distal to the gastroesophageal junction is highly acidic with pH 1 to pH 2. The intra-gastric volume near the junction varies with the degree of gastric filling. When reflux occurs, a volume, pH, and/or pressure gradient is created in the esophagus as the refluxate is propelled upward. The exposure of the esophageal epithelium to every molecule in gastric juice during the reflux episode is highest in the most distal esophagus and lowest at the top of the column of refluxed material, where it is zero (the normal state of the esophagus). As a result, the pH gradient that is created has a baseline pH equal to gastric juice (approximately pH 1-2) in the distal most portion of the esophagus, increasing progressively to reach a neutral esophageal pH 7 at the height of the column. The amount of exposure of the esophageal epithelium to molecules in the refluxate is dependent on the volume of refluxed material and the efficiency of esophageal clearing, factors that are largely unmeasurable.

The lower esophageal sphincter is a physiological valve Like any valve, it maintains zero volume and pH 7 on the esophageal side and higher volume (which increases during gastric filling) and a strong acid pH on the gastric side. This valve function is achieved by both LES pressure and its length. Like any valve, the result of failure is an obliteration of these sharp gradients.

The Esophageal Squamous Epithelium

Squamous epithelium lining the normal esophagus is a nonkeratinizing stratified squamous epithelium. This consists of a basal layer of cells containing stem cells. Above this is a proliferative basal zone consisting of 2-3 layers of cells. In the normal steady state, the basal cell layer is less than 30% of the thickness of the epithelium. The proliferative cells undergo mitotic division to continually replace cells lost from the surface. A newly produced daughter cell in the proliferative zone is shed 4-6 days later at the surface.

The normal stratified squamous epithelium of the esophagus consists of cells that are bound to each other by tight cell junctions in the cell membranes. This results in an epithelium that is impermeable to molecules in the lumen. The surface epithelium is exposed to luminal molecules during swallowing and if the esophagus is exposed to gastric contents. One function of the normal squamous epithelium is to prevent entry of these luminal molecules into the epithelium. The squamous epithelium is therefore able to protect the deep proliferative zone and stem cells.

There are two epithelia in the normal person's upper digestive tract: normal stratified squamous in the esophagus and normal gastric oxyntic in the stomach. Normal gastric oxyntic mucosa is immune to damage by gastric contents. Esophageal squamous epithelium undergoes damage when exposed to gastric contents.

Definition of Normal Esophagus and Gastroesophageal Junction

An accurate definition of the gastroesophageal junction is critical in understanding the pathologic changes in the mucosa as a result of GERD. At present, the gastroesophageal junction is defined endoscopically as the proximal limit of the rugal folds and/or the end of the tubular esophagus. According to this definition, everything distal to the end of the tubular esophagus and/or the proximal limit of rugal folds represents stomach. As discussed above, a variable length distal to the end of the tubular esophagus is a dilated distal esophagus. The true gastroesophageal junction cannot be defined by endoscopy; it can only be defined by histology as the proximal limit of gastric oxyntic epithelium.

A reason for the error in the endoscopic definition of the gastroesophageal junction is a misunderstanding of the finding of cardiac epithelium distal to the endoscopic gastroesophageal junction. This is presently regarded as a normal epithelium lining the proximal stomach. However, this cardiac epithelium is not normal epithelium in the proximal stomach. Rather, it is a metaplastic epithelium resulting from damage to esophageal squamous epithelium caused by exposure to gastric contents. When cardiac metaplasia occurs in the abdominal esophagus, there is a concordant permanent damage of the LES.

Early damage to the squamous epithelium by exposure to gastric contents can result in columnar metaplasia. This can be associated with damage of the abdominal segment of the LES concordant with the length of columnar metaplasia. The abdominal esophagus that has lost LES pressure undergoes dilatation. The GERD-damaged dilated distal esophagus becomes a part of the gastric reservoir distal to the intact tubal esophagus, eventually developing rugal folds. The dilated distal esophagus has long been mistaken as the proximal stomach because it is distal to the proximal limit of rugal folds and the end of the tubular esophagus. As discussed above, the variable length of metaplastic columnar epithelium distal to the proximal limit of rugal folds and the end of the tubal esophagus contains esophageal submucosal glands, proving that this was dilated distal esophagus rather than proximal stomach.

In some embodiments, the true definition of the gastroesophageal junction is the proximal limit of gastric oxyntic mucosa, defined histologically. Because it is not possible to distinguish gastric oxyntic mucosa from metaplastic esophageal columnar epithelium in the dilated distal esophagus at endoscopy, it is also not possible to accurately define the true gastroesophageal junction at endoscopy. The junction between metaplastic cardiac epithelium and gastric oxyntic epithelium can only be recognized by histology. By presently recommended guidelines of interpreting endoscopy, the end of the esophagus is never visualized in biopsies. It is distal to the endoscopic GEJ by up to 3.5 cm.

The squamous epithelium normally extends to the end of the esophagus where it transitions to gastric oxyntic mucosa which lines the proximal stomach (FIGS. 1A-1C). This transition point is the true gastroesophageal junction.

FIGS. 1A-1C illustrate the anatomy and histology of the esophagus and stomach in normal and increasing severity of chronic reflux disease. In the normal patient, as illustrated in FIG. 1A, the esophagus is lined by squamous epithelium (reference letter "A") and the stomach is lined by gastric oxyntic mucosa with rugal folds (reference letter "E"). As can be seen, there is no separation of squamous and oxyntic mucosa. FIG. 1B illustrates a patient with mild LES damage (residual length of less than or equal to 3.5 to greater than or equal to 1 cm) within the reserve capacity of the LES. In this phase the LES is competent and there is no abnormal reflux into the esophagus. There are no symptoms of GERD and the thoracic esophagus is normal. This is the population described in FIGS. 11A-11C, above. As shown, the lower esophageal sphincter is shortened permanently which is concordant with a dilated distal esophagus that is lined by metaplastic columnar epithelium (shown here as three types: reference letter "B" illustrates intestinal metaplasia; reference letter "C" illustrates cardiac mucosa; and reference letter "D" illustrates oxyntocardiac mucosa). This dilated distal esophagus, being distal to the end of the tubular esophagus and proximal limit of rugal folds, is frequently mistaken as proximal stomach. FIG. 1C illustrates a patient with severe reflux disease. As shown, in severe reflux disease, the sphincter damage is greater, the dilated distal esophagus is larger, and there is damage, here shown as columnar metaplasia in the thoracic esophagus above the endoscopic gastroesophageal junction. This represents Barrett's esophagus. Damage to the squamous epithelium above the endoscopic gastroesophageal junction without columnar metaplasia causes symptoms of GERD and erosive esophagitis.

Histologically, there is no other type of epithelium between esophageal squamous epithelium and gastric oxyntic mucosa in the normal gastroesophageal junction, e.g., the squamo-oxyntic gap is normally "zero". In the normal state without any abdominal LES damage, the anatomical abdominal esophagus length can be determined by the following:

=length of the manometric undamaged abdominal LES; or

=length of the tubular abdominal esophagus; or

=length of squamous epithelium in the abdominal esophagus.

In healthy individuals, there will be no cardiac epithelium between the esophageal squamous and gastric oxyntic epithelia. As LES damage increases progressively, the length of cardiac epithelium in the gap between esophageal squamous epithelium and the proximal limit of gastric oxyntic epithelium increases to an amount that is equal to the length of LES that is damaged (e.g., shortened). In the abnormal state, for example, in the presence of abdominal LES damage of any extent, the formula changes to: The anatomical abdominal esophagus=

Manometric length of the damaged abdominal LES (=Length of the tubular abdominal esophagus=Length of squamous epithelium in the abdominal esophagus)+ Length of LES damage (=length of the dilated distal esophagus=length of cardiac epithelium in the squamo-oxyntic gap).

Many believe that cardiac epithelium normally exists between the esophageal squamous epithelium and gastric oxyntic epithelium. According to this widely held belief, normal people have approximately 1-4 mm of cardiac epithelium. There is evidence that increased lengths of cardiac epithelium distal to the endoscopic gastroesophageal junction (GEJ) are associated with GERD. However, such an understanding is incorrect as GERD cannot cause pathology in the stomach. The reason for this widely held belief is because the present definition of the GEJ is located at the end of the tubular esophagus or, when there is a hiatal hernia, the proximal limit of rugal folds. Because cardiac epithelium is found distal to the endoscopic GEJ, it is presently regarded as the proximal stomach.

However, contrary to widely held belief, the area distal to the endoscopic GEJ that is lined by cardiac epithelium is actually a distal esophagus that has dilated and developed rugal folds (as will be discussed in more detail below) as a result of normal LES pressure being lost due to damage. This portion of anatomy resulting from damage to the abdominal LES, will be termed the dilated distal esophagus.

An example of the dilated distal esophagus is illustrated in FIGS. 2A-2B. The area distal to the endoscopic GEJ that is lined by cardiac epithelium is associated with submucosal glands that are unique to the esophagus and not seen in the stomach. As will be discussed in more detail below, the length of the dilated distal esophagus correlates with severity of GERD. The length of the dilated distal esophagus can also correlate with damage (degree of shortening) of the abdominal segment of the LES. As illustrated in FIGS. 2A-2B, the abdominal esophagus loses its LES pressure and dilates in response to the pressures involved.

Reflux-Induced Damage to Esophageal Squamous Epithelium

Development of the Dilated Distal Esophagus

The earliest change in the pathogenesis of GERD involves progressively increasing damage to the most distal part of the lower esophageal sphincter. Loss of sphincter pressure in the distal abdominal esophagus brings its intraluminal pressure to that of all intra-abdominal organs and equal to the stomach, approximately +5 mm Hg.

This is a dilatory pressure that causes this part of the esophagus to distend when the stomach fills and when it does not have the protection of normal sphincter pressure. With time, the reflux-damaged abdominal esophagus dilates permanently, taking up the contour of the stomach. Studies conducted on the pathogenesis of GERD measured the diameter of the "gastric cardia" during surgery and showed that the diameter increased from a baseline of 6.3 cm in control patients to 8.9 cm in GERD patients and to 13.8 cm in patients with Barrett's esophagus.

With loss of sphincter function, the part of the distal esophagus that has lost its sphincter dilates and functions physiologically as the stomach. The dilated distal esophagus distends during meals and collapses when the stomach empties. This reservoir function causes it to develop rugal folds, a manifestation of all reservoir organs. The tubal esophagus shortens, and the angle of His becomes more obtuse, setting the stage for development of a sliding hiatal hernia. This earliest change of GERD is essentially the pathogenesis of the dilated distal esophagus. This is, in effect, reflux disease limited to the region of the lower esophageal sphincter (intrasphincteric reflux disease). In patients with no symptoms of GERD during life, a small (usually less than or equal to 1 cm) dilated distal esophagus is found at autopsy.

In some examples, as sphincter damage increases, the length of the dilated distal esophagus increases. The length of the squamo-oxyntic gap in the dilated distal esophagus is the best criterion for the degree of sphincter damage in the patient.

FIGS. 2A-2B and 3A-3B illustrate the normal physiology of the lower esophageal sphincter (LES) and pathogenesis of the dilated distal esophagus. As shown in FIG. 2A, the normal LES is approximately 5 cm long and straddles the diaphragm. The entire abdominal esophagus is covered by the abdominal segment of the LES that is approximately 3.5 cm long. Normally, the tonic muscle contraction maintains a resting pressure of 15 mm to 20 mm Hg that keeps the tubal shape of the abdominal esophagus. FIG. 2B then shows the progressive degradation of the abdominal segment of the LES damaged resulting from columnar metaplasia of the squamous lining of this part of the esophagus as it is exposed to gastric juice during gastric over-distension. LES damage means that the LES tone has disappeared; the functional LES has shortened. The dilated distal esophagus represents LES damage. The luminal pressure of this segment, which is the +5 mmHg pressure of abdominal organs, becomes dominant. As the stomach distends with every meal, so does this segment of the damaged abdominal esophagus. With time, this part of the esophagus dilates, takes up the contour of the stomach, and develops rugal folds (e.g., the dilated distal esophagus).

Structural Cellular Changes

Exposure of esophageal squamous epithelium to gastric contents can cause damage. In some embodiments, acid is the main cause of squamous epithelial damage while in other examples, a combination of acid and bile and/or pepsin can more potent in producing damage than acid alone.

The first change in the squamous epithelium induced by acid is likely to be intraepithelial edema, referred to as "dilated intercellular spaces" and an increase in the rate of loss of surface keratinocytes from the epithelium as a result of direct damage to the surface cells. This results in a more rapid turnover of the squamous cells. Increased surface loss stimulates the proliferative zone cells to increase in number as well as proliferative activity in order to maintain the structural integrity of the epithelium. This can be seen morphologically as an increased thickness of the basal cell zone of the epithelium to greater than 30% of epithelial thickness. This basal cell hyperplasia is associated with elongation of the papillary processes between the rete pegs; these papillary processes become highly vascularized.

Damage to superficial keratinocytes by acid can also result in the release of cytokines. These diffuse across the epithelium into the lamina propria where they have many potential effects. One of the potential effects is that many of these cytokines are chemo-attractive to eosinophil leukocytes which migrate into the epithelium, usually in small numbers. With severe damage to the epithelium, superficial erosions may occur in the epithelium and can progress to ulcers that involve the full thickness of the mucosa. Healing associated with these ulcers can induce fibrous strictures in the esophagus.

Existing Methods of Diagnosis in GERD

Presently, GERD is defined when troublesome symptoms arise. The existing diagnosis of GERD is entirely clinical without the requirement for confirmation by any diagnostic test at the onset of disease. Patients diagnosed with GERD clinically are treated empirically with proton pump inhibitors (PPI). Response to treatment confirms the diagnosis. This can frequently lead to significant over-use of PPI drugs.

The reason for this is that existing methods of diagnosing reflux disease are largely ineffective from a practical standpoint. For example, endoscopic examination of the squamous epithelium is relatively insensitive for the diagnosis of reflux disease. Hyperemia and gross erosions are used as the main diagnostic criteria. The extent of erosions has been used to classify erosive esophagitis into increasing grades of severity (A-D) in the Los Angeles classification. Unfortunately, erosive esophagitis is present in only a minority of patients with symptomatic reflux disease, making it a relatively insensitive endoscopic diagnostic criterion for GERD. The presence of erosions is also not specific for reflux disease; erosions may occur in many other esophageal diseases such as infections and pemphigus vulgaris. Patients with erosive esophagitis tend to have more complications and their symptoms are less easily controlled by medical therapy. Patients with clinical reflux disease who have no visible endoscopic abnormality fall into a designation of "non-erosive reflux disease" or NERD.

Similarly, using a biopsy to diagnose reflux esophagitis is not feasible because of low sensitivity and specificity. The microscopic changes of squamous epithelial damage represent the presently used criteria for the biopsy diagnosis of reflux disease. A combination of dilated intercellular spaces, basal cell hyperplasia with increased expression of Ki67 by immunoperoxidase staining, increased height of papillary ridges and the presence of intraepithelial eosinophils are histologic features that are associated with reflux esophagitis. Unfortunately, these morphologic changes in squamous epithelium are of little value in the practical diagnosis of reflux disease. All of these are relatively nonspecific general features of tissue injury rather than specific changes due to reflux. All of these can be seen in esophageal disease other than reflux, notably allergic (eosinophilic) esophagitis. These diagnostic criteria are also not very sensitive; approximately 50% of patients with symptomatic reflux will not have significant changes on biopsy of their squamous epithelium. Biopsy of the squamous epithelium has a very low predictive value for the diagnosis of reflux when positive histologic criteria are present. The absence of histologic criteria for reflux also has a very low predictive value for the absence of reflux. Therefore, in and of itself, biopsy of the squamous epithelium is therefore of little value in the evaluation of the patient with reflux disease.

Value of Columnar Metaplasia in the Diagnosis of GERD

The pathological changes that the squamous epithelium undergoes when it is exposed to acid in high enough concentration for a sufficient length of time is predictable when viewed from the perspective of columnar metaplasia.

The first visible morphologic change in the squamous epithelium upon exposure to acidic gastric contents is a separation of the squamous cells due to disruption of the tight junctions between the cells. This can be seen in an electron microscope as "dilated intercellular spaces" and as the earliest morphologic evidence of reflux. With increasing damage, the separation of the squamous cells increases and can easily be recognized by light microscopy in routine sections. The severity of the dilated intercellular spaces correlates with the severity of reflux.

The separation of squamous cells increases the permeability of the epithelium. As reflux-induced damage increases, the normally impervious epithelium becomes increasingly permeable. Luminal molecules of increasing size penetrate the squamous epithelium to an increasing depth. Increased infiltration of luminal molecules into the squamous epithelium has the potential to produce columnar metaplasia of the squamous epithelium in addition to morphologic injury.

Columnar Metaplasia.

Columnar metaplasia is caused by the entry of large molecules in the gastric juice into the esophageal squamous epithelium as a result of increased permeability. These large molecules, when they reach the proliferative and stem cell zone in the deeper part of the epithelium, can interact with cell surface receptors and have the potential to induce alterations in the genetic control mechanisms of the cells.

Cell surface and cytoplasmic receptors usually have complex tertiary structures that require complex complementary molecules for reaction. It is highly unlikely that receptors exist for simple particles like hydrogen ions (protons); acid is not a molecule that is likely to have the capability to cause cell receptor interactions that can result in genetic changes in the cell.

Columnar metaplasia of the esophagus results from the interaction of an unknown molecule in gastric contents that penetrates the damaged squamous epithelium, interacts with the basal region proliferative cells, and causes a switch in the genetic differentiating signal. This switch from the normal signal that dictates squamous differentiation to a new signal that includes BMP-4 (bone morphogenesis protein 4) induces columnar differentiation. The proliferating cell in the deep part of the squamous epithelium, under the BMP-4 signal, differentiates into a columnar epithelium. There is strong evidence that columnar metaplasia occurs early in the abdominal esophagus long before symptoms that define GERD arise in the individual.

Columnar metaplasia first occurs in the most distal esophagus. In a patient with a normal sphincter at the onset of this process, the progression of this change, which is caused by intermittent exposure of the abdominal esophageal squamous epithelium to gastric contents at time of gastric over-distension, can be extremely slow. This metaplastic columnar epithelium can slowly increase the separation of the esophageal squamous epithelium from the normal oxyntic mucosa that lines the proximal stomach, creating a histologic squamo-oxyntic gap. The presence of this metaplastic columnar epithelium and the gap can provide a marker for LES damage of increasing severity. With increasing reflux-induced damage of esophageal squamous epithelium, the amount of columnar metaplasia progressively increases and the squamo-oxyntic gap increases in length as the squamo-columnar junction (Z-line) moves cephalad. The length of the squamo-oxyntic gap is lowest in autopsy specimens in patients without a history of reflux disease during life. With increasing damage to the LES, the reserve capacity of the LES is eroded slowly. When LES damage eventually results in the abdominal LES decreasing to a length of less than or equal to 1 cm, the LES fails, abnormal reflux occurs and GERD becomes manifested clinically.

The exposure of the squamous epithelium in the thoracic esophagus to refluxed gastric contents goes through the same process. In some examples, microscopic damage with dilated intercellular spaces and increased permeability can cause erosive esophagitis which can cause columnar metaplasia. However, the exposure of the squamous epithelium in the thoracic esophagus can occur at a much more rapid rate when there is LES failure and abnormal reflux. The columnar metaplasia can now become visible at endoscopy in the thoracic esophagus as Barrett's esophagus (see FIG. 1C). This can be recognized as a premalignant change that is associated with increased risk of progression to adenocarcinoma.

In patients with chronic reflux disease, there are two epithelial types in the esophagus: normal squamous epithelium and metaplastic columnar epithelium. The extent (e.g., length) of the latter is directly proportional to the severity of cumulative life-long damage to the esophageal squamous epithelium by reflux. The response of these two epithelial types to gastric contents is different.

Effect of Acid Suppressive Drug Therapy on Squamous Epithelium

Suppressing gastric acid secretion is a highly effective method of treating squamous epithelial damage caused by reflux. In adequate dosage, proton pump inhibitors can maintain gastric pH above a pH of 4 for 12-14 hours of the day. At this level of alkalinization of gastric contents, the most potent molecule in the offensive agent in the causation of reflux damage of the squamous epithelium is effectively neutralized.

The most reliably reproducible effect of effective acid suppression in patients with reflux disease is healing of erosive esophagitis in over 90% of patients, usually within a month of initiation of therapy. Continued acid suppression also prevents recurrence of erosive esophagitis, prevents progression of erosions to deeper ulcers, and markedly decreases the incidence of complex strictures of the esophagus. The practical effect of this change has been obvious; deep and intractable ulcers and fibrous strictures of the esophagus have become rare complications of GERD.

The second positive effect of alkalinizing gastric contents with proton pump inhibitors is that it controls pain. Heartburn is reduced significantly in most patients because suppression of acid removes the most potent stimulator of pain-sensitive nerve endings.

However, acid suppression does not completely eradicate pain in many patients with reflux as proton pump inhibitor therapy does not actually stop or decrease reflux. Patients on PPIs continue to have reflux at the same frequency as before and the squamous epithelium is exposed to all the molecules in the refluxate except for acid. In many patients whose symptoms persist despite adequate dosage of acid suppressive drugs, the continuing "weak-acid (pH 4-6)" reflux can still cause pain.

Effective control of pain in patients with reflux disease is probably most dependent on restoring the normal impermeable state of the squamous epithelium. It is only when this is achieved that the refluxed material in the lumen of the esophagus is kept completely away from the pain-sensitive nerve endings in the esophagus. The fact that some pain and discomfort frequently occurs despite acid suppression can be explained if the squamous epithelial permeability is not fully reversed. Non-acid molecules in the refluxate can also penetrate the epithelium and stimulate nerve endings to cause pain.

While this may be at a lower level than acid-induced pain that was present before treatment was instituted, it is often still a source of significant discomfort. Acid suppressive drug therapy is only directed towards the acid in the offensive mixture of reflux disease. It does not address the fact that other molecules in the refluxate may continue to cause both symptoms and pathologic changes in the esophageal epithelium. It also does not correct or improve the damaged lower esophageal sphincter or decrease the number or frequency of reflux events. Studies of patients treated with acid suppressive drug therapy shows that certain elements of reflux disease remain poorly controlled: symptoms resulting from exposure of the epithelium to weak-acid reflux, regurgitation, and the progression of pathologic changes in the metaplastic columnar epithelium.

Effect of Acid Suppressive Drug Therapy on Metaplastic Esophageal Columnar Epithelium Gastroesophageal reflux disease has changed in character over the past six decades. In the 1950s, reflux disease was defined almost entirely by its effects on squamous epithelium. The inability to control pain, ulceration, and strictures were the main problems. Approaches to address these issues previously require esophagectomy. The pharmaceutical industry subsequently stepped up to the plate, developing increasingly potent drugs to control acid secretion, which have proved to be highly successful in controlling pain, ulcers, and strictures.

Columnar metaplasia of the esophagus was common in the 1950s. Examination of detailed descriptions of columnar lined esophagus showed that many patients had extremely long segments of columnar lined esophagus.

However, the last six decades has shown an explosion in the incidence of intestinal metaplasia and adenocarcinoma within the columnar lined esophagus. In the 1950s, histologic descriptions of the epithelium showed that intestinal metaplasia containing goblet cells was very uncommon even in very long segments of columnar lined esophagus. Adenocarcinoma was so rare that single cases were reported. However, the increase in the prevalence of intestinal metaplasia in the population from 1950 to 2012 has been dramatic. Today, Barrett's esophagus (i.e. intestinal metaplasia in a biopsy taken from visible columnar lined esophagus) is present in an estimated 5-10% of adults in the population. If symptomatic patients with normal endoscopy are biopsied, intestinal metaplasia is found in up to 25% of patients in some studies.

Barrett's esophagus and esophageal adenocarcinoma are solely the result of gastroesophageal reflux disease. There is no other cause for either of these entities despite some associations with obesity and smoking. Unfortunately, there has been little or no attempt to address this problem by the medical community at large. The treatment of reflux disease is still aimed at controlling heartburn and healing erosive esophagitis with acid suppressive drugs. While this goal has been met and the medical community declares self-satisfied success at the wonder of their drugs and their ability to control reflux disease and improve quality of life, the number of people dying from cancer that is the complication of reflux disease is increasing exponentially.

The goal of treatment of a disease should be to prevent death at all costs; everything else is secondary. Existing treatments for reflux disease have as their goal the improvement of the quality of life of millions of people who have heartburn caused by reflux. However, this is merely the treatment of the squamous manifestations of the disease when the development of cancer is in fact a disease of the columnar metaplastic epithelium.

Metaplastic Esophageal Columnar Epithelial Types

The change in the differentiating genetic signal from the postulated Wnt to BMP-4 in the proliferating cells of the esophageal epithelium can result in the transformation of the stratified squamous epithelium to a columnar epithelium composed entirely of undifferentiated mucous cells. These cells line the surface and form a foveolar pit and glands, all composed of morphologically similar mucous cells. This is cardiac epithelium which is defined as an epithelium composed entirely of mucous cells without parietal or goblet cells. Cardiac epithelium has also been called "junctional epithelium" and "mucous-cell only epithelium."

Figure 4:
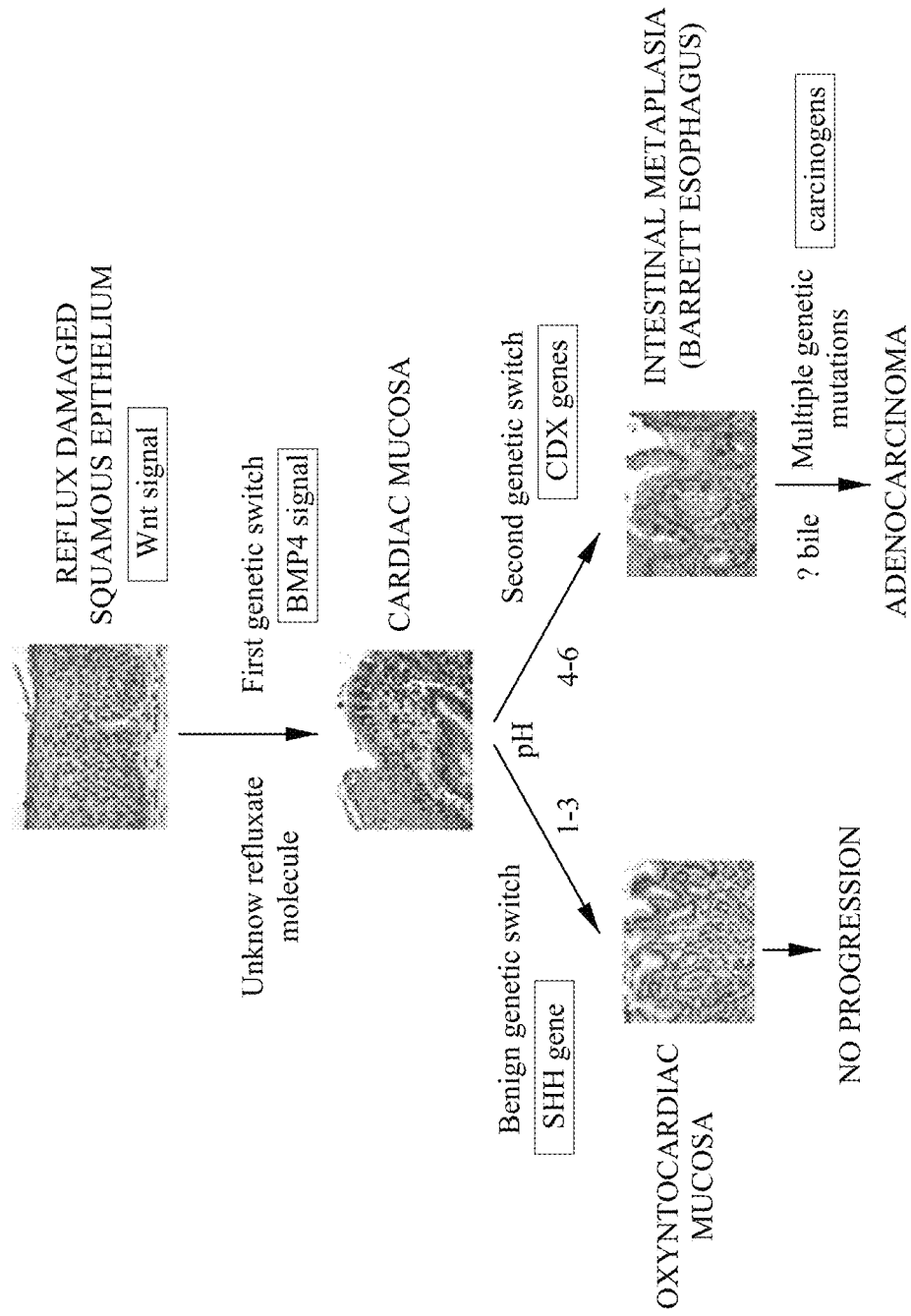
FIG. 4 is a flow chart illustrating the sequence of epithelial changes in the esophagus caused by reflux disease.

Cardiac epithelium in the esophagus is subjected to attack by gastric contents as a result of exposure to gastric contents. As a result, it has the potential to evolve into two other significant epithelial types within the columnar lined esophagus—oxyntocardiac and intestinal epithelia. These are defined by the presence of parietal cells and goblet cells. FIG. 4 illustrates the sequence of epithelial changes in the esophagus caused by reflux disease. As an initial step, the squamous epithelium undergoes columnar metaplasia to cardiac mucosa. As will be discussed in more detail below, the cardiac mucosa can then evolve in one of two directions: (a) in a strong acid, a Sonic Hedgehog gene in the cardiac mucosa is activated which leads to parietal cells and oxyntocardiac mucosa. This is a stable epithelium that does not progress to cancer; (b) in a weaker acid, CDX2 is activated and intestinal metaplasia results.

As illustrated in FIG. 4, the first type of change in cardiac mucosa occurs as a result of development of parietal (oxyntic) cells within its glands. The presence of parietal cells in cardiac mucosa converts the epithelium to oxyntocardiac epithelium. This corresponds to columnar epithelium where the glands contain a mixture of mucous cells and parietal cells. It does not have goblet cells. Like the cardiac metaplasia of squamous epithelium resulted from a genetic switch, oxyntocardiac mucosa is generated in cardiac mucosa by activation of a different differentiating genetic signal—possibly a combination of BMP-4 and the Sonic Hedgehog gene. Sonic Hedgehog gene is the usual genetic signal in the gastric oxyntic mucosa and is required for development of parietal cells in gastrointestinal columnar epithelia. Oxyntocardiac epithelium has also been called "gastric fundic-type epithelium" and "mixed mucous and parietal cell epithelium."

The second type of change in cardiac epithelium can occur as a result of development of goblet cells which can appear in the surface, foveolar region, or in the glands. As shown in FIG. 4, this is intestinal metaplastic epithelium. Intestinal epithelium can be generated in cardiac mucosa by activation of yet another different differentiating genetic signal—the homeobox gene complex that includes CDX2. CDX2 is the usual genetic signal in the intestine with CDX2 being dominant for colonic differentiation. Intestinal epithelium in the esophagus has also been called "specialized columnar epithelium" or "Barrett's esophagus."

These three columnar epithelia are the only significant columnar epithelial types that occur in the esophagus. Based on the presence or absence of three easily recognizable cell types: mucous cells, parietal cells, and goblet cells, the identification of the type of columnar epithelia cells in biopsies can be precise and accurate with little inter-observer variation after minimal training. Because this process requires two steps (damage to squamous epithelium with increased permeability and a cellular reaction between molecules in gastric contents and esophageal epithelium that produces highly specific changes in differentiating genetic signals), the presence of any or all these epithelia provide a diagnostic marker for squamous epithelial damage caused by exposure to gastric contents.

Diagnostic Method and Management of GERD

At a cellular level, reflux disease can be defined as the presence of a gap between esophageal squamous epithelium and gastric oxyntic mucosa composed of any combination of cardiac, oxyntocardiac and intestinal epithelia. This gap is called the squamo-oxyntic gap. This definition is specific for reflux disease as columnar metaplasia does not occur in any other esophageal disease.

Metaplastic Columnar Epithelium in the Dilated Distal Esophagus

From its normal length of zero cm, the length of metaplastic columnar epithelium progressively increases in length in patients due to damage caused in esophageal squamous epithelium by exposure to gastric contents during gastric over-distension. Columnar metaplasia is usually a "permanent" change. As such, it changes in only one direction—increase in length.

There is a variation in the length of metaplastic columnar epithelium in the dilated distal esophagus. In autopsy studies of people who have died without symptoms of reflux disease during life, the squamo-oxyntic gap varies from zero to less than 1 cm. Based on the length of metaplastic columnar epithelium in the dilated distal esophagus, which is a measure of damage of the abdominal segment of the LES, the following stages in the progression of GERD can be defined.

Stage 0: Normal: This is defined by the absence of any metaplastic columnar epithelium between the esophageal squamous epithelium and gastric oxyntic epithelium. The patient has zero LES damage. The functional abdominal LES length is the original 3.5 cm.

Stage 1: Compensated LES damage: This is defined as the presence of metaplastic columnar epithelium in the dilated distal esophagus of a length greater than or equal to zero and less than or equal to 1.5 cm. The residual functional abdominal LES length varies from less than or equal to 3.5 cm to greater than or equal to 2.0 cm. The LES maintains its competence at all times and the patient has no reflux into the thoracic esophagus.

The limit of the stage of compensated damage is selected as less than or equal to 1.5 cm of LES damage because of what happens to the LES during a heavy meal. A person with less than or equal to 1.5 cm of LES damage will have a residual fasting abdominal LES of greater than or equal to 2.0 cm. As described in the pathogenesis of LES damage, over-distension of the stomach during a heavy meal causes a temporary dynamic shortening of the abdominal LES. This is usually 0.5 to 1.0 cm. In this compensated LES stage, during the postprandial phase of a heavy meal, the abdominal LES that has a functional fasting length of greater than or equal to 2.0 cm can shorten by an additional 1.0 cm, bringing the functional abdominal LES length close to but not reaching the less than or equal to 1.0 cm at which LES failure occurs.

Stage 2: Mild (Early) GERD: This is defined as the presence of metaplastic columnar epithelium in the dilated distal esophagus of a length of 1.5 to less than or equal to 2.5 cm. This means a fasting length of abdominal LES of 2.0 to greater than or equal to 1.0 cm. In such persons, the LES is competent when the stomach is empty. However, when dynamic shortening occurs during a heavy meal, the abdominal LES length can decrease to less than or equal to 1.0 cm, leading to LES failure and reflux. The likelihood of LES failure during or after a meal increases progressively as abdominal LES length decreases from 2.0 to 1.0 cm within this stage. This is early symptomatic GERD manifested as symptoms limited to the postprandial period. Their reflux is usually mild and controllable with PPI therapy.

Stage 3: Severe (advanced) GERD: This is defined as the presence of metaplastic columnar epithelium in the dilated distal esophagus of a length of 2.5 cm or more. The patients residual abdominal LES is 1.0 cm or less. This is a sphincter that fails at rest with numerous reflux episodes per day. Patients with this degree of LES damage are likely to fail to be controlled with PPI therapy, have severe erosive esophagitis, and visible columnar metaplasia in the thoracic esophagus. They are at risk for Barrett's esophagus and progression to adenocarcinoma.

The above described system permits recognition of an individual's LES status at the time of the assessment. Because LES damage correlates with the occurrence of LES failure and reflux, the system can be a powerful new diagnostic test for GERD and tool for disease management.

For example, it is capable of evaluating a person who has symptoms that may or may not be caused by GERD. At the present time, the lack of ability to exclude GERD by any diagnostic test results in these people being given empiric PPI therapy. If this resolves symptoms, they are maintained on such therapy in the long term, sometimes unnecessarily. With the new assessment, if the patient has LES damage less than or equal to 15 mm, it is unlikely that GERD is the cause of symptoms.

The measurement of LES damage can help to objectively establish the severity of GERD and provide a valuable tool for disease management.

Distribution of Columnar Epithelia in the Squamo-Oxyntic Gap

The three types of columnar epithelium in the squamo-oxyntic gap show infinite variation. Oxyntocardiac epithelium is present in all people. At autopsy in people without reflux and in patients with an oxyntic gap of less than 1 cm, oxyntocardiac epithelium is often the only columnar epithelium in the gap. In patients with an oxyntic gap that is 1-2 cm, cardiac epithelium is almost always present in the gap.

Intestinal metaplasia is present in the squamo-oxyntic gap in a minority of patients. The prevalence of intestinal metaplasia varies with the length of the squamo-oxyntic gap; the longer the gap, the greater the prevalence of intestinal metaplasia. In the new millennium, intestinal metaplasia is present in 90% of patients with a gap exceeding 3 cm and 100% of patients when the gap exceeds 5 cm. In general, risk of esophageal adenocarcinoma is limited to patients who develop intestinal metaplasia in the metaplastic columnar epithelium. As such, the risk increases with increasing length of GERD. The major recognized risk factor for esophageal adenocarcinoma is the presence of intestinal metaplasia in columnar epithelium in the thoracic esophagus above the endoscopic gastroesophageal junction. While a risk of adenocarcinoma may exist in patients with intestinal metaplasia limited to the dilated distal esophagus, this is unproven and, if it exists, the risk is likely to be very low.

Mapping studies of the squamo-oxyntic gap shows that the three epithelia are distributed in a remarkably nonrandom and constant manner. Oxyntocardiac epithelium dominates the distal part of the gap. If intestinal metaplasia is present, it is almost always present in the most proximal region of the gap immediately adjacent to the squamo-columnar junction. When present, the amount of intestinal metaplasia varies greatly in different patients. In some patients intestinal metaplasia is limited to the most proximal region of the gap; in others, the intestinal metaplasia extends distally to involve an increasing part of the gap. The involvement is usually contiguous without skip areas. In a few patients, intestinal metaplasia is present in the entire gap but there is usually non-intestinalized cardiac and oxyntocardiac mucosa in the most distal part of the gap separating intestinal from gastric oxyntic mucosa.

Progression of LES and Damage with Time

LES damage is a progressive change. Progression occurs only in one direction, (for example, increasing LES damage). Damage begins at the true gastroesophageal junction and slowly extends proximally (e.g., upward, towards the subject's mouth) and is marked by columnar metaplasia of esophageal squamous epithelium. Progression of LES damage can therefore be measured from the true gastroesophageal junction (proximal limit of gastric oxyntic epithelium) to the distal limit of squamous epithelium. Once it has occurred, LES damage never reverses. No therapy can cause the LES to return to its normal function.

Abdominal LES damage in the early stages that have been described above is caused by intermittent exposure of esophageal squamous epithelium to gastric contents during periods of gastric over-distension. LES damage is therefore a manifestation of chronic over-eating. GERD can have a strong association with obesity.

Once LES damage begins, there is evidence that its progression is linear. Such a model assumes that, once established, a person maintains a similar eating pattern over the long term. A study of three groups of persons with increasing severity of GERD—"normal", "non-hernia GERD" and "hernia-GERD" demonstrated that the baseline length of the LES decreased in increments of approximately 0.8-1.0 cm in the three groups. The study demonstrated that LES damage was greatest in patients with hernia-GERD, intermediate in non-hernia GERD and least in "normal." When air was insufflated into the stomach to produce gastric distension, there was a dynamic shortening of the LES. The amount of shortening was very similar in the three groups (for example, the lines of shortening were essentially parallel). This suggests that gastric over-distension produces the same effect irrespective of the patient's residual LES length. There is no vicious cycle change where LES damage increases the dynamic shortening resulting from gastric over-distension.

As long as a person's eating habits remain constant, the above information suggests that progression of LES damage will be linear.

The abdominal LES is approximately 35 mm at full development. Therefore, in some embodiments, the maximum length of 35 mm can be used as the baseline length from which LES damage begins. In other embodiments, the baseline length is determined based upon a characteristic of the individual being analyzed. For example, the baseline length may be selected based upon one or more of the age, height, weight, medical history, family history, or other characteristic of the individual. In some embodiments, the baseline length is between 20 and 50 mm, such as 20 mm, 25 mm, 30 mm, 35 mm, 40 mm or 50 mm.

In some embodiments, it is assumed that the age of a 15 years old is the average age at which people reach their full height and therefore approximately the age at which the abdominal LES reaches its maximum length. It can be assumed that this would be a reasonable age at which an individual's lifelong eating habits are established. In other embodiments, a different age is selected as the first age value. For example, a first age value may be selected based upon different patient populations, geographical locations, medical histories, family histories, etc. In people who have a history of childhood obesity, over-eating can be assumed to have begun at an earlier age.

As noted above, the abdominal LES begins at the true junction between the esophagus (lined by squamous epithelium) and the stomach (lined by gastric oxyntic epithelium). Before damage has occurred in the esophagus, the normal squamo-oxyntic gap is zero. Damage to the abdominal LES—e.g., the development of cardiac epithelium from esophageal squamous epithelium—begins where the esophagus ends, which is where the stomach begins. This point is marked histologically by the proximal limit of gastric oxyntic epithelium whose position does not change.

Generally, abdominal LES damage is caused by gastric distention caused by overeating. As noted above, it is manifested as cardiac epithelium inserted between the squamous epithelium and gastric oxyntic epithelium. This squamo-oxyntic gap represents the damage to the abdominal LES. This squamo-oxyntic gap slowly increases in length over decades of over-eating which causes cardiac metaplasia (and therefore LES damage). Damage to the abdominal LES causes the esophagus to dilate, thereby forming the dilated distal esophagus. In some embodiments, the length of the damage to the abdominal LES (i.e. the squamo-oxyntic gap) is equivalent to the length of the dilated distal esophagus, measured as the length of metaplastic columnar epithelium between gastric oxyntic epithelium and the distal limit of squamous epithelium.

In some embodiments, damage to the abdominal LES progresses at a different rate in different people. FIG. 12 illustrates the impact of different rates of progression of abdominal LES damage, expressed in mm/decade, on the residual length of the functional abdominal LES. As shown, patients progress to the various stages of LES damaged described above at varying ages in their lives. Patients with 3 mm or less/decade LES damage will maintain a competent LES to age 65 years. This represents 70% of the population. By contrast, patients with higher rates of LES damage will progress to various severities of GERD and adenocarcinoma risk at increasingly younger ages.

As illustrated above, changes with age of the functional residual length of the abdominal LES assuming that the original length at maturity is 35 mm, that LES damage begins at age 15 years (or other first age) and that LES damage has a linear progression over the long term. The abdominal LES lengths shaded in light gray represent lengths at which the LES is likely to be competent. The LES length shaded in gray represent an LES that is susceptible to failure with gastric distension (for example, at risk of post-prandial reflux). The lengths in dark gray represent an LES that is below the length at which LES failure occurs at rest.

FIG. 13 below illustrates the progression of the likely clinical features of GERD as predicted by the rate of progression of damage to the abdominal LES (as measured by the formation of the dilated distal esophagus). Although the table in FIG. 13 illustrates data points for individual experiencing zero LES shortening/decade, 1 mm LES shortening/decade, 2 mm LES shortening/decade, 3 mm LES shortening/decade, 4 mm LES shortening/decade, 5 mm LES shortening/decade, and 6 mm LES shortening/decade, FIG. 13 is not intended to be limiting but as an illustrative example of the effect on the esophagus as the rate of LES shortening per decade increases. In some examples, patients experiences a rate of LES shortening per decade between any of the points listed in the table (e.g. 0 mm-1 mm; 1 mm-2 mm, 2 mm-3 mm, 3 mm-4 mm, 4 mm-5 mm, and 5 mm-6 mm) will exhibit a result that is consistent with the trend provided in FIG. 13.

As noted above, in some examples, the abdominal LES is assumed to have an initial length of 35 mm at the age of 15 when fully formed. A different initial length may be selected based upon other criteria, such as those discussed above. In some embodiments, it is assumed that the abdominal LES will be incompetent, cause reflux (and the patient will begin exhibiting symptoms of GERD) when the abdominal LES is less than 10 mm in length, first in the postprandial phase after a heavy meal and then in the fasting state. The basis for the occurrence of postprandial reflux is that a heavy meal can cause dynamic (temporary) LES shortening of between 5 mm-10 mm.

As shown in FIG. 13, an individual who experiences no rate of LES shortening will have no change in abdominal LES between the ages of 15 and 65. Such an individual makes up less than 0.01% of the general population and have a dilated distal esophagus (a squamo-oxyntic gap) of zero cm. As the abdominal LES is not damaged, at age 65, the patient will not experience any LES incompetence and will exhibit no symptoms associated with reflux disease. Without any reflux, there will be no visible columnar epithelium in the thoracic esophagus. This person is not at risk for adenocarcinoma.

Turning next to an individual who experiences a rate of LES shortening of 1 mm, such an individual will experience, over 5 decades, approximately 5 mm change in abdominal LES between the ages of 15 and 65. Such an individual makes up approximately 20% of the general population and will have a dilated distal esophagus (a squamo-oxyntic gap) of 5 mm. Because the length of the abdominal LES is greater than the threshold required to protect the esophagus from the acid contents of the stomach after a meal (approximately 5-10 mm), the patient will not experience any LES incompetence at age 65 and will therefore exhibit no symptoms associated with reflux disease. Without any reflux, there will be no visible columnar epithelium in the thoracic esophagus. This person is not at risk for adenocarcinoma.

In some examples, an individual experiencing a rate of LES shortening of 2 mm, will experience, over 5 decades, an approximately 10 mm reduction in abdominal LES between the ages of 15 and 65. Such an individual makes up approximately 30% of the general population and will have a dilated distal esophagus (a squamo-oxyntic gap) of 10 mm. Because the length of the abdominal LES is greater than the threshold required to protect the esophagus from the acid contents of the acid contents of the stomach after a meal (approximately 5-10 mm), at age 65, the patient will not experience any LES incompetence and will therefore exhibit no symptoms associated with reflux disease. Without any reflux, there will be no visible columnar epithelium in the thoracic esophagus. This person is not at risk for adenocarcinoma.

In some embodiments, an individual experiencing a rate of LES shortening of 3 mm, will have, over 5 decades, an approximately 15 mm reduction in abdominal LES between the age of 15 and 65. Such an individual makes up approximately 30% of the general population and will have a dilated distal esophagus (a squamo-oxyntic gap) of 15 mm. With a 15 mm reduction in abdominal LES, the individual would be left with an abdominal LES of 20 mm at the age of 65. As noted above, a heavy meal can frequently cause dynamic (temporary) LES shortening of between 5-10 mm. Therefore, an individual with an abdominal LES of 20 mm at the age of 65 could experience LES incompetence and exhibit symptoms associated with reflux disease after a meal (post-prandial). With only minimal intermittent reflux, the probability of visible columnar epithelium in the thoracic esophagus is low. Except for rare individuals who develop visible columnar lined esophagus, the individuals in this group are not at risk for adenocarcinoma.

In individuals experiencing a rate of LES shortening of 4 mm, the individual will have approximately a 20 mm reduction in abdominal LES in the 5 (five) decades between the ages of 15 and 65. Such an individual makes up approximately 20% of the general population and will have a dilated distal esophagus (a squamo-oxyntic gap) of 20 mm at the age of 65. With a 20 mm reduction in abdominal LES, the individual will be left with an abdominal LES of 15 mm at the age of 65. As noted above, a heavy meal can frequently cause dynamic (temporary) LES shortening of between 5-10 mm. Therefore, an individual with an abdominal LES of 15 mm at the age of 65 could experience LES incompetence after a meal (post-prandial) and exhibit symptoms associated with reflux disease (e.g., GERD). With intermittent reflux, the probability of visible columnar epithelium in the thoracic esophagus is low. Except in rare individuals in this group who develop visible columnar lined esophagus, the individuals in this group are not at risk for adenocarcinoma.

In some examples, individuals experiencing a rate of LES shortening of 5 mm per decade will have approximately a 25 mm reduction in abdominal LES in the 5 (five) decades between the ages of 15 and 65. Such an individual makes up approximately 7% of the general population and will have a dilated distal esophagus (a squamo-oxyntic gap) of 25 mm at the age of 65. A 25 mm reduction in abdominal LES will cause the individual to be left with an abdominal LES of approximately 10 mm at the age of 65. As this is the threshold at which an individual begins experiencing symptoms associated with reflux disease, the individual at age 65 will experience LES incompetence at rest and will experience severe symptoms associated with reflux disease. These people are at risk for developing visible columnar epithelium in their thoracic esophagus and are at risk for developing adenocarcinoma.

Individuals experiencing a rate of LES shortening of 6 mm per decade will have approximately a 30 mm reduction in abdominal LES in the 5 (five) decades between the ages of 15 and 65. These individuals make up approximately 3% of the general population and will have a dilated distal esophagus (a squamo-oxyntic gap) of 30 mm at the age of 65. A 30 mm reduction in abdominal LES will cause the individual to be left with an abdominal LES of approximately 5 mm at the age of 65. As this is below the threshold at which an individual experiences symptoms associated with reflux disease, this individual will, at age 65, experience incessant LES incompetence and will experience severe symptoms associated with reflux disease. These individuals are at high risk for developing visible columnar epithelium in their thoracic esophagus and are at the highest risk for developing adenocarcinoma.

Method of Determining Progression of Reflux Disease

Disclosed is a method of predicting the future progression of LES damage. The prediction of future LES damage progression can be closely related to the progression of severity of reflux, which in turn can be closely related to the occurrence of severe GERD. Severe GERD can correspond to one or more of failure to control symptoms with medical therapy, Barrett's esophagus, or adenocarcinoma. The prediction of future LES damage progression can also serve as a valuable tool to manage the progression of GERD.

In some embodiments, the disclosed method can identify the patients at highest risk of developing severe GERD and intervene to augment and prevent the progression of LES damage before it reaches the severe stage of LES damage. In some examples, the method can therefore identify, and permit interventions to help to prevent the progression of LES damage in patients who are destined to progress to severe GERD in the future.

In some embodiments, the method can also predict the majority of patients who are likely to remain well controlled with medical therapy into their advanced age. These individuals will need advice on diet modification, but can be reassured that they will be well controlled with medical therapy and will not be at risk for developing Barrett's esophagus or adenocarcinoma.

In some examples, the disclosed method can provide a new management aimed at preventing adenocarcinoma of the esophagus. The trend of ever increasing incidence of esophageal adenocarcinoma can therefore be reversed.

Assumptions for Development of Method for Determining Progression of Reflux Disease In view of the information provided above, the following information regarding the abdominal segment of the LES has been established and can be used in developing a method for determining the progression of reflux disease.

In some embodiments, the abdominal LES damage (e.g., shortening of the abdominal LES) can be accurately measured because it is equivalent in length to the length of the dilated distal esophagus which in turn is equivalent in length to the length of cardiac epithelium between the distal limit of esophageal squamous epithelium and the proximal limit of gastric oxyntic epithelium. In some examples, the length of cardiac epithelium can be measured with a suitable specimen because cardiac epithelium can be easily distinguished from squamous and gastric oxyntic epithelia by well-established histologic criteria. In some embodiments, with a suitable specimen, the accuracy of the measurement of cardiac epithelium can be within 1 μm using standard microscopy with a calibrated ocular measuring device that is standard equipment.

In some examples, the method can provide an individualized calculation of the rate of LES shortening for patients with a wide range of lifestyles. For example, LES shortening can progress very slowly over decades in some individuals. In such individuals, LES damage can be so slow that they never reach the point of failure and they never develop GERD. On the other hand, individuals with poor eating habits will have a rapid progression of damage to the abdominal LES such that the critical point of failure of the abdominal LES occurs early in life. The rate of abdominal LES shortening can therefore theoretically vary from 1 mm/decade to 10 mm/decade (see FIG. 12 illustrated above).

In some examples, it can be assumed that LES damage is caused by over-eating that can result in gastric over-distension. Gastric over-distension causes a temporary LES effacement at its distal end of 5-10 mm. As seen above in FIG. 13, this explains why individuals with an abdominal LES of 20 mm or less may experience LES incompetence and symptoms of GERD in the post-prandial period following a heavy meal.

In some embodiments, when the length of the abdominal LES becomes damaged such that its residual length is less than or equal to 10 mm, the LES becomes incompetent. At this point, the LES fails intermittently and abnormal reflux of gastric contents occurs into the esophagus. This can result in symptoms and complications of GERD including failure of PPI therapy to control symptoms, Barrett's esophagus and adenocarcinoma. At this time, there is no method to prevent these complications. Medical therapy is presently directed only at controlling symptoms of GERD. It does not influence the progression of LES damage in any positive way.

While there is no data on the growth and development of the LES, in some embodiments, it can be generally assumed that the LES completes its development at age 10-15 years when growth is nearing completion. In one embodiment, at the age of 15, the full length of the abdominal LES is approximately 35 mm. The first age (e.g., 15 years) and/or full abdominal LES length (e.g., 35 mm) can be adjusted based upon various criteria, such as discussed above. As discussed above, this full length (35 mm) is based on a study of persons asymptomatic of GERD.

The length of the dilated distal esophagus/squamo-oxyntic gap/metaplastic columnar epithelium between the proximal limit of gastric oxyntic epithelium and the distal limit of squamous epithelium can be used to provide a measure of LES damage. This measurement can be made in any person at any time of that patient's life.

While there is no way of knowing when LES damage begins, because LES damage results from an improper eating habit, it can be assumed that LES damage begins when the eating habit develops. In some embodiments, we assume that eating habits are established at the age of 15 that may or may not begin causing damage to the LES. As noted above, we can assume the starting age to be 15 years old which we can define as the age where abdominal LES shortening begins. In some examples, the method for determining the progression of reflux disease assumes that the abdominal LES is fully developed at the age of 15. In other embodiments, the method for determining the progression of reflux disease accounts for varying eating habits by adjusting the starting age of developed eating habits at an age above or below 15. For example, if an individual has a history of childhood obesity, the method for determining the progression of reflux disease can adjust the starting age to 10 years of age. In some embodiments, the initial age is determined by asking the patient questions regarding his or her current and/or historical eating habits.

In some embodiments, progression of abdominal LES damage is likely to occur in a linear manner. This assumes a constant rate from one decade to the next assuming that the patient's general eating habit does not change. This assumption is supported by the fact that there is evidence that LES damage has no vicious cycle effect. Therefore, in some embodiments, this means that the LES is affected by gastric distension to the same extent irrespective of its baseline residual length. In some examples, additional data points regarding the eating habits of the individual can be used to adjust the starting point at which we begin calculating the rate of developing reflux disease. In some embodiments, the progression type (e.g., linear, exponential, logarithmic, etc.) is determined by asking the patient questions regarding his or her current and/or historical eating habits.

In some examples, the new test can be used to measure abdominal LES at any time in the patient's life. In some embodiments, it can be done whether the patient has GERD or not and at any age over 30 years. The test can provide an accurate measure of LES damage on the date at which the test is performed.

Method for Determining Progression of Reflux Disease

Given the aforementioned, a method can be developed that will predict the future status of the abdominal LES and allow for more appropriate clinical interventions. This method will require entry of a number of data points into a computer-based user interface.

In some embodiments, the method can request the individual's date of birth. The program would add the initial age (e.g., 15 years) to this date to represent zero LES damage (e.g., the age at which LES damage begins. In some embodiments, this addition can be changed when data accumulates regarding LES growth and development and onset of damage. In some examples, as noted above, the starting date can be changed to 10 years (or other age) if there is a history of childhood obesity (or due to other conditions).

In some examples, the method requests the date on which the test was performed. As noted above, because it is assumed in one embodiment that the rate of damage to the abdominal LES is linear (e.g., there is no evidence that LES damage has a "vicious cycle" effect). In some embodiments, knowing the date in which the test was preformed can be used to determine the rate of damage from the starting age (e.g., 10 or 15 years old, or some other first age).

In some embodiments, the method can request or determine the exact measure of LES damage defined by the test. LES damage can be obtained in a number of ways. As will be discussed in more detail below, in some examples, damage to the abdominal LES can be obtained by an exact microscopic measurement of the dilated distal esophagus/squamo-oxyntic gap in an appropriate biopsy specimen using an ocular micrometer.

In some embodiments, the entry of these three data points into the computer-based interface will calculate a projection of the length of the abdominal LES into the future (e.g., the future damage of the abdominal LES). In some examples, this can depend on date of the measurement of abdominal LES damage, the date of birth (with the program adjusted to add 15 years in a person with no history of childhood obesity or 10 years if the person had childhood obesity, etc.), and the amount of abdominal LES damage at the time of the test made by microscopic measurement in an appropriate biopsy sample. In some embodiments, the linear (or other type of) progression developed can be extrapolated well into the future.

FIGS. 3A-3E illustrate example progression curves generated using the method described above. Each of these example progression curves can provide a physician with information to provide a patient with a treatment plan to prevent or delay the onset of GERD or slow the onset of Reflux disease.

Figure 3A:
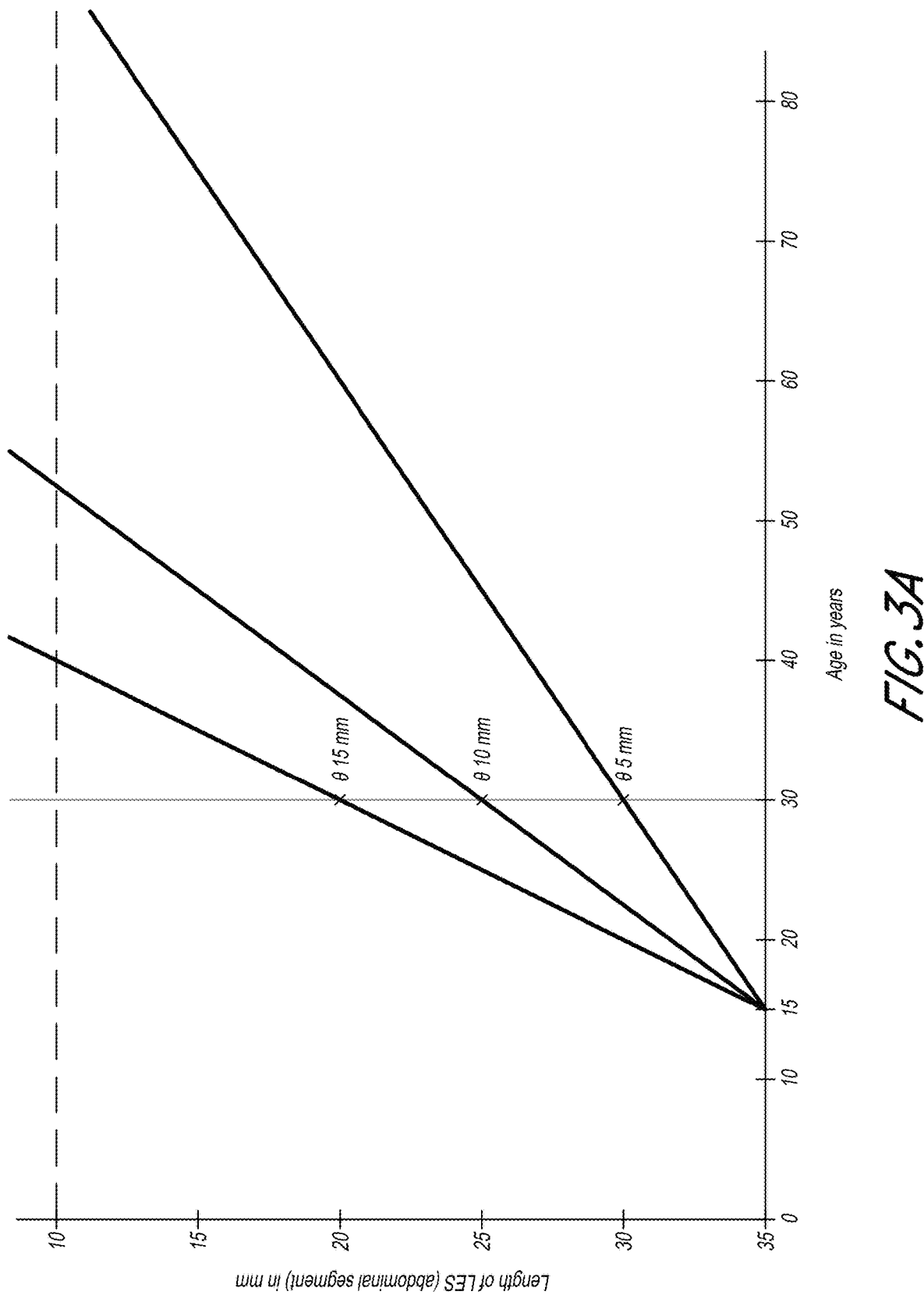
FIG. 3A illustrates example progression curves of abdominal LES damage in a patient at age 30 with abdominal LES damage of 5 mm, 10 mm, and 15 mm.

Turning first to FIG. 3A, FIG. 3A illustrates example progression curves of abdominal LES damage in a patient at age 30 with abdominal LES damage of 5 mm, 10 mm, and 15 mm. As illustrated in FIG. 3A, assuming an abdominal LES damage of 5 mm at age 30, the progression curve estimates that the abdominal LES will reach a length of 10 mm (e.g., the LES becomes incompetent) past the age of 80. For an individual with an abdominal LES damage of 10 mm at age 30, the progression curve estimates that the abdominal LES will reach a length of 10 mm (e.g., the LES becomes incompetent) at age 53. Lastly, for an individual experiencing 15 mm of abdominal LES damage at age 30 will reach a length of 10 mm (e.g., the LES becomes incompetent) at age 39.

Figure 3B:
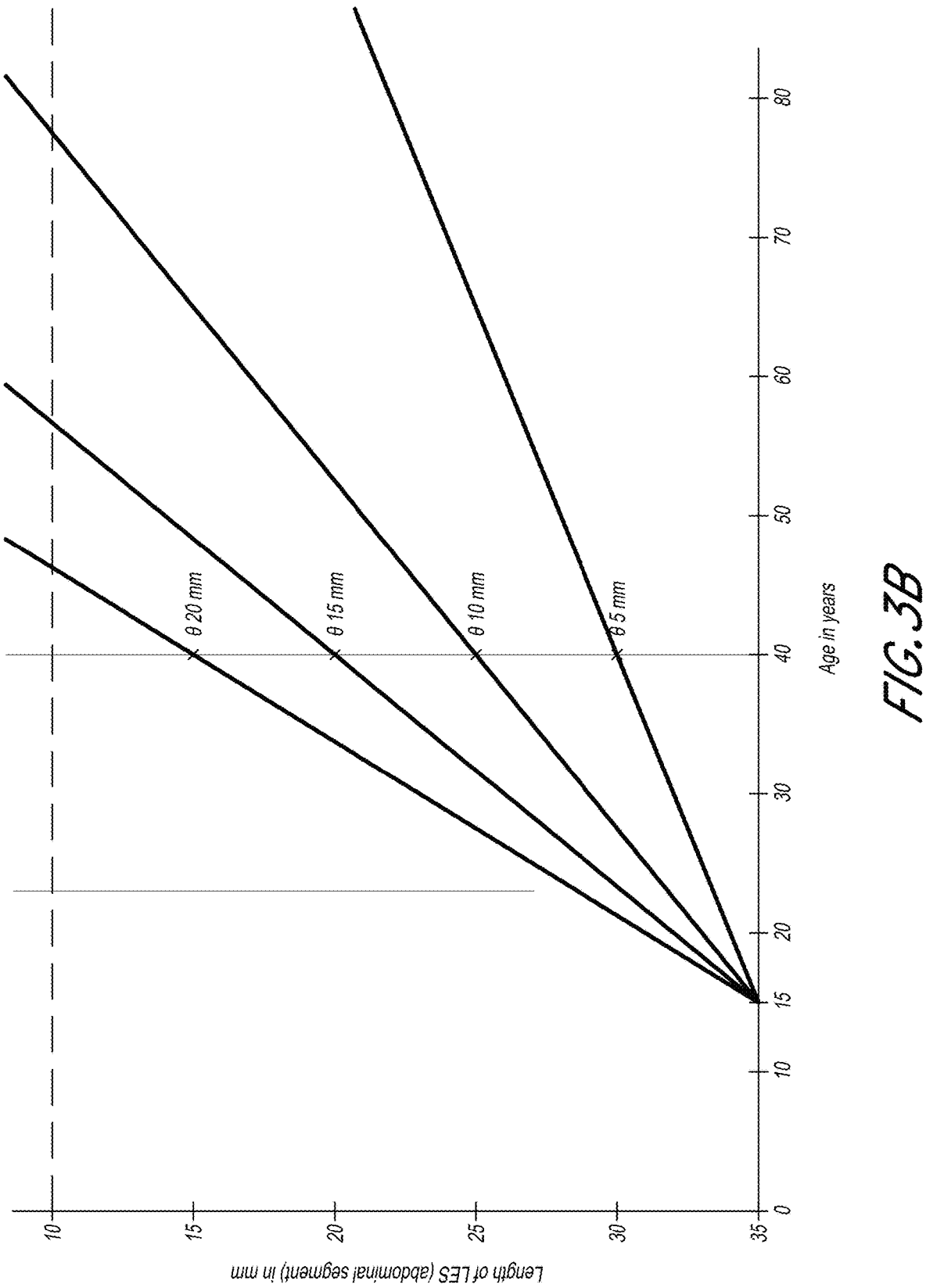
FIG. 3B illustrates example progression curves of abdominal LES damage in a patient at age 40 with abdominal LES damage of 5 mm, 10 mm, and 15 mm.

FIG. 3B illustrates example progression curves of abdominal LES damage in a patient at age 40 with abdominal LES damage of 5 mm, 10 mm, and 15 mm. As illustrated in FIG. 3B, assuming an abdominal LES damage of 5 mm at age 40, the progression curve estimates that the abdominal LES will reach a length of 10 mm (e.g., the LES becomes incompetent) past the age of 80. For an individual with an abdominal LES damage of 10 mm at age 40, the progression curve estimates that the abdominal LES will reach a length of 10 mm (e.g., the LES becomes incompetent) at age 76. An individual experiencing 15 mm of abdominal LES damage at age 40 will reach a length of 10 mm (e.g., the LES becomes incompetent) at age 57. Lastly, the progression curve shows that an individual with an abdominal LES damage of 20 mm at age 40 will have an abdominal LES with a length of 10 mm (e.g., the LES becomes incompetent) at age 45.

Figure 3C:
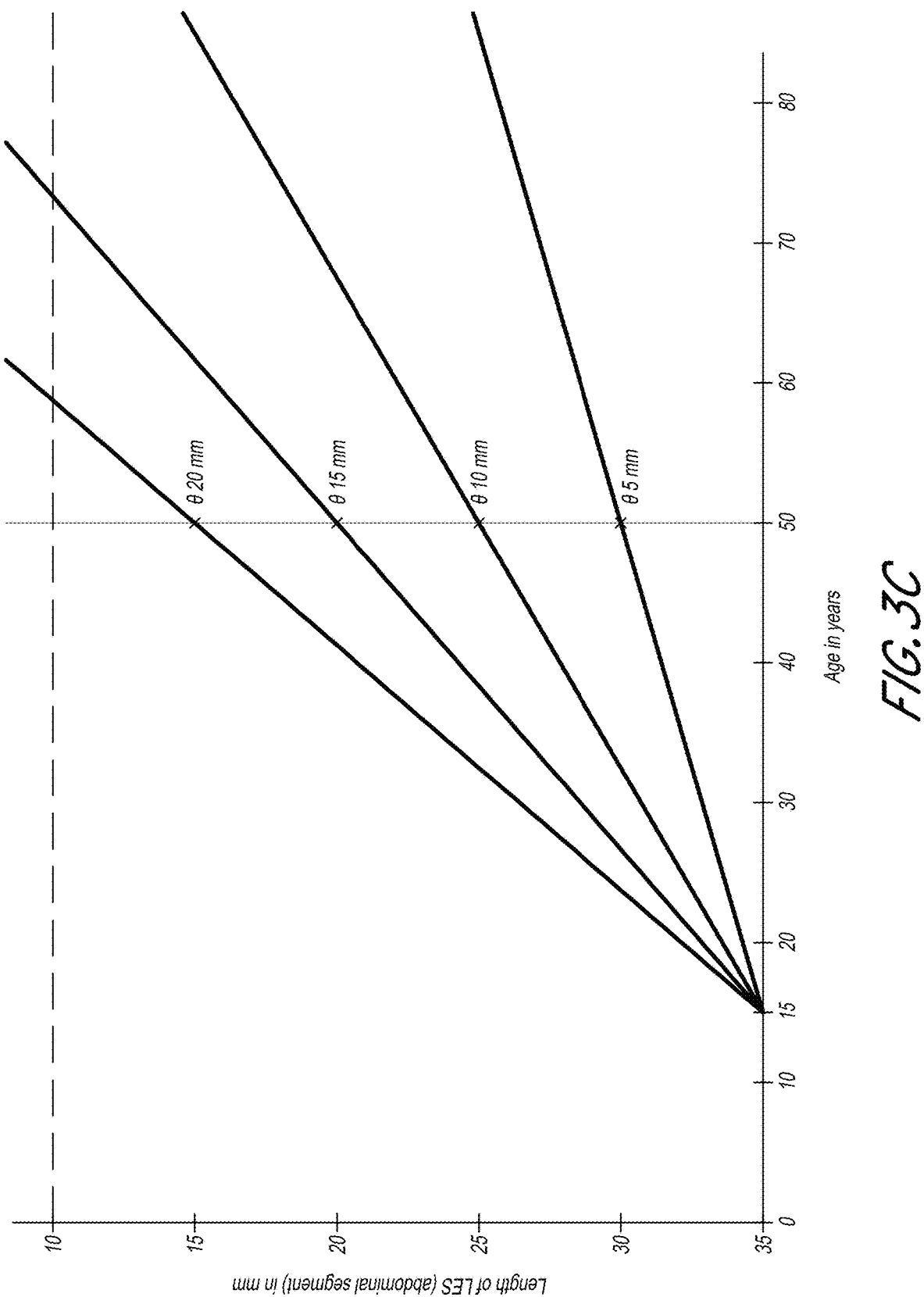
FIG. 3C illustrates example progression curves of abdominal LES damage in a patient at age 50 with abdominal LES damage of 5 mm, 10 mm, and 15 mm.

FIG. 3C illustrates example progression curves of abdominal LES damage in a patient at age 50 with abdominal LES damage of 5 mm, 10 mm, and 15 mm. As illustrated in FIG. 3C, assuming an abdominal LES damage of 5 mm at age 50, the progression curve estimates that the abdominal LES will reach a length of 10 mm (e.g., the LES becomes incompetent) past the age of 80. For an individual with an abdominal LES damage of 10 mm at age 50, the progression curve estimates that the abdominal LES will reach a length of 10 mm (e.g., the LES becomes incompetent) past the age of 80. An individual experiencing 15 mm of abdominal LES damage at age 50 will reach a length of 10 mm (e.g., the LES becomes incompetent) at age 72. Lastly, the progression curve shows that an individual with an abdominal LES damage of 20 mm at age 40 will have an abdominal LES with a length of 10 mm (e.g., the LES becomes incompetent) at age 57.

Figure 3D:
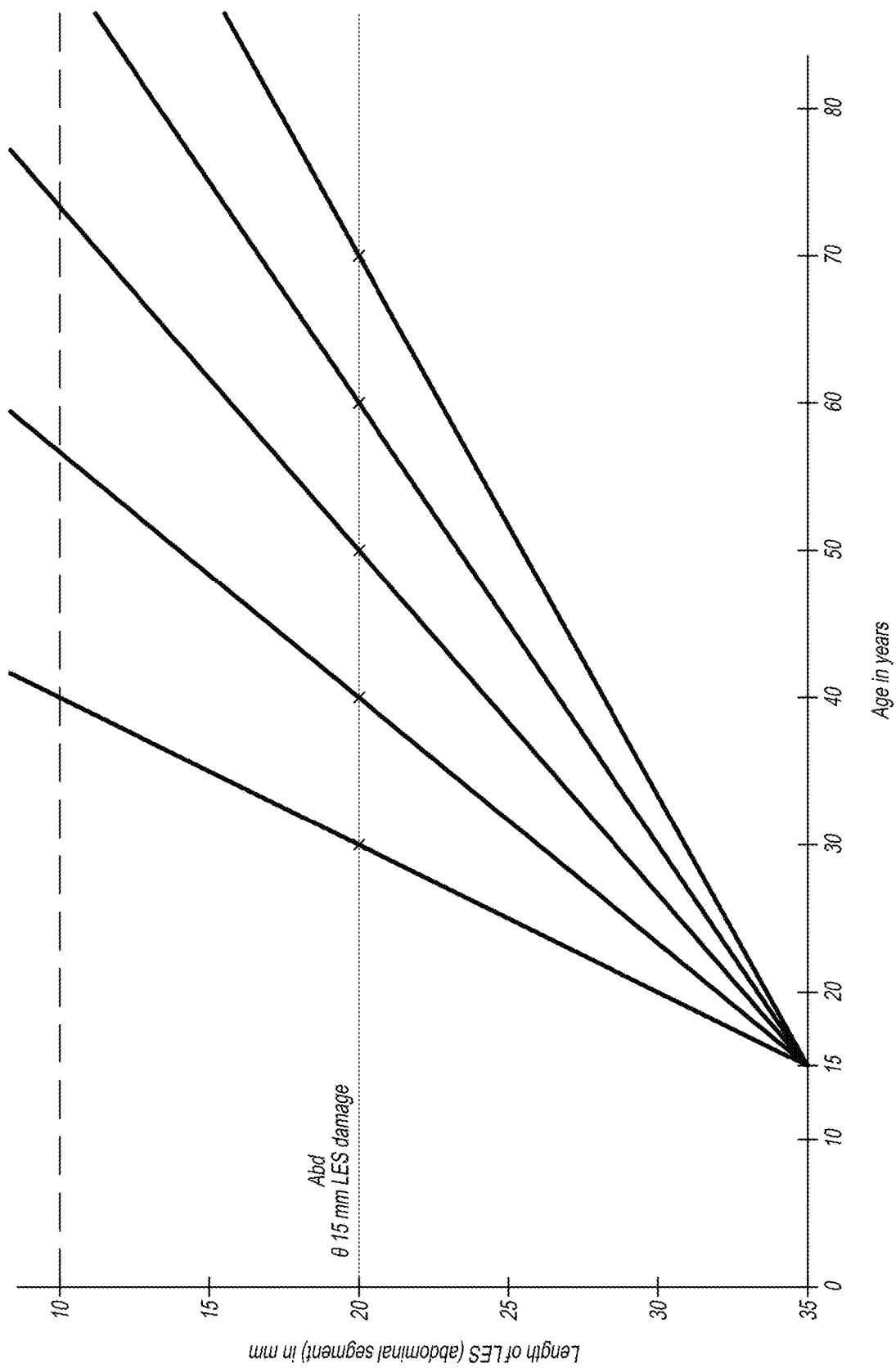
FIG. 3D illustrates example curves of abdominal LES damage in patients aged 30, 40, 50, 60, and 70 years with an initial abdominal LES damage of 15 mm.

FIG. 3D illustrates example curves of abdominal LES damage in patients aged 30, 40, 50, 60, and 70 years with an initial abdominal LES damage of 15 mm. As shown in FIG. 3D, an individual at age 30 experiencing an initial abdominal LES damage of 15 mm will have an abdominal LES damage of 10 mm (e.g., the LES becomes incompetent) at age 41. An individual at age 40 experiencing an initial abdominal LES damage of 15 mm will have an abdominal LES damage of 10 mm (e.g., the LES becomes incompetent) at age 57. An individual at age 50 experiencing an initial abdominal LES damage of 15 mm will have an abdominal LES damage of 10 mm (e.g., the LES becomes incompetent) at age 73. An individual at age 60 experiencing an initial abdominal LES damage of 15 mm will have an abdominal LES damage of 10 mm (e.g., the LES becomes incompetent) after age 80. An individual at age 70 experiencing an initial abdominal LES damage of 15 mm will have an abdominal LES damage of 10 mm (e.g., the LES becomes incompetent) after age 80.

Figure 3E:
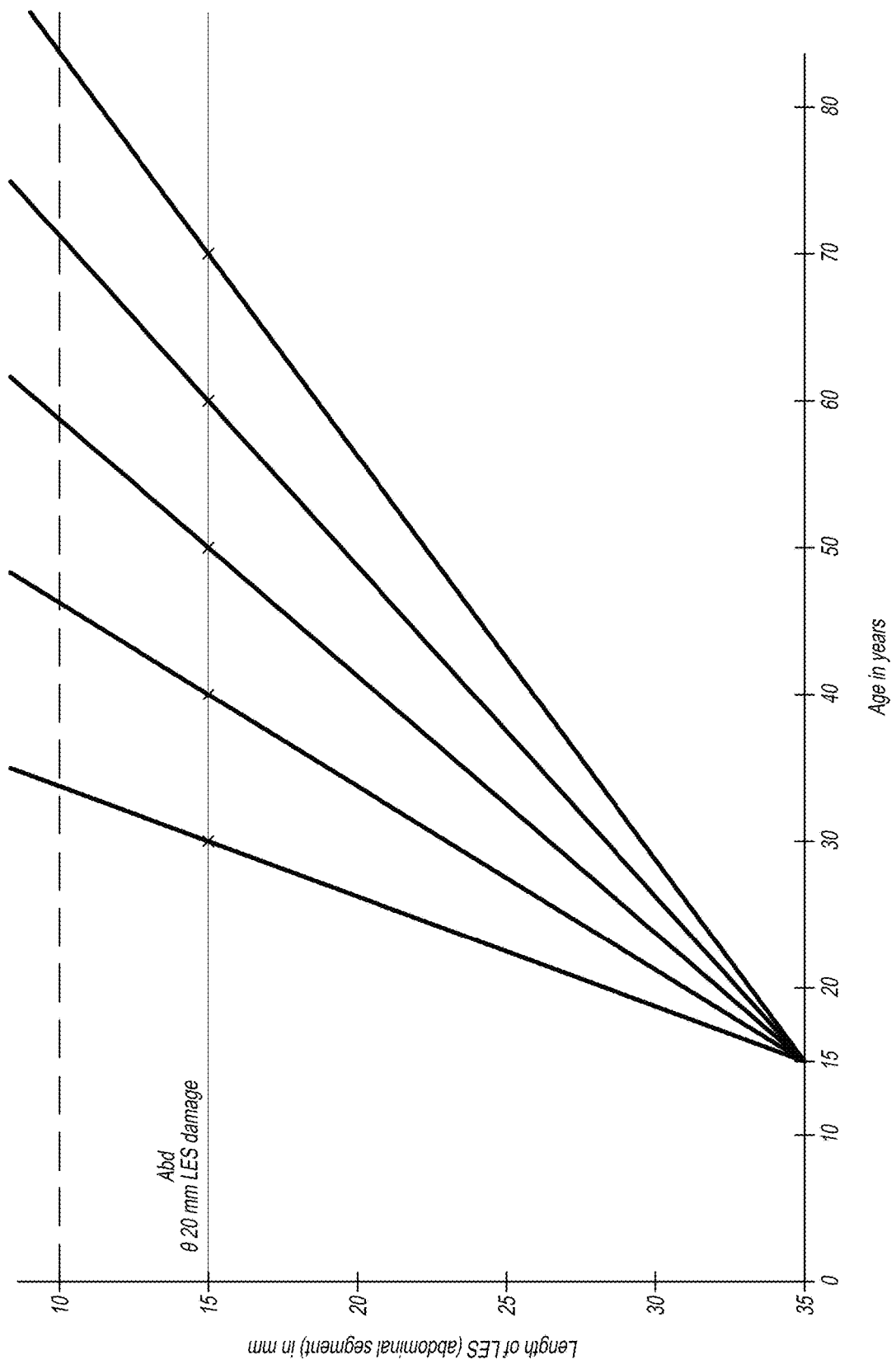
FIG. 3E illustrates example curves of abdominal LES damage in patients aged 30, 40, 50, 60, and 70 years with an initial abdominal LES damage of 20 mm.

FIG. 3E illustrates example curves of abdominal LES damage in patients aged 30, 40, 50, 60, and 70 years with an initial abdominal LES damage of 20 mm. As shown in FIG. 3E, an individual at age 30 experiencing an initial abdominal LES damage of 20 mm will have an abdominal LES damage of 10 mm (e.g., the LES becomes incompetent) at age 33. An individual at age 40 experiencing an initial abdominal LES damage of 20 mm will have an abdominal LES damage of 10 mm (e.g., the LES becomes incompetent) at age 45. An individual at age 50 experiencing an initial abdominal LES damage of 20 mm will have an abdominal LES damage of 10 mm (e.g., the LES becomes incompetent) at age 60. An individual at age 60 experiencing an initial abdominal LES damage of 20 mm will have an abdominal LES damage of 10 mm (e.g., the LES becomes incompetent) at age 71. An individual at age 70 experiencing an initial abdominal LES damage of 20 mm will have an abdominal LES damage of 10 mm (e.g., the LES becomes incompetent) after age 80.

In some examples, the method for determining the progression of reflux disease can be personalized to the individual person based on the age of the person when the test was performed (i.e. date of the test minus date of birth) and the exact measure of damage to the abdominal LES.

Example Calculation

For example, an individual, without a history of childhood obesity, 56 years in age is found to have LES damage of 4 mm. This demonstrates that the individual's eating habit had resulted in a shortening of the abdominal LES of 4 mm in 41 years:

Rate of Damage to the Abdominal LES=4 mm/41 years≈0.098 mm/years

At an LES damage rate of approximately 0.1 mm/year, assuming that the progression of LES damage is linear, the method for determining the progression of reflux disease will predict that the individual will have double the damage—approximately 8 mm of abdominal LES damage—at 97 years old.

Age for Doubling Damage to Abdominal LES=56 years+41 years=97 years

Given an initial length of 35 mm of initial abdominal LES length, the individual will have a residual abdominal LES length of 27 mm (35 mm-8 mm=27 mm) at age 97. As this is well above the threshold 10 mm length that indicates LES failure and reflux, the method for determining the progression of reflux disease would determine that the individual would never develop GERD in the individual's natural lifetime. In fact, this person's abdominal LES length will be predicted to reach 10 mm at age 240 years. The LES is designed with a high reserve capacity that can withstand significant dietary abuse.

As illustrated above, the method for determining the progression of reflux disease can be used to generate a number of different data points. For example, the method can calculate the age at which an individual will develop reflux that will be associated with symptomatic GERD, the age in the future at which an individual will have a certain length of damage to the abdominal LES, whether an individual will develop reflux disease by the end of natural life, whether the individual will be at any risk of developing severe GERD (with treatment failure, Barrett's esophagus and adenocarcinoma) and if so, at what age this will happen, etc.

In some embodiments, the method for determining the progression of reflux disease utilizes the length of the dilated distal esophagus/squamo-oxyntic gap/metaplastic columnar epithelium.

For example, the length can be determined based upon the individual—for example, as discussed above, the initial length of the abdominal LES and the amount of abdominal LES that must remain before symptoms appear (e.g., the LES critical length) can be determined on an individual basis. For example, in some embodiments, the length of the dilated distal esophagus (or squamo-oxyntic gap, or metaplastic columnar epithelium) can be determined as the difference between the initial length of the abdominal LES and the critical length.

For example, in one embodiment, the starting length of the abdominal LES is 35 mm and the critical length is 10 mm (e.g., the abdominal LES will fail when it is less than 10 mm) in the postprandial phase. A method of determining a failure time (e.g., when the individual will experience LES incompetence) is determined to be the time when the dilated distal esophagus (or squamo-oxyntic gap, or metaplastic columnar epithelium) is the difference between the starting and critical lengths (e.g., 35 mm-10 mm=25 mm).

In other embodiments, the method for determining the progression of reflux disease is based upon one or more factors, such as, but not limited to: dietary habits, lifestyle choices, genetic pre-dispositions, and general health history. In some embodiments, the estimated rate of the progression of reflux disease is determined based on one or more factors, such as, but not limited to: dietary habits, lifestyle choices, genetic pre-dispositions, and general health history. In some embodiments, instead of age, the method for determining the progression of reflux disease can be determined based upon one or more discreet events in the patient's life.

Benefit of Method for Determining Progression of Reflux Disease

In some embodiments, the disclosed method can provide an accurate assessment of abdominal LES damage by measuring the length of cardiac epithelium (with and without parietal and/or goblet cells) between the distal limit of esophageal squamous epithelium and gastric oxyntic epithelium.

The measured assessment of LES damage can provide information regarding the likelihood of GERD at the time of testing. Presently, there is no way to exclude GERD as a cause for symptoms that could be caused by GERD. As a result, many patients whose symptoms are not caused by GERD are unnecessarily treated with proton pump inhibitors (PPI). A person with LES damage less than or equal to 1.5 cm has a damaged but competent LES that is highly unlikely to permit sufficient reflux into the thoracic esophagus that will be the cause of GERD symptoms.

In some examples, the method for determining the progression of reflux disease can provide a prediction of future abdominal LES status. In some embodiments, the method can help to stratify individuals into four groups.

In some examples, the individual can fall into a group of people who will never develop GERD. Such a categorization can only be achieved if the test is performed in a person without symptoms of GERD. This can represent up to 70% of the population at large.

In some embodiments, the individual can fall into a group of people whose progression of LES is slow enough that they will remain with a reasonably adequate LES throughout their lives with a low risk of complications resulting from severe GERD in the future. These individual can be provided advice on dietary modifications that can likely be controlled with PPI therapy throughout their lives. This can represent 20-25% of the population at large and 70% of people with symptomatic GERD who are under PPI therapy.

In some embodiments, the individual can fall into a group of people who are predicted to progress to severe LES damage more than 10 years from the date of the test. These patients can be shown their future prediction of LES damage and be strongly advised to modify their diet. These individual can be brought back for a repeat test in 5 years. This will provide a second measurement that will make the personalized method more accurate and provide a better prediction. In some examples, if at the time of the follow up test, the individual is projected to progress to severe LES damage within 5 years, the patient will be, as discussed below, advised to consider a procedure to augment their LES and prevent progression of LES damage. In some embodiments, if the individual's subsequent test does not show that the individual is projected to progress to severe LES damage within 5 years, the patient can be asked to have a follow up test (e.g., a couple of years to 5 years thereafter).

In some examples, the individual can fall into the group of patients who are predicted by the test to progress to severe LES damage within the next 5 years and can be advised to consider a procedure to augment their LES and prevent progression of LES damage. In some embodiments, the subsequent procedure can be endoscopic (e.g., TIF, Stretta). In some embodiments, the procedure can be laparoscopic (e.g., LINX, fundoplication).

To better illustrate the various scenarios that an individual may experience, the aforementioned data, along with a linear extrapolation, can be provided to the client visually. In some embodiments, the user interface can generate a visual representation of the individual's risk of GERD as well as potential treatment options.

Method of Measuring the Dilated Distal Esophagus

As noted above, disclosed is a method for measuring the dilated distal esophagus, defined as the length of metaplastic columnar epithelium between the distal limit of esophageal squamous epithelium and the proximal limit of gastric oxyntic epithelium. This has been termed the squamo-oxyntic gap. As noted above, as the actual length of the abdominal LES is difficult to measure, the remaining length of the abdominal LES can be approximately assessed by measuring the dilated distal esophagus and comparing that to the approximate 35 mm length of abdominal LES that adult individuals are estimated to have.

As noted above the widely held belief that cardiac epithelium is normally present distal to the gastroesophageal junction in the proximal stomach has been called into question with evidence that the presence of cardiac epithelium distal to the squamocolumnar junction correlates with the presence of GERD. Evidence also exists that increase in the length of cardiac epithelium correlates with increasing severity of GERD. The data regarding the aforementioned is limited because the American Gastroenterologist Association (AGA) recommends that no biopsies should be taken distal to the endoscopic gastroesophageal junction (GEJ) when endoscopy is performed in patients with GERD. In patients with no endoscopic abnormality, biopsies are not recommended. In patients with visible columnar metaplasia above the endoscopic gastroesophageal junctions, biopsies are recommended only at and above the endoscopic gastroesophageal junction.

The presence of metaplastic esophageal cardiac epithelium distal to the endoscopic definition of the GEJ and the fact that increasing lengths of this epithelium correlates with increasing severity of GERD calls into question the veracity of the endoscopic definition of the GEJ (which is the proximal limit of the rugal folds). While the AGA management guidelines recognize that this endoscopic definition of the GEJ has no supporting evidence, it continues to recommend that it be used to define the GEJ.

Evidence has shown, based on histologic examination of resection specimens, that the endoscopic definition of the GEJ is wrong. Rather, the extent of cardiac epithelium distal to the endoscopic GEJ was concordant with the presence of esophageal submucosal glands. This demonstrated that the actual GEJ was located distal to the endoscopic GEJ. The actual GEJ could instead be defined histologically by the proximal limit of the presence of gastric oxyntic epithelium. Data also showed that the length of cardiac epithelium was greater in persons with GERD than in those without.

As discussed above, there is therefore a segment of esophagus distal to the endoscopic GEJ (also the distal limit of esophageal squamous epithelium in people who are normal at endoscopy) that is presently termed the "dilated distal esophagus." The dilated distal esophagus refers to the same length of tissue as the squamo-oxyntic gap distal to the endoscopic gastroesophageal junction in a person without columnar metaplasia above the endoscopic junction. As noted above, this is defined as the area lined by cardiac epithelium—cells with and without parietal and/or goblet cells. The extent of this area can vary between zero (the normal) to a maximum measured amount of 28 mm.

The pathogenesis of the dilated distal esophagus is damage to the abdominal segment of the lower esophageal sphincter (abdominal LES). Then length of the dilated distal esophagus is the amount of shortening of the abdominal LES. This length is concordant with the length of cardiac epithelium between the distal limit of esophageal squamous epithelium and the proximal limit of gastric oxyntic epithelium in people who are endoscopically normal. Measurement of this cardiac epithelial length is therefore a test of abdominal LES damage—the primary cause of GERD.

As noted above, the value in measuring the cardiac epithelium in the management of GERD can provide for earlier diagnosis of GERD, prediction of future LES damage, and provide for early treatment of GERD that has the potential to prevent complications of GERD such as treatment failure, Barrett's esophagus, and esophageal adenocarcinoma.

Method for Measuring Cardiac Epithelial Length Using Endoscopic Biopsy

Disclosed is a measurement of cardiac epithelial length that can be done with accuracy to within 1 μm in a vertical section taken from the squamo-columnar junction distally for a length ranging from 5 mm to 30 mm. In some embodiments, this strip of mucosa will traverse the area that can be maximally composed of cardiac epithelium. Once excised, the vertical strip of mucosa and standard microscopy with an inbuilt calibrated optical micrometer can be used to provide an accurate measurement of the length of cardiac epithelium.

The disclosed biopsy device configured to excise the vertical section can recapitulate the vertical section that accurately measure cardiac epithelial length in resected specimens and at autopsy. In some examples, the device will take a longitudinal piece of tissue from the squamo-columnar junction (endoscopic GEJ in the person without visible columnar lined or Barrett's esophagus) to a point distal to it. The objective is for the distal margin of the biopsy to reach gastric oxyntic epithelium. When this is achieved the squamo-oxyntic gap can be measured with an accuracy of micrometers.

However, unlike a specimen taken from a resected specimen, in some embodiments, the device is only required to obtain a piece of mucosal tissue that has a maximum length of 30 mm. In some embodiments, only 20 mm may be required for application of the test. In some examples, the device may have length variation such that the user can choose a mucosal biopsy length of 10 mm, 15 mm, 20 mm, 25 mm, 30 mm, and 35 mm. In some embodiments, the vertical section can include a length between and including 5 mm-10 mm, 10 mm-15 mm, 15 mm-20 mm, 20 mm-25 mm, or 25 mm-30 mm. In some embodiments the vertical section can have a length less than or equal to 5 mm. In some examples, the vertical section can have a length greater than or equal to 30 mm.

Presently available biopsy forceps do not allow obtaining a sample that traverses the entire dilated distal esophagus. While multiple biopsies potentially can be taken, such a procedure will not be easily reproducible, will be cumbersome, add time to the procedure, and will never be able to match the accuracy of one continuous mucosal sample that will be taken over the entire length of the abdominal LES of 35 mm.

In some embodiments, the vertical tissue has a width of between 2 mm to 3 mm and a depth of 1 mm. In some examples, the biopsied tissue can have a width greater than 3 mm or less than 2 mm. In some examples, the biopsied tissue can have a width between and including about 1 mm-2 mm, 2 mm-3 mm, 3 mm-4 mm, 4 mm-5 mm, 5 mm-6 mm, 6 mm-7 mm, 7 mm-8 mm, 8 mm-9 mm, and 9 mm-10 mm. In some examples, the depth of the tissue can be less than 1 mm. In some examples, the depth of the tissue can be greater than 1 mm. The depth may only need to reach the portion of the mucosa which is necessary to distinguish between cardiac epithelium and gastric oxyntic epithelium. This vertical strip of mucosa will permit histologic classification of the type of epithelium in the 30 mm segment of mucosa. In some embodiments, the different types of epithelia present can be measured using a microscope fitted with a standard calibrated ocular micrometer.

As noted above, the longitudinal piece of mucosal tissue removed can be used to measure the length of the dilated distal esophagus which represents the damage to the abdominal LES. As noted above, the squamo-oxyntic gap (in the patient without Barrett's esophagus) corresponds to the shortening/damage to the abdominal LES, which corresponds to the length of the dilated distal esophagus, which corresponds to the measurement made in the longitudinal sample procured by the disclosed device. In some embodiments, an optical measurement can be made of the removed mucosal tissue using an ocular micrometer that is attached to a microscope. The measurement will reflect the length of the distal limit of the squamous epithelium to the proximal limit of the gastric oxyntic epithelium. In some embodiments, this is accurate within micrometers.

Figure 5A:
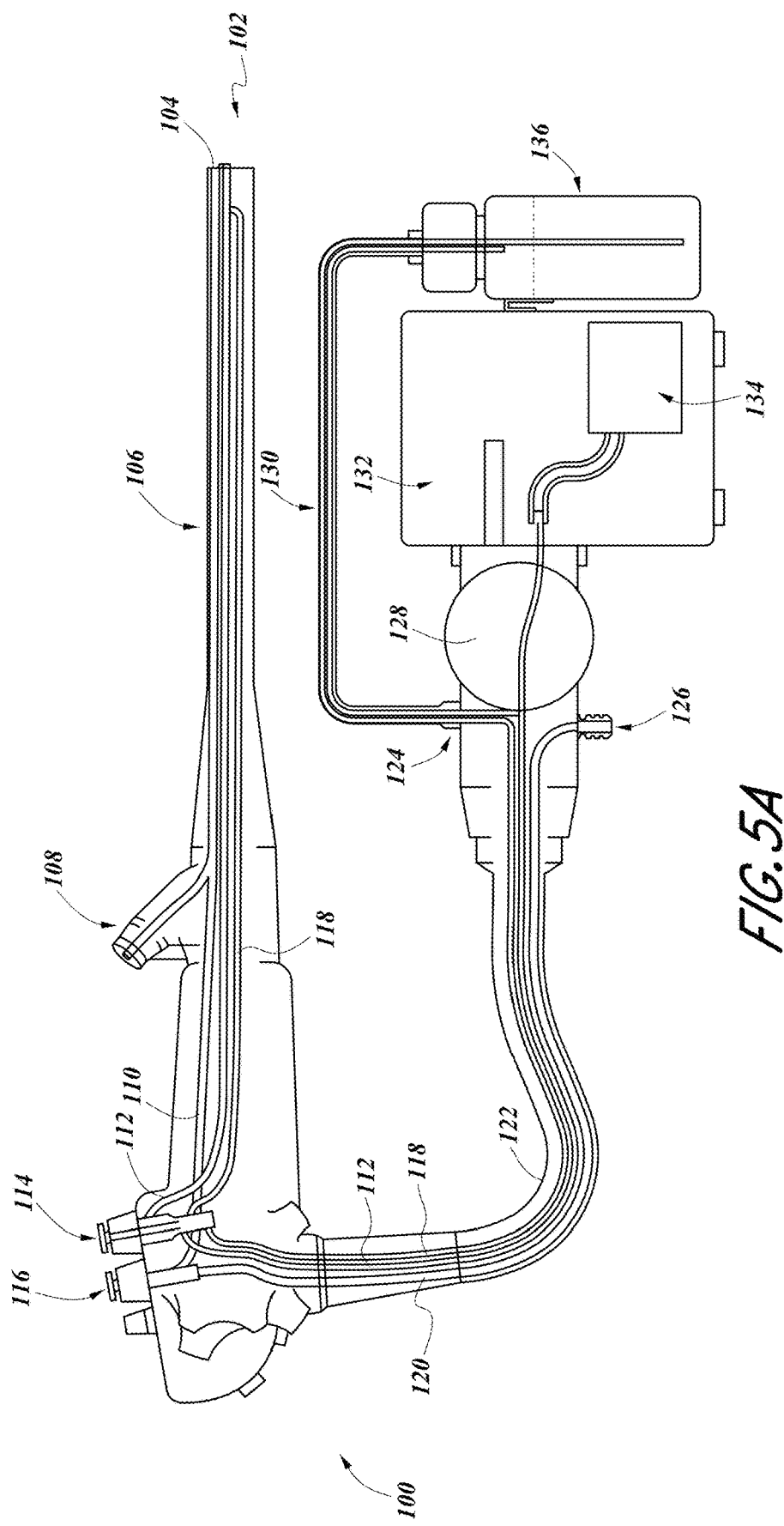
FIG. 5A illustrates a cross-sectional view of an endoscope that is configured to receive an embodiment of a biopsy device.

As illustrated in FIGS. 5A-5B, the biopsy device can be configured to pass through the biopsy channel of an endoscope at upper gastrointestinal endoscopy. In some embodiments, it can be passed vertically and be deployed when it has entered the lumen. FIG. 5A illustrates an embodiment of an endoscope 100 that the biopsy device can be inserted into. In some examples, the endoscope 100 can include an insertion tube 106 that allows access a patient's digestive tract. In some embodiments, the insertion tube 106 can house a plurality of lumens that allow a physician to access a portion of the patient's digestive tract at a distal end 102 of the insertion tube 106. In some embodiments the distal end 102 of the endoscope 100 includes a nozzle 104 that can allow a physician to, for example, photograph, biopsy, or perform some medical procedure on an adjacent portion of the digestive tract.

In some examples, the plurality of lumens that extend the length of the insertion tube 106 can include, for example, an air channel 112, a working channel 110, and a water channel 118. In some embodiments, each of these channels are fluidly connected to a valve or an external opening to allow a physician to have control of movement through each of the channels. As will be discussed in more detail below, the endoscope 100 can include a housing (sometimes referred to as tube, cable, or universal cord) 122 that provides a housing to allow a fluid connection from external sources (e.g., water, air, suction, light) into the plurality of channels that are housed within the insertion tube 106.

Turning first to the air channel 112, in some embodiments the air channel 112 of the endoscope 100 is fluidly connected to an air channel 112 that is housed within the universal cord 122. In some embodiments, the air channel 112 is fluidly connected to an air pump 134 that allows air flow through the air channel 112. In some examples, the endoscope 100 includes a valve 114 that can allow a physician to have control over the flow of air through the air channel 112. In some embodiments, the valve 114 can be compressed or depressed to allow air to flow to the nozzle 104 at the distal end 102 of the endoscope 100.

In some examples, the endoscope 100 can include a working channel 110 that is configured to allow a physician to reach a portion of the patient's digestive tract. In some embodiments, the working channel 110 can be fluidly connected to the suction channel 120 that extends through the universal cord 122. In some examples, the suction channel 120 is fluidly connected to a suction port 126 that allows for suction to be applied through the working channel 110. In some embodiments, the endoscope 100 includes a suction valve 116 that allows a physician to have control over when suction is applied.

In some embodiments, the endoscope 100 includes a biopsy opening 108 that is fluidly connected to and allows access to the working channel 110. As mentioned above (and discussed in more detail below), the biopsy opening 108 allows a device (for example the biopsy device) to be inserted into. As noted above, the suction valve 116 can allow an inserted biopsy device to apply suction to the tissue of the digestive tract.

In some examples, the endoscope 100 can include a water channel 118 that is fluidly connected to a water channel 118 that is housed within the universal cord 122. In some embodiments, the universal cord 122 is fluidly connected to a water bottle 136. As shown in FIG. 5A, the water channel 118 can be fluidly attached to the water bottle 136 through a water bottle connection 124 and a water bottle tube 130. In some examples, the water channel 118 is fluidly connected to the air channel 112 near the distal end 102 of the endoscope 100. In some embodiments, the fluid connection between the air channel 112 and the water channel 118 allows for water to be pumped out of the nozzle 104 at the distal end 102 of the endoscope 100 when the valve 114 is depressed.

In some embodiments, the endoscope 100 can also include a light source 132 that uses a light source connector 128 to provide lighting to the endoscope 100. As will be discussed in more detail below, the endoscope 100 can have a light source to allow a physician to have better visualization of the patient's digestive tract.

FIG. 5B illustrates an examples cross-section of the insertion tube 106. As discussed above, the insertion tube 106 can house a working channel 110, an air channel 112, and a water channel 118. In some embodiments, the insertion tube 106 of the endoscope 100 can further include a plurality of control wire 138 that allow control of the insertion tube 106 along its length. In some examples, the plurality of control wire 138 can allow a physician to have control over a distal end 102 of the insertion tube 106 (e.g., to curve or bend). In some embodiments, the insertion tube 106 can house a plurality of fiber-optic cables (e.g., fiberoptic light guide/image bundle 140) that can provide the endoscope 100 with imaging capabilities.

In some examples, when endoscopy is performed, the endoscope can be passed from the esophagus into the stomach. It can then be retroflexed to obtain a view of the region distal to the esophageal opening. In some embodiments, the view can allow visualization and grading of the Hill valve. Progressive shortening of the Hill valve may be caused by LES damage because it correlates with severity of GERD. Endoscopy allows the shortening of the esophageal impression to be visible with the opening seemingly moving up and becoming more patulous. When air is insufflated into the stomach in the person with normal endoscopy (someone without Barrett's esophagus), the squamous epithelium appears below the opening of the esophagus. This marks the proximal limit of the placement of the biopsy device. The device can be positioned vertically from this point along the lesser curvature which is relatively flat. When thus positioned, a tissue capturing mechanism may be activated to draw, pull, or push mucosa into the interior of the device (e.g., 2 mm-3 mm wide and e.g., 1 mm-2 mm deep). The device may be activated to remove the drawn mucosa from the patient, e.g., by cutting it and holding it within a sample chamber of the device. This will produce a suitable specimen for analysis according to the methods described herein. As noted above, the length of the specimen will be the selected device length which can be varied, e.g., between 10 mm and 35 mm while maintaining the same width and depth to obtain the biopsy. In some embodiments, the biopsy device has a length between 15 mm to 25 mm long.

In some embodiments, the device can have varying flexibility depending on the location that the device is to be positioned against the mucosal surface. Generally, the amount of flexibility required is not large for a measurement taken along the lesser curvature (which is generally flat). In some embodiments, excising the vertical strip of mucosa can be taken along the lesser curvature. In some examples, greater flexibility may be necessary for measuring samples along the anterior and posterior mucosal surface. In some examples, even greater flexibility may be needed to biopsy tissue along the greater curvature where the stomach moves sharply upward from the end of the tube at the angle of HIS.

In some embodiments, the device can facilitate placement of the proximal end of the biopsy device just proximal to the squamo-columnar junction in the retroflex position. In some embodiments, the speed and certainty of the measurement can be increased by using a laser that is configured to define the proximal end of the squamo-columnar junction, and facilitate placement of the proximal end of the biopsy device at that selected point. In some embodiments, the laser can be used to define the point associated with the deployment tool that will fix the proximal end of the device to the point just proximal to the squamo-columnar junction that has been defined by the laser.

In some embodiments, the device will facilitate the placement of the device vertically such that it is flush with the mucosal surface over its 10 mm-35 mm extent. To accomplish this, in some embodiments, the device can be configured to be flexible. In some embodiments, the device is configured to be flexible along its central portion. The device can also include a laser guiding tool that is configured to facilitate the application of the distal end of the device into the mucosa in a vertical orientation as described.

In some examples, the device can have the ability to apply suction. In some embodiments, the suction will suck a portion of the mucosa into the device and subsequently deploy a cutting mechanism at the base of the specimen once it has been sucked into the device. In some examples, the device forms a rectangular trough that can include dimensions of 30 mm long, about 2 mm to 3 mm wide, and a depth of 1 mm to 2 mm. In some embodiments, the trough of the device can be adjustable such to decrease or increase the length of the trough.

An example of the device, sometimes referred to as a biopsy device, is illustrated in FIGS. 6A-6D. As discussed above, in some embodiments, the biopsy device 190 can be inserted into the working channel 110 of the endoscope 100. In some examples, the biopsy device 190 can provide suction through the suction channel 120 of the working channel 110. In some examples, the biopsy device can provide suction through a separate vacuum 150.

Figure 6A:
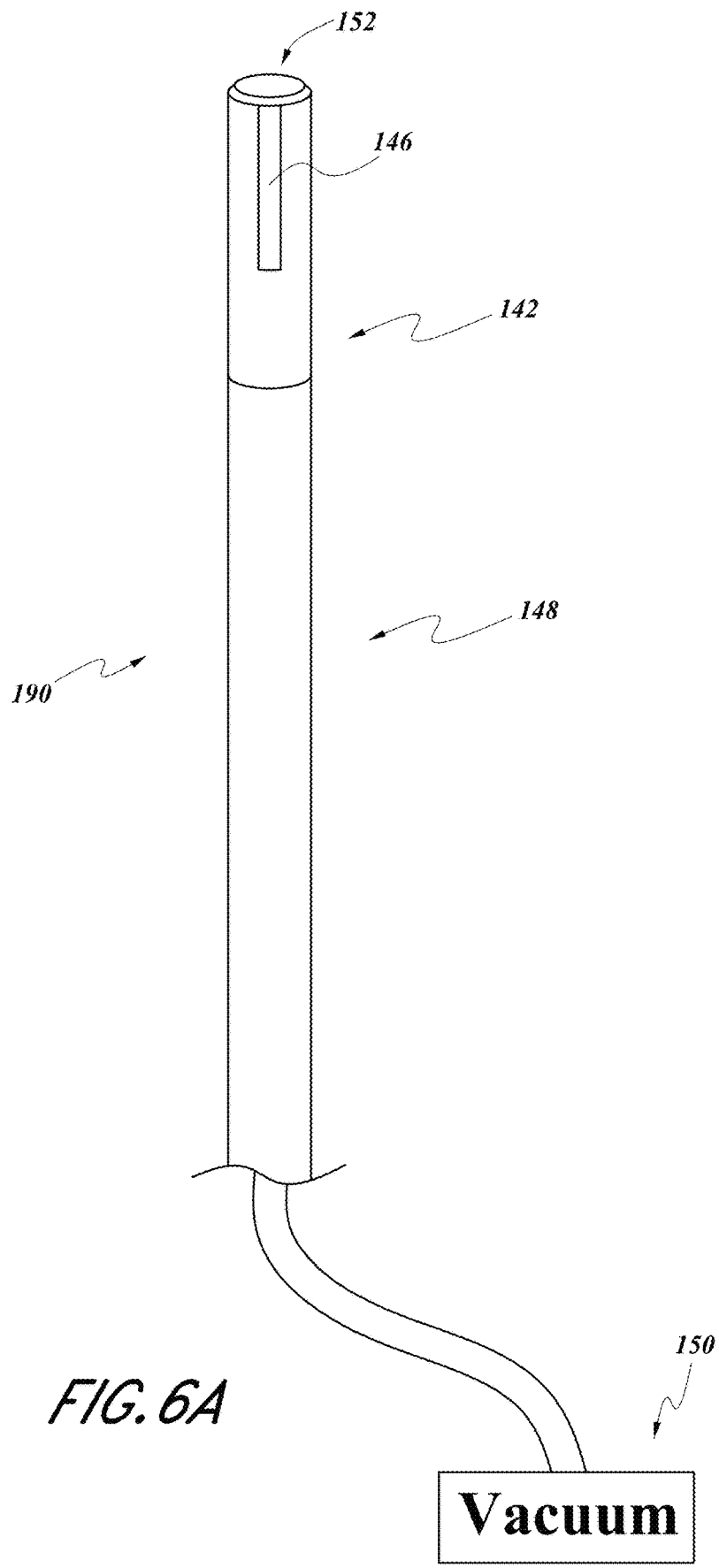

As illustrated in FIG. 6A, in some embodiments, the biopsy device 190 can include a cannula 148 with a biopsy portion 142 located at a distal end 102 of the biopsy device 190. In some embodiments, the biopsy portion 142 can include an opening 146. As will be discussed in more detail below, the opening 146 can allow for the biopsy of tissue from the digestive tract. In some examples, the distal end 102 of the biopsy device 190 can include a cap 152 to allow the biopsy portion 142 to be sealed in the distal direction. In some embodiments, as shown in FIG. 6D, the biopsy portion 142 is in the form of a plug 153 such that the entirety of the biopsy portion 142 is sealed off.

The biopsy portion 142 can form the entire length of the cannula 148. In some embodiments, the biopsy portion 142 forms only the distal end 102 of the cannula 148. In some examples, the biopsy portion 142 can be welded into the cannula 148 or integrated into the cannula 148. In some embodiments, the biopsy portion 142 can be attached to the cannula 148 using any removable configuration such as a pin, clamp, flange, etc.

In some embodiments, as illustrated in FIGS. 6B-6D, the biopsy portion 142 is removable from the cannula 148. In some examples, this can allow the biopsy portion 142 to be disposable. This can provide added cost benefits, allowing only the biopsy portion 142 to be replaced when necessary. As well, the removable biopsy portion 142 can allow the biopsied mucosal tissue to be removed from the biopsy device 190 in a protective or sealed container.

To allow the biopsy portion 142 to be removable from the cannula 148, as illustrated in FIGS. 6B-6D, in some embodiments, the biopsy portion 142 can have a connection portion 156 with external threads 158 that are configured to engage with the internal threads 160 of the cannula 148. In some examples, as the biopsy portion 142 is rotated, the connection portion 156 allows the biopsy portion 142 to be secured to the cannula 148. In some embodiments, the biopsy portion 142 can include an o-ring 154 that helps the biopsy portion 142 and the cannula 148 to form a sealed connection as the biopsy portion 142 is secured onto the cannula 148. In some embodiments, the connection portion 156 between the biopsy portion 142 and the cannula 148 can be in the form of a pin 162 that runs through the proximal end of the biopsy portion 142 and is secured within the distal end of the cannula 148. The pin 162 can be pulled out so as to remove the biopsy portion 142 from the cannula 148.

As discussed above, in some examples, the opening 146 of the biopsy portion 142 (e.g., lateral or side portion) can be placed against the mucosal tissue to biopsy the target tissue. In some embodiments, the stomach can be insufflated with air and, in individuals without Barrett's esophagus, the squamous epithelium appears below the opening of the esophagus. This marks the proximal limit of the placement of the biopsy device and the biopsy device 190 can be positioned vertically from this point along the lesser curvature which is relatively flat. When thus positioned, the biopsy device 190 can apply suction and suck up the mucosa into the interior of the device through the entrance 146. In some embodiments, the tissue that is removed can range approximately from between 2-3 mm wide and 1-2 mm deep.

Figure 7A:
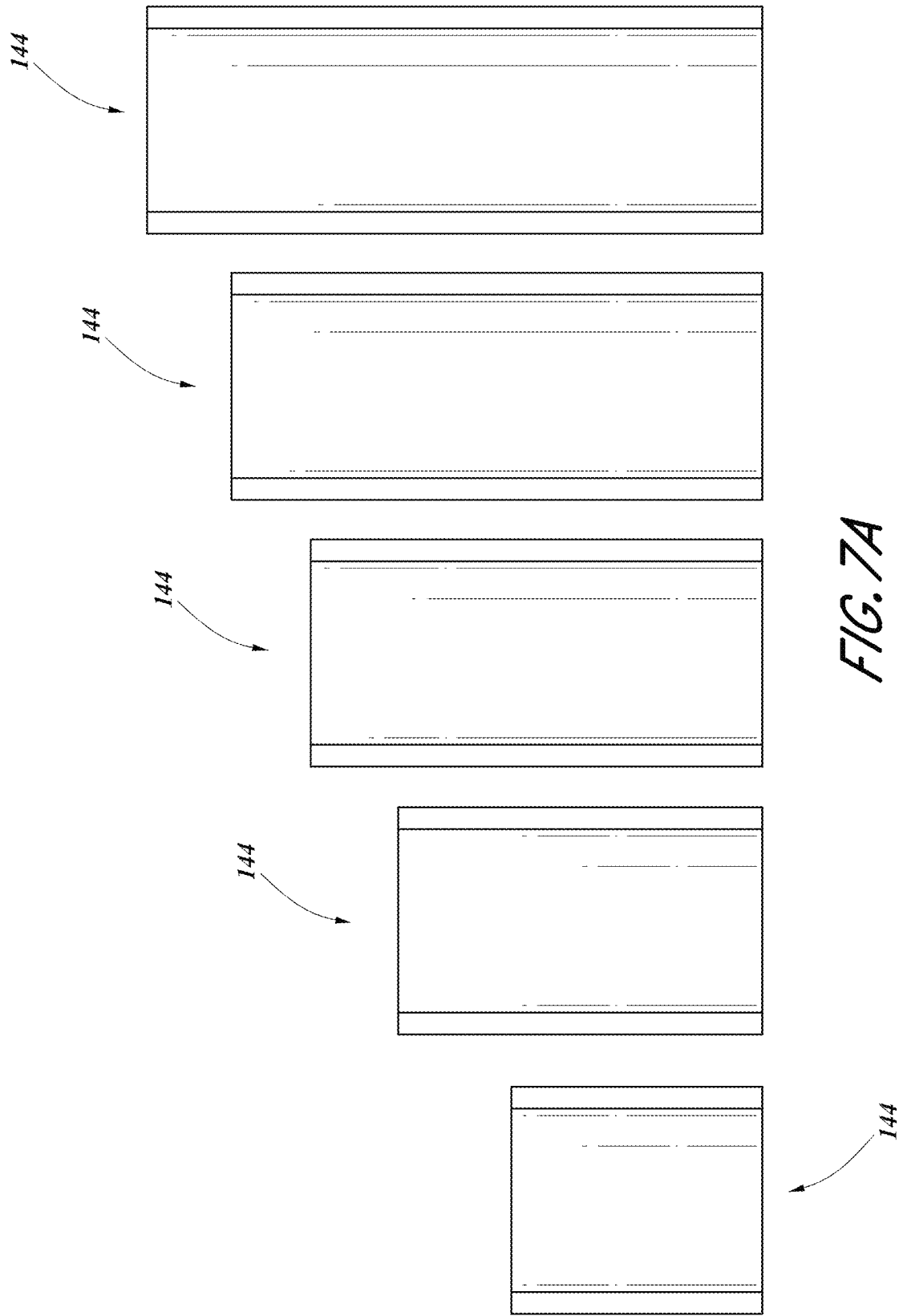

In some examples, the biopsy portion 142 can include an extraction structure 144 that forms the opening 146 of the biopsy portion 142. The extraction structure 144 can have cross-sections in a variety of shapes and sizes. For example, in some embodiments, the extraction structure 144 can have a circular cross-section, a rectangular cross-section, a semi-circular cross-section, etc. FIGS. 7A-7D illustrate an embodiment of the extraction structure 144. In some embodiments, as illustrated in FIGS. 7B-7D, the extraction structure 144 has an omega ("Ω") cross-section.

To provide for a range of different mucosa tissue lengths, in some embodiments, the extraction structure 144 can come in a variety of lengths. For example, as illustrated in FIG. 7A, the extraction structure can range in length from 10-35 mm. In some embodiments, the extraction structure can have a length shorter than 10 mm. In some embodiments, the extraction structure can have a length greater than 30 mm. In some examples, the extraction structure can be adjustable to accommodate different lengths of tissue.

In some examples, the biopsy portion can include a cutting member to biopsy the tissue after the tissue has been suctioned into the opening of the extraction structure. The cutting member can be any number of structures that cuts through the suctioned tissue.

Figure 8B:
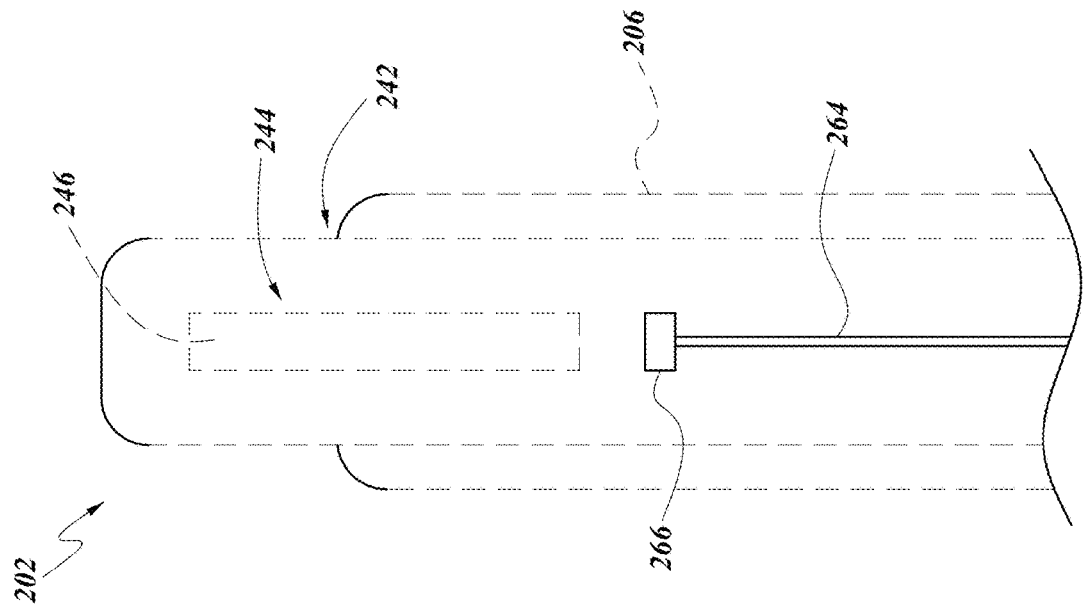
FIGS. 8A-8B illustrate various embodiments of a distal end of a biopsy tool with an embodiment of a cutting member.
Figure 8A:
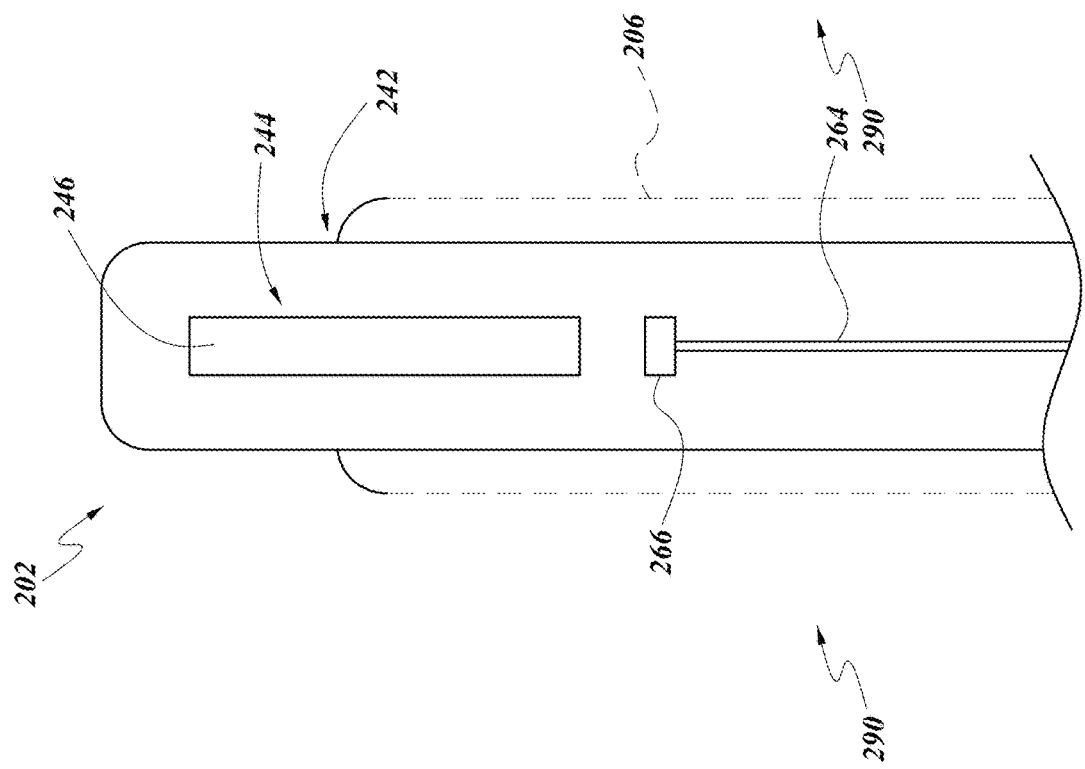

For example, the cutting member of the biopsy portion can be a blade. FIGS. 8A-8B illustrate various embodiments of a biopsy device 290 with a bladed cutting member. The biopsy device 290 can include a biopsy portion 242 located on a distal end 202 of the cannula. The biopsy portion 242 can include an extraction structure 244 with an opening 246 that is configured to suction tissue into the extraction structure 244. As illustrated in FIG. 8A, in some embodiments, the biopsy device 290 can be inserted through the insertion tube 206 of the endoscope to reach the target location of the patient digestive tract.

In some examples, the biopsy device 290 can include a cutting member that includes a cutting edge 266 that is attached to a distal end of a push wire 264. The cutting edge 266 can be any number of shapes. For example, the cutting edge 266 can be rectangular, circular, semi-circular, etc. As illustrated in FIG. 8A, to biopsy the suctioned tissue, the cutting edge 266 can be used to cut the suctioned tissue by advancing the push wire 264 in a distal direction.

The cutting edge 266 and push wire 264 can be advanced external to the biopsy portion 242 or within the biopsy portion 242. FIG. 8A illustrates an example of the cutting edge 266 and push wire 264 located external to the biopsy portion 242. As illustrated in FIG. 8A, advancing the cutting edge 266 on the push wire 264 causes the cutting of the tissue to occur external to the extraction structure 244. FIG. 8B illustrates an example of the cutting edge 266 and push wire 264 located within the biopsy portion 242. As illustrated in FIG. 8B, advancing the cutting edge 266 on the push wire 264 causes the cutting of the tissue to occur within the extraction structure 244.

In some embodiments, the cutting member can be a circular cutting edge. FIGS. 8C-8D illustrate various embodiments of a biopsy device 390 with a circular cutting member. As discussed above with the biopsy device 290, the biopsy device 390 can include a biopsy portion 342 located on a distal end 302 of the cannula. The biopsy portion 342 can include an extraction structure 344 with an opening 346 that is configured to suction tissue into the extraction structure 344. As illustrated in FIG. 8D, in some embodiments, the biopsy device 390 can be inserted through the insertion tube 306 of the endoscope to the reach the target location of the patient digestive tract.

In some examples, the biopsy device 390 can include a cutting member that includes a circular blade portion 368 located at the distal end of a blade support 370. In some embodiments, the blade portion 368 can be integrated into the blade support 370. In some embodiments, the blade portion 368 can be detachable or removable from the distal end of the blade support 370.

The blade support 370 can be located external to the extraction structure 344 or within the biopsy portion 342. Turning first to FIG. 8C, in some embodiments, the blade support 370 can be disposed about the biopsy portion 342. In some examples, by advancing the blade support 370 in a distal direction in a linear or twisting motion, the blade portion 368 of the blade support 370 can cut the tissue external to the extraction structure 344. FIG. 8D illustrates an example of the blade support 370 located within the biopsy portion 342 such that the cannula and biopsy portion 342 is disposed about the blade support 370. As shown in FIG. 8D, advancing the blade support 370 can allow the blade portion 368 of the blade support 370 to cut the tissue from within the extraction structure 344.

In some examples, the cutting member can be a plurality of blades. FIG. 8E illustrates an embodiment of a biopsy device 490 with a cutting member comprising a plurality of blade 472. As discussed above with the biopsy device 290 and the biopsy device 390, the biopsy device 490 can include a biopsy portion 442 located on a distal end 402 of the cannula. The biopsy portion 442 can include an extraction structure 444 with an opening 446 that is configured to suction tissue into the extraction structure 344. As illustrated in FIG. 8E, in some embodiments, the biopsy device 490 can be inserted through the insertion tube 406 of the endoscope to reach the target location of the patient digestive tract.

In some examples, the biopsy device 490 can include a cutting member comprising a blade support 470 with a cutting portion opening 476 located at a distal end of the blade support 470. As illustrated in FIG. 8E, in some examples, the cutting portion opening 476 can have a plurality of blades 472, each with a cutting edge 474 that is configured to cut through tissue within the cutting portion opening 476 and the opening 446. In some embodiments, the plurality of blades 472 are located opposite each other—for example the plurality of blades 472 can be located such that one is distal to another or located such that the plurality of blade 472 parallel to the length of the opening 446.

The blade support 470 can be located external to the extraction structure 444 or within the biopsy portion 442. FIG. 8E illustrates an example of the blade support 470 disposed about the biopsy portion 442. In some examples, the blade support 470 is aligned such that the cutting portion opening 476 is aligned with the opening 446. In some embodiments, the cutting portion opening 476 has dimensions that are larger than the opening 446. This can allow the mucosal tissue to be suctioned through both the cutting portion opening 476 and the opening 446.

In some embodiments, where the plurality of blades 472 are located about the cutting portion opening 476 such that the plurality of blades 472 are parallel to the opening 446, the tissue can be cut by rotating the blade support 470 in a clockwise and/or a counter-clockwise direction to sever the tissue. In examples, where the plurality of blades 472 are located about the cutting portion opening 476 such that the plurality of blade 472 are across from each other, with one distal to the other, the tissue can be cut by advancing and retracting the blade support 470 to sever the tissue.

Figure 8F:
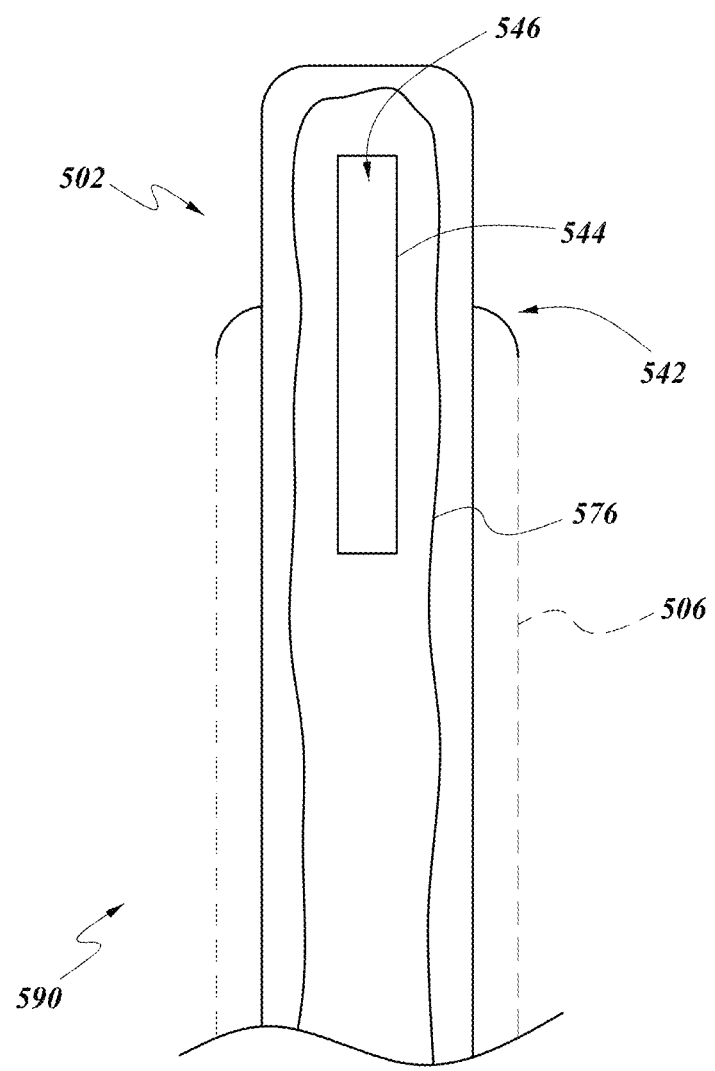
FIG. 8F illustrates an embodiment of a distal end of a biopsy tool with an embodiment of a cutting member comprising a wire.

In some examples, the cutting member can be a wire. FIG. 8F illustrates an embodiment of a biopsy device 590 with a cutting wire 576. As discussed above, the biopsy device 590 can include a biopsy portion 542 located on a distal end 502 of the cannula. The biopsy portion 542 can include an extraction structure 544 with an opening 546 that is configured to suction tissue into the extraction structure 544. As illustrated in FIG. 8F, in some embodiments, the biopsy device 590 can be inserted through the insertion tube 506 of the endoscope to reach the target location of the patient digestive tract.

In some examples, the biopsy device 590 can have a cutting member comprising a wire 576. The cutting wire 576 can be located external to the extraction structure 544 or within the biopsy portion 542. FIG. 8F illustrates an embodiment of the biopsy device 590 with a cutting wire 576 located external to the biopsy portion 542. In some examples, the wire 576 is looped about the extraction structure 544 such that tissue can be suctioned within the opening 546. In some embodiments, the tissue can be cut by retracting the wire 576 in a proximal direction. In some embodiments, the wire 576 can be attached to a power source, such that the cutting surface of the wire 576 can also cauterize the tissue as it cuts through.

In some embodiments, instead of applying suction, the biopsy device can remove a thin layer of the mucosa by pinching the long mucosal segment in one piece. This could be in the form of an arc-shaped cutting instrument that passes into the mucosa at one horizontal edge of the device, passes into the mucosa for a depth of 1 to 2 mm and rejoins the device at the opposite horizontal edge, removing a semicircular piece of mucosa that has the required 10-35 mm length and 1 to 2 mm depth. In some examples, the extraction structure is configured to biopsy the mucosa through a pinching mechanism.

In some examples, once the sample is obtained, the device with the sample can be withdrawn through the endoscope and placed into a container of 10% buffered formalin for fixation with a mechanism of ensuring that the formalin enters the chamber that contains the specimen. In some embodiments, this can be achieved in many ways, including but not limited to an injection port that can permit injection of formalin into the device that contains the mucosal specimen. In some embodiments, the sample is then transported to the pathology laboratory for fixation.

In some embodiments the device can double as a method of transportation of the specimen to the pathology laboratory. The device would be configured to fill the device with formalin after the biopsy has been taken and withdrawn. In some examples, the device is a single use device. This can allow the post-biopsy handling of the specimen to be easier and remove the need to handle the biopsy to transfer it into another container. In some embodiments, this will reduce the chance of damaging the specimen. When removed from the device in the pathology laboratory, the mucosa tissue will already be fixed and be less liable to fragmentation.

In some embodiments, the biopsy device can be a multiple use device. For example, the biopsy device will have to be opened to remove the mucosal sample to be placed into a 10% buffered container for transportation to the laboratory. In some examples, the container to transport the sample can be designed to be in the shape of a rectangular trough to accommodate the sample with as little movement as possible. This can increase the probability that the sample will not fragment during transport to the pathology laboratory.

The sample obtained using the above-mentioned device can provide a 10-35 mm strip of mucosa depending of the length of the biopsy device that was used that will permit a pathologist to measure the length of cardiac epithelium present with the same accuracy as a strip of mucosa obtained in a resection specimen. In some embodiments, the accuracy of the measurement of cardiac epithelial length is within 1 µm.

The use of the biopsy device with standard endoscopy can be difficult as it may require deep conscious sedation. As well, standard endoscopy can be expensive—requiring a fully equipped endoscopy suite in an outpatient center or hospital—and, while safe, can take a long time. To address these concerns, in some embodiments the biopsy device can include structures that allow for the device to be easily, cheaply, safely, and quickly inserted into the body. For example, the device can be inserted along an instrument that has a diameter that is thinner than the formal endoscope to reduce the profile of the inserted device. In some embodiments, to the disclosed biopsy device is configured such that taking a biopsy is its sole purpose. In some examples, it can be made sufficiently thin to be passed easily, quickly, safely, cheaply, and without sedation in a physician's office, by a person with limited training. The biopsy method may be performed in the primary care setting and does not require an endoscopy suite or gastroenterologist.

In some examples, the biopsy device 10-35 mm long, 2-3 mm wide and 1-2 mm deep can be associated with an instrument that include a light source, a lens, a method to insufflate air, and a device for retroflexing. In some embodiments, the instrument to which the biopsy device is attached has a light source and viewing lens that provides basic illumination to allow the operator to see basic landmarks such as the squamo-columnar junction. In some examples, the lens has basic resolution to allow it to be miniaturized. In some examples, the instrument can include a method to insufflate the air to dilate the stomach. In some embodiments, the instrument is configured to retroflex to provide a view of the esophageal opening. In some examples, the instrument can be passed into the stomach. In some embodiments, the instrument can be retroflexed and air insufflated to visualize the squamocolumnar junction. In some examples, the biopsy device can then be deployed and positioned to allow the mucosal biopsy sample to be taken.

In some embodiments, the biopsy device can be configured to engage a miniaturized endoscope, such as a transnasal endoscope or smaller. In some embodiments, the biopsy device can be attached to and directed by a fiber-optic camera device. In some examples, the biopsy device can be configured to "piggy-back" on the miniaturized endoscope. In some examples, the biopsy device is configured to be maneuvered into position to take the biopsy as discussed above and subsequently returned to its original position.

FIG. 9 illustrates an embodiment of a trans-nasal endoscope that the biopsy device can be designed to piggy-back on. As shown, in some embodiments, the trans-nasal endoscope 600 can include an insertion tube 606 with a distal end 602. As discussed above with regard to the endoscope 100, the insertion tube 606 of the trans-nasal endoscope 600 can allow a physician to access a portion of the patient's digestive tract at the distal end 602 of the insertion tube 606. In some examples, the trans-nasal endoscope 600 can include a control section 678 that allows the physician to control the trans-nasal endoscope 600. The trans-nasal endoscope 600 can include a universal cord 622 that can provide the trans-nasal endoscope 600 with power or other external sources.

FIGS. 10A-10B illustrate an embodiment of a distal end of the trans-nasal endoscope 600. As discussed above, in some examples, the distal end 602 of the insertion tube 606 can include a plurality of lumens. For example, the insertion tube 606 can include a working channel 610 that can allow a biopsy device to be inserted through. In some examples, the working channel 610 can also serve as a suction channel 620—the suction channel 620 being fluidly connected to a vacuum. In some examples, the insertion tube 606 can include visualization tools (e.g. objective lens 680 or illumination lens 682) that allow the distal end 602 of the insertion tube 606 to be visualized. In some embodiments, not pictured, the insertion tube 606 can also include control wires that allow the distal end 602 of the insertion tube 606 to be flexed.

In some embodiments, the biopsy device is disposed over a guidewire (not illustrated). The guidewire can be used alone or with the endoscope. In some examples, the tools mentioned above (e.g., visualization tools, light source, biopsy tools, vacuum, etc.) can be guided to the target tissue in the patient's digestive tract along the guidewire. In some embodiments, the guidewire can be retroflexed to provide the guidewire with added flexibility.

In some embodiments, a pressure sensor can be used to determine the approximate length of the dilated distal esophagus (e.g., the squamo-oxyntic gap) and therefore provide the physician with a better idea of the location and/or length of the dilated distal esophagus. For example, the pressure sensor can be located at a distal end of the guidewire.

In some examples, the guidewire is inserted in the patient's esophagus and the pressure sensor is configured to identify the point along the esophagus where a pressure change occurs. The pressure change approximately identifies the transition point between the lower esophageal sphincter and the dilated distal esophagus. In some embodiments, the pressure sensor can be connected to a visual or audio indicator such that when the pressure change point is identified, the user is notified through an audio indicator (e.g., a beep) or a visual indicator (e.g., a flashing light). The biopsy can therefore be taken in a vertical segment from the pressure change point to the proximal end of the stomach. In some embodiments, the pressure sensor is located a distance (e.g., 1 cm) proximal to the pressure change point. This can ensure that the biopsied tissue includes the entire length of the dilated distal esophagus (e.g., squamo-oxyntic gap).

Non-Endoscopic Measurement of Cardiac Epithelial Length

The aforementioned methods described for the measurement of cardiac epithelial length requires endoscopy. Because of cost and the availability of resources, the requirement of endoscopy can potentially serve as a limiting factor in terms of the ability to measure the dilated distal esophagus.

In some embodiments, a non-endoscopic method for measuring cardiac epithelial involves the use of optical coherence tomography ("OCT"). OCT uses optical coherence that can provide a tomographic image of the layers of the esophagus. In some embodiments, the tomographic views provided using OCT can permit the identification of the muscularis mucosae, a thin layer of muscle at the deep aspect of the mucosa. In squamous epithelium, this can be seen as a thin, well defined horizontal layer below the normally thin epithelium. In gastric oxyntic epithelium, there is a similar thin, well defined horizontal layer below the normal gastric oxyntic epithelium which is much thicker because of its long glands. In cardiac epithelium, the muscularis mucosae becomes hyperplastic and irregular with muscle fibers going vertically both upward and downward. Therefore, this results in a loss of definition of the muscularis mucosae. As such, in some embodiments, it is possible that the gap between the well-defined mucularis mucosae under the squamous epithelium and that under gastric oxyntic epithelium will be an accurate measure of cardiac epithelium.

In some embodiments, the non-endoscopic device can be attached to a retractable device and passed down beyond the LES into the stomach and pulled up to make the measurement. In some examples, the device is passed downwards into the stomach by swallowing.

In some examples, the device spins and can be withdrawn slowly to provide an image that can be analyzed to provide a longitudinal section from the stomach to the squamous epithelium. In some embodiments, the OCT device can be configured to provide a circumferential image of the whole esophagus. In some embodiments, the OCT device when placed against one side of the gastric mucosa and pulled up along that wall into the esophagus, can provide a longitudinal image that can potentially delineate the muscularis mucosae of the proximal limit of gastric oxyntic epithelium and the distal limit of the esophageal squamous epithelium.

In some embodiments, the disclosed test can be conducted by anyone without the need for endoscopy as such a method of measuring the length of cardiac epithelium will dramatically increase the potential scope of the test. In some examples, this can enable the test to be conducted in any physician's office or even at home.

Non-Histologic Methods for Measuring Cardiac Epithelial Length

In some embodiments, the length of the dilated distal esophagus (e.g., the squamo-oxyntic gap) can be determined using non-histologic methods. For example, the dilated distal esophagus can be determined using endoscopic methods without needing to biopsy tissue. In other examples, the following methods can be used in conjunction with endoscopy. In some embodiments, this can alter the steps and types of devices that need to be inserted into the patient. For example, as will be discussed below, if the non-histologic method uses imaging, only a fiber-optic cable would need to be inserted into a patient to image the target tissue (e.g., through the working channel of an endoscope or along a guidewire)—no biopsy device would need to be inserted.

In some examples, a method may include using chromo-endoscopy where dyes are introduced to stain the epithelium. In some embodiments, the dye is sprayed on the surface of the target tissue. The dye can be used to distinguish cardiac epithelium from gastric oxyntic epithelium. In some examples, the dye is configured to stain for mucin types. In some embodiments, the dyes can be Lugol's iodine or toluidine blue.

In some embodiments, confocal microscopy may be used to determine the length of the dilated distal esophagus. In some examples, confocal microscopy can determine the length of the relevant tissue by determining whether there is a difference in the pit patterns of cardiac epithelium and oxyntocardiac epithelium.

In some examples, the length of the dilated distal esophagus can be determined by taking a computer image of the area distal to the squamo-columnar junction in the endoscopically normal person. In some embodiments, this computer image may then be subjected to image analysis to differentiate between cardiac epithelium and gastric oxyntic epithelium.

While the invention has been particularly shown and described with reference to specific embodiments, it should be understood by those skilled in the art that various changes in form and detail may be made without departing from the spirit and scope of the invention as defined by the appended claims.

What is claimed is:

1. A method of determining progression of reflux disease in an esophagus of a patient, the method comprising:
    identifying a location of an endoscopic gastroesophageal junction in the esophagus;
    removing a length of tissue of the esophagus, wherein the length of tissue includes a portion of the endoscopic gastroesophageal junction, using a device comprising:
        a cannula having a proximal end, a distal end, and a wall extending between the proximal and distal ends, and a lumen extending from a proximal region near the proximal end towards a distal region near the distal end,
        an opening in the wall in the distal region, wherein the opening is in fluid communication with the lumen,
        a connector in fluid communication with the lumen at the proximal region, wherein the connector is adapted to be connected to a vacuum source, and
        a cutting member positioned near the opening and movable with respect to the opening;
    identifying, using the length of tissue, a proximal limit of tissue containing cardiac epithelium;
    determining a length of the squamo-oxyntic gap of a biopsied tissue by measuring the length of tissue extending between a proximal limit of tissue containing gastric oxyntic epithelium to the proximal limit of tissue containing cardiac epithelium;
    determining a linear relationship comprising a slope of a line extending between a first data point and a second data point:
        wherein the first data point corresponds to a first lower esophageal sphincter length and a first age, and
        wherein the second data point corresponds to a second lower esophageal sphincter length and an age of the patient; and
    determining a target age of the patient when a lower esophageal sphincter will have a length less than or equal to 10 mm using the linear relationship.

2. The method of claim 1, wherein a length of the length of tissue is in the range of 5 mm to 30 mm or wherein a width of the length of tissue is in the range of 2 mm to 3 mm or wherein a thickness of the length of tissue is in the range of 1 mm to 2 mm.

3. The method of claim 1, wherein the first data point corresponds to a lower esophageal sphincter length of 35 mm at age of 10 if the patient has a history of childhood obesity, or a lower esophageal sphincter length of 35 mm at age of 15 if the patient does not have a history of childhood obesity.

4. The method of claim 1, wherein identifying the endoscopic gastroesophageal junction comprises using any one of an endoscope, trans-nasal endoscope, and optical coherence tomography.

5. The method of claim 1, wherein determining the length of the squamo-oxyntic gap comprises using chromo-endoscopy.

6. The method of claim 1 wherein the first lower esophageal sphincter length is 35 mm and the second lower esophageal sphincter length is the difference of 35 mm and the length of the squamo-oxyntic gap.

7. The method of claim 1, further comprising a biopsy portion removably attached to the cannula, wherein the biopsy portion comprises the distal region.

8. The method of claim 7 wherein the biopsy portion includes a proximal attachment portion and the cannula is configured to receive the proximal attachment portion of the biopsy portion.

9. The method of claim 8 wherein the proximal attachment portion is secured using an external thread or a removable pin configured to secure the biopsy portion to the cannula.

10. The method of claim 7 further including an o-ring configured to form a seal between the biopsy portion and the distal end of the cannula.

11. The method of claim 1, wherein the distal region has any one of a c-shaped cross-section and an omega-shaped cross-section.

12. The method of claim 1 further comprising the vacuum source.

13. The method of claim 1, wherein the cutting member comprises a blade or a wire that is any one of rectangular, cylindrical, and semi-cylindrical shapes.

14. The method of claim 1, further comprising an actuator or a wire coupled to the cutting member, wherein the actuator or wire is configured to move axially within the distal region or axially adjacent to an outer surface of the distal region.

15. The method of claim 1, wherein the cutting member is tubular with a circular cutting edge or tubular with an opening that is aligned about the opening of the extraction structure, the cutting member configured to cut tissue extending within the opening of the extraction structure.

16. The method of claim 15, wherein the opening has a length along an axial length of the cannula of between 10 mm to 35 mm and/or a width along a circumferential direction of the cannula of between and including 1 mm-2 mm, 2 mm-3 mm, 3 mm-4 mm, 4 mm-5 mm, 5 mm-6 mm, 6 mm-7 mm, 7 mm-8 mm, 8 mm-9 mm, and 9 mm-10 mm.

17. The method of claim 1, wherein the cutting member includes a plurality of blades wherein the plurality of blades are located along opposite sides of the opening and wherein the cutting member is configured rotate circumferentially with respect to the opening.

18. A method of determining progression of reflux disease in an esophagus of a patient, the method comprising:

identifying a location of an endoscopic gastroesophageal junction in the esophagus;

removing a length of tissue of the esophagus, wherein the length of tissue includes a portion of the endoscopic gastroesophageal junction;

identifying, using the length of tissue, a proximal limit of tissue containing cardiac epithelium;

determining a length of the squamo-oxyntic gap of a biopsied tissue by measuring the length of tissue extending between a proximal limit of tissue containing gastric oxyntic epithelium to the proximal limit of tissue containing cardiac epithelium; and determining a target age of the patient when a lower esophageal sphincter will have a length less than or equal to 10 mm, wherein the target age is based on a relationship between a first data point and a second data point, wherein the first data point corresponds to a first lower esophageal sphincter length and a first age, and wherein the second data point corresponds to a second lower esophageal sphincter length and an age of the patient.

19. The method of claim 18, wherein the first data point corresponds to a lower esophageal sphincter length of 35 mm at age of 10 if the patient has a history of childhood obesity, or a lower esophageal sphincter length of 35 mm at age of 15 if the patient does not have a history of childhood obesity.

20. The method of claim 18 wherein the first lower esophageal sphincter length is 35 mm and the second lower esophageal sphincter length is the difference of 35 mm and the length of the squamo-oxyntic gap.

* * * * *